US008377677B2

(12) United States Patent
De Maria et al.

(10) Patent No.: US 8,377,677 B2
(45) Date of Patent: *Feb. 19, 2013

(54) PROTEASE VARIANTS

(75) Inventors: Leonardo De Maria, Frederiksberg (DK); Carsten Andersen, Vaerlose (DK); Lars Lehmann Hylling Christensen, Allerod (DK); Soren Flensted Lassen, Farum (DK); Peter Rahbek Ostergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,826

(22) Filed: Jan. 5, 2011

(65) Prior Publication Data
US 2011/0097445 A1 Apr. 28, 2011

Related U.S. Application Data

(63) Continuation of application No. 10/574,554, filed as application No. PCT/DK2004/000688 on Oct. 8, 2004, now Pat. No. 7,892,808.

(60) Provisional application No. 60/549,347, filed on Mar. 2, 2004, provisional application No. 60/510,450, filed on Oct. 10, 2003.

(30) Foreign Application Priority Data

Oct. 10, 2003 (DK) .................................. 2003 01494
Mar. 1, 2004 (DK) .................................. 2004 00333

(51) Int. Cl.
*C12N 9/52* (2006.01)
*C11D 3/386* (2006.01)
*C12N 15/57* (2006.01)
*C12N 15/73* (2006.01)

(52) U.S. Cl. ............ 435/220; 435/69.1; 435/252.3; 435/320.1; 510/300; 536/23.2

(58) Field of Classification Search .................. None
See application file for complete search history.

(56) References Cited

U.S. PATENT DOCUMENTS

| 3,683,069 A | 8/1972 | Hooreman |
| 3,723,250 A | 3/1973 | Aunstrup et al. |
| 3,823,072 A | 7/1974 | Hooreman |
| 3,868,448 A | 2/1975 | Hahn et al. |
| 3,966,971 A | 6/1976 | Morehouse et al. |
| 4,073,884 A | 2/1978 | Hartdegen |
| 4,518,697 A | 5/1985 | Bartnik et al. |

(Continued)

FOREIGN PATENT DOCUMENTS

| DE | 2004328 | 5/1983 |
| DK | PA 2003 00013 | 1/1996 |

(Continued)

OTHER PUBLICATIONS

Goodenough et al., Molecular Biotechnology, vol. 4, No. 1, pp. 151-166 (1995).

(Continued)

*Primary Examiner* — Manjunath Rao
*Assistant Examiner* — William W Moore
(74) *Attorney, Agent, or Firm* — Elias Lambiris

(57) ABSTRACT

The invention relates to a novel 3D structure encoding a *Nocardiopsis* protease, as well as to variants of parent protease homologous to *Nocardiopsis* proteases, preferably of improved thermostability and/or with an amended temperature activity profile. The invention also relates to DNA sequences encoding such variants, their production in a recombinant host cell, as well as methods of using the variants, in particular within the field of animal feed and detergents. The invention furthermore relates to methods of generating and preparing protease variants of amended properties.

49 Claims, 26 Drawing Sheets

```
                    1                                                  50
Protease 10   ADIIGGLAYTMGGRCSVGFAATNAAGQPGFVTAGHCGRVGTQVTIGNGRG
Protease 18   ADIIGGLAYYMGGRCSVGFAATNSAGQPGFVTAGHCGTVGTGVTIGNGTG
Protease 11   ADIIGGLAYTMGGRCSVGFAATNAAGQPGFVTAGHCGRVGTQVSIGNGQG
Protease 35   ADIIGGLAYTMGGRCSVGFAATNAAGQPGFVTAGHCGRVGTQVTIGNGRG
Protease 08   ADIIGGLAYTMGGRCSVGFAATNASGQPGFVTAGHCGTVGTPVSIGNGQG
Protease 22   ADIIGGLAYYMGGRCSVGFAATNASGQPGFVTAGHCGTVGTPVSIGNGKG 51                                                 100
Protease 10   VFEQSVFPGNDAAFVRGTSNFTLTNLVSRYNTGGYATVAGHNQAPIGSSV
Protease 18   TFQNSVFPGNDAAFVRGTSNFTLTNLVSRYNSGGYQSVTGTSQAPAGSAV
Protease 11   VFEQSIFPGNDAAFVRGTSNFTLTNLVSRYNTGGYATVAGHNQAPIGSSV
Protease 35   VFEQSIFPGNDAAFVRGTSNFTLTNLVSRYNTGGYATVAGHNQAPIGSSV
Protease 08   VFERSVFPGNDSAFVRGTSNFTLTNLVSRYNTGGYATVSGSSQAAIGSQI
Protease 22   VFERSIFPGNDSAFVRGTSNFTLTNLVSRYNSGGYATVAGHNQAPIGSAV 101                                                150
Protease 10   CRSGSTTGWHCGTIQARGQSVSYPEGTVTNMTRTTVCAEPGDSGGSYISG
Protease 18   CRSGSTTGWHCGTIQARNQTVRYPQGTVYSLTRTNVCAEPGDSGGSFISG
Protease 11   CRSGSTTGWHCGTIQARGQSVSYPEGTVTNMTRTTVCAEPGDSGGSYISG
Protease 35   CRSGSTTGWHCGTIQARGQSVSYPEGTVTNMTRTTVCAEPGDSGGSYISG
Protease 08   CRSGSTTGWHCGTVQARGQTVSYPQGTVQNLTRTNVCAEPGDSGGSFISG
Protease 22   CRSGSTTGWHCGTIQARNQTVRYPQGTVYSLTRTTVCAEPGDSGGSYISG 151                            188
Protease 10   TQAQGVTSGGSGNCRTGGTTFYQEVTPMVSWGVRLRT
Protease 18   SQAQGVTSGGSGNCSVGGTTYYQEVTPMINSWGVRIRT
Protease 11   NQAQGVTSGGSGNCRTGGTTFFYQEVTPMVSWGVRLRT
Protease 35   NQAQGVTSGGSGNCRTGGTTFFYQEVTPMVSWGVRLRT
Protease 08   SQAQGVTSGGSGNCSFGGTTYYQEVNPMLSSWGLTLRT
Protease 22   TQAQGVTSGGSGNCSAGGTTYYQEVNPMLSSWGLTLRT
```

U.S. PATENT DOCUMENTS

| | | | |
|---|---|---|---|
| 5,047,240 A | 9/1991 | Hooreman | |
| 5,312,748 A | 5/1994 | Liu et al. | |
| 5,646,028 A | 7/1997 | Leigh | |
| 5,705,379 A | 1/1998 | Wilson et al. | |
| 5,811,382 A | 9/1998 | Damhus et al. | |
| 5,877,403 A | 3/1999 | McMaster et al. | |
| 6,855,548 B2 | 2/2005 | Sjoeholm | |
| 6,960,462 B2 | 11/2005 | Sjoeholm et al. | |
| 7,179,630 B2 | 2/2007 | Lassen et al. | |
| 7,208,310 B2 | 4/2007 | Lassen et al. | |
| 7,485,447 B2 | 2/2009 | Lassen | |
| 7,588,926 B2 | 9/2009 | Oestergaard et al. | |
| 7,608,444 B2 | 10/2009 | Oestergaard et al. | |
| 7,618,801 B2 | 11/2009 | Jones et al. | |
| 7,630,836 B2 | 12/2009 | Omura et al. | |
| 7,658,965 B2 | 2/2010 | Sjoeholm et al. | |
| 7,892,808 B2 | 2/2011 | De Maria et al. | |
| 7,906,310 B2 | 3/2011 | Oestergaard et al. | |
| 8,067,238 B2 * | 11/2011 | Sjoeholm et al. | 435/422 |
| 8,153,396 B2 * | 4/2012 | Lynglev et al. | 435/68.1 |
| 2001/0026797 A1 | 10/2001 | Sjoeholm et al. | |
| 2006/0143738 A1 | 6/2006 | Lassen | |
| 2006/0147499 A1 | 7/2006 | Oestergaard | |
| 2006/0236414 A1 | 10/2006 | Lassen | |
| 2007/0104764 A1 | 5/2007 | Jensen et al. | |
| 2007/0259404 A1 | 11/2007 | Jorgensen et al. | |
| 2008/0286415 A1 | 11/2008 | Lassen | |
| 2008/0293104 A1 | 11/2008 | Lassen | |
| 2010/0081168 A1 | 4/2010 | Sjoeholm et al. | |
| 2010/0093025 A1 * | 4/2010 | Kalum | 435/68.1 |
| 2010/0093633 A1 | 4/2010 | De Maria et al. | |
| 2010/0255153 A1 | 10/2010 | Oestergaard et al. | |
| 2010/0322915 A1 * | 12/2010 | Svendsen et al. | 424/94.61 |
| 2011/0081450 A1 * | 4/2011 | Lynglev et al. | 426/52 |
| 2011/0097448 A1 * | 4/2011 | Wong et al. | 426/72 |
| 2011/0097760 A1 * | 4/2011 | Lynglev et al. | 435/68.1 |

FOREIGN PATENT DOCUMENTS

| | | |
|---|---|---|
| EP | 0 130 756 | 1/1985 |
| EP | 0 300 466 | 1/1989 |
| EP | 0 506 448 | 9/1992 |
| EP | 0 516 200 | 12/1992 |
| EP | 0 647 710 | 4/1995 |
| EP | 0 897 985 | 2/1999 |
| JP | 02255081 | 10/1990 |
| JP | 2003 284571 | 10/2003 |
| JP | 2004 043660 | 2/2004 |
| WO | WO 88/03947 | 6/1988 |
| WO | WO 91/00345 | 1/1991 |
| WO | WO 91/10723 | 7/1991 |
| WO | WO 92/19729 | 11/1992 |
| WO | WO 95/02044 | 1/1995 |
| WO | WO 95/21540 | 8/1995 |
| WO | WO 95/28850 | 11/1995 |
| WO | WO 96/05739 | 2/1996 |
| WO | WO 98/56260 | 12/1998 |
| WO | WO 99/53038 | 10/1999 |
| WO | WO 01/58276 | 8/2001 |
| WO | WO 2004/070106 | 8/2004 |
| WO | WO 2004/072221 | 8/2004 |
| WO | WO 2004/072279 | 8/2004 |
| WO | WO 2004/111219 | 12/2004 |
| WO | WO 2004/111220 | 12/2004 |
| WO | WO 2004/111221 | 12/2004 |
| WO | WO 2004/111222 | 12/2004 |
| WO | WO 2004/111223 | 12/2004 |
| WO | WO 2004/111224 | 12/2004 |
| WO | 2005/115445 A1 | 12/2005 |

OTHER PUBLICATIONS

Vieille et al., Microbiology and Molecular Biology Reviews, vol. 65, No. 1, pp. 1-43 (2001).
Sambrook et al., Molecular Cloning 3rd Edition, vol. 2, pp. 10.47-10.48 (2001).
Altschul et al., GenPept Database, Accession No. PQ0104 (1997).
Anderson et al., Database GeneSeq, Accession No. AAQ29011—Seq0001, (1992).
Anderson et al., Database GeneSeq, Accession No. AAQ29011—Seq0011, (1992).
Barrett et al., Handbook of Proteolytic Enzymes, pp. 2-3 (1998).
Caine et al., Animal Feed Sci. Technology, vol. 71, pp. 177-183 (1998).
Derwent Abstract: XP-002310338 published Aug. 19, 2004.
Derwent Abstract: XP-002308395 submitted (Sep. 18, 2002) to the EMBL/GenBankDDBJ databases.
Dixit et al., Biochim. Biophys. Acta, vol. 1523, No. 2-3, pp. 261-268 (2000).
Gayle et al., J. Biol. Chem., vol. 268, No. 29, pp. 22105-22111 (1993).
Gill et al., Analytical Biochem., vol. 182, pp. 319-326 (1989).
Henderson et al., J. Bacteriol., vol. 169, No. 8, pp. 3778-3784 (1987).
Heringa et al., Protein Engineering, vol. 8, No. 1, pp. 21-30 (1995).
Higgins et al., Gene, vol. 73, pp. 237-244 (1988).
Kaneda et al., J. Biochem., vol. 78, pp. 1287-1296 (1975).
Kim et al., Korean Biotech. J., vol. 26, No. 1, pp. 81-85 (1993).
Lao et al., Appl. Environ. Microbiol., vol. 62, No. 11, pp. 4256-4259 (1996).
Merops Database, Alignment of Subfamily S1E Peptidases (2004).
Michalik et al., Ukr. Biokhim. Zh., vol. 69, No. 3, pp. 28-35 (1997), English abstract only.
Mitsuiki et al., Biosci. Biotechnol. Biochem., vol. 66, No. 1, pp. 164-167 (2002).
Mitsuiki et al., Database EMBL, Accession No. AY151208 (2004).
Mitsuiki et al., Enzyme and Microbiol Technology, vol. 34, No. 5, pp. 482-489 (2004).
Moreira et al., World Journal of Microbiology and Biotechnology, vol. 18, No. 4, pp. 307-312 (2002).
Needleman et al., J. Mol. Biology, vol. 48, pp. 443-453 (1970).
Novozymes, Database A_Geneseq, Accession No. AAW92997 (1999).
Novozymes, Database N_Geneseq, Accession No. AAX22316 (1999).
O'Fagain, Enzyme and Microbial Technology, vol. 33, pp. 137-149 (2003).
Ostergaard et al., Database A_Geneseq, Accession No. AAU07125, (2003).
Refstie et al., Aquaculture, vol. 162, pp. 301-312 (1998).
Screen et al., J. Biol. Chem., vol. 275, No. 9, pp. 6689-6694 (2000).
Sidhu et al., J. Biol. Chem., vol. 269, No. 31, pp. 20167-20171 (1994).
Smith et al., Analytical Biochem., vol. 150, pp. 76-85 (1985).
Tsuijibo et al., Agric. Biol. Chem., vol. 54, No. 8, pp. 2177-2179 (1990).
Tsuijibo et al., J. Appl. Bacteriol., vol. 69, pp. 520-529 (1990).
Tsuijibo et al, Appl. Environ. Microbiol., vol. 69, No. 2, pp. 894-900 (2003).
Whisstock et al, Quart. Rev. Biophysic., vol. 36, No. 3, pp. 307-340 (2003).
FASTA Sequence alignments, (1993, 1994, and 2002).
Fernandez-Abalos et al., Microbiology, vol. 149, pp. 1623-1632 (2003).

* cited by examiner

```
              1                                                 50
Protease 10   ADIIGGLAYTMGGRCSVGFAATNAAGQPGFVTAGHCGRVGTQVTIGNGRG
Protease 18   ADIIGGLAYYMGGRCSVGFAATNSAGQPGFVTAGHCGTVGTGVTIGNGTG
Protease 11   ADIIGGLAYTMGGRCSVGFAATNAAGQPGFVTAGHCGRVGTQVSIGNGQG
Protease 35   ADIIGGLAYTMGGRCSVGFAATNAAGQPGFVTAGHCGRVGTQVTIGNGRG
Protease 08   ADIIGGLAYTMGGRCSVGFAATNASGQPGFVTAGHCGTVGTPVSIGNGQG
Protease 22   ADIIGGLAYYMGGRCSVGFAATNASGQPGFVTAGHCGTVGTPVSIGNGKG 51                                                100
Protease 10   VFEQSVFPGNDAAFVRGTSNFTLTNLVSRYNTGGYATVAGHNQAPIGSSV
Protease 18   TFQNSVFPGNDAAFVRGTSNFTLTNLVSRYNSGGYQSVTGTSQAPAGSAV
Protease 11   VFEQSIFPGNDAAFVRGTSNFTLTNLVSRYNTGGYATVAGHNQAPIGSSV
Protease 35   VFEQSIFPGNDAAFVRGTSNFTLTNLVSRYNTGGYATVAGHNQAPIGSSV
Protease 08   VFERSVFPGNDSAFVRGTSNFTLTNLVSRYNTGGYATVSGSSQAAIGSQI
Protease 22   VFERSIFPGNDSAFVRGTSNFTLTNLVSRYNSGGYATVAGHNQAPIGSAV 101                                               150
Protease 10   CRSGSTTGWHCGTIQARGQSVSYPEGTVTNMTRTTVCAEPGDSGGSYISG
Protease 18   CRSGSTTGWHCGTIQARNQTVRYPQGTVYSLTRTNVCAEPGDSGGSFISG
Protease 11   CRSGSTTGWHCGTIQARGQSVSYPEGTVTNMTRTTVCAEPGDSGGSYISG
Protease 35   CRSGSTTGWHCGTIQARGQSVSYPEGTVTNMTRTTVCAEPGDSGGSYISG
Protease 08   CRSGSTTGWHCGTVQARGQTVSYPQGTVQNLTRTNVCAEPGDSGGSFISG
Protease 22   CRSGSTTGWHCGTIQARNQTVRYPQGTVYSLTRTTVCAEPGDSGGSYISG 151                        188
Protease 10   TQAQGVTSGGSGNCRTGGTTFYQEVTPMVNSWGVRLRT
Protease 18   SQAQGVTSGGSGNCSVGGTTYYQEVTPMINSWGVRIRT
Protease 11   NQAQGVTSGGSGNCRTGGTTFYQEVTPMVNSWGVRLRT
Protease 35   NQAQGVTSGGSGNCRTGGTTFYQEVTPMVNSWGVRLRT
Protease 08   SQAQGVTSGGSGNCSFGGTTYYQEVNPMLSSWGLTLRT
Protease 22   TQAQGVTSGGSGNCSAGGTTYYQEVNPMLSSWGLTLRT
```

Fig. 1

| ATOM | 1 | N | ALA | 1 | -18.517 | 32.531 | 28.661 | 1.00 | 8.90 |
|---|---|---|---|---|---|---|---|---|---|
| ATOM | 2 | CB | ALA | 1 | -18.802 | 30.741 | 30.290 | 1.00 | 12.24 |
| ATOM | 3 | CA | ALA | 1 | -19.308 | 31.313 | 28.965 | 1.00 | 10.86 |
| ATOM | 4 | C | ALA | 1 | -20.783 | 31.666 | 29.080 | 1.00 | 12.18 |
| ATOM | 5 | O | ALA | 1 | -21.113 | 32.695 | 29.712 | 1.00 | 12.73 |
| ATOM | 6 | N | ASP | 2 | -21.722 | 30.930 | 28.510 | 1.00 | 12.01 |
| ATOM | 7 | CA | ASP | 2 | -23.176 | 31.225 | 28.612 | 1.00 | 12.07 |
| ATOM | 8 | C | ASP | 2 | -23.667 | 30.604 | 29.929 | 1.00 | 10.24 |
| ATOM | 9 | O | ASP | 2 | -23.359 | 29.410 | 30.109 | 1.00 | 11.30 |
| ATOM | 10 | CB | ASP | 2 | -23.995 | 30.629 | 27.422 | 1.00 | 12.43 |
| ATOM | 11 | CG | ASP | 2 | -23.545 | 31.314 | 26.129 | 1.00 | 16.23 |
| ATOM | 12 | OD1 | ASP | 2 | -23.300 | 30.668 | 25.134 | 1.00 | 21.68 |
| ATOM | 13 | OD2 | ASP | 2 | -23.346 | 32.527 | 26.168 | 1.00 | 17.64 |
| ATOM | 14 | N | ILE | 3 | -24.387 | 31.321 | 30.757 | 1.00 | 9.80 |
| ATOM | 15 | CA | ILE | 3 | -24.850 | 30.687 | 32.027 | 1.00 | 8.80 |
| ATOM | 16 | C | ILE | 3 | -26.252 | 30.135 | 31.768 | 1.00 | 7.97 |
| ATOM | 17 | O | ILE | 3 | -27.160 | 30.953 | 31.648 | 1.00 | 8.91 |
| ATOM | 18 | CB | ILE | 3 | -24.789 | 31.723 | 33.207 | 1.00 | 7.85 |
| ATOM | 19 | CG1 | ILE | 3 | -23.378 | 32.342 | 33.312 | 1.00 | 5.63 |
| ATOM | 20 | CG2 | ILE | 3 | -25.284 | 31.096 | 34.549 | 1.00 | 4.75 |
| ATOM | 21 | CD1 | ILE | 3 | -22.221 | 31.320 | 33.579 | 1.00 | 5.82 |
| ATOM | 22 | N | ILE | 4 | -26.319 | 28.814 | 31.563 | 1.00 | 7.21 |
| ATOM | 23 | CD1 | ILE | 4 | -26.578 | 27.854 | 27.424 | 1.00 | 8.61 |
| ATOM | 24 | CG1 | ILE | 4 | -27.102 | 28.463 | 28.794 | 1.00 | 8.70 |
| ATOM | 25 | CB | ILE | 4 | -27.272 | 27.363 | 29.888 | 1.00 | 7.20 |
| ATOM | 26 | CG2 | ILE | 4 | -28.446 | 26.419 | 29.544 | 1.00 | 6.35 |
| ATOM | 27 | CA | ILE | 4 | -27.569 | 28.083 | 31.259 | 1.00 | 7.04 |
| ATOM | 28 | C | ILE | 4 | -27.799 | 27.046 | 32.350 | 1.00 | 7.12 |
| ATOM | 29 | O | ILE | 4 | -26.841 | 26.414 | 32.764 | 1.00 | 5.80 |
| ATOM | 30 | N | GLY | 5 | -29.017 | 26.894 | 32.834 | 1.00 | 8.40 |
| ATOM | 31 | CA | GLY | 5 | -29.415 | 25.958 | 33.863 | 1.00 | 5.51 |
| ATOM | 32 | C | GLY | 5 | -29.031 | 24.550 | 33.483 | 1.00 | 6.74 |
| ATOM | 33 | O | GLY | 5 | -29.222 | 24.181 | 32.306 | 1.00 | 8.02 |
| ATOM | 34 | N | GLY | 6 | -28.492 | 23.787 | 34.436 | 1.00 | 5.32 |
| ATOM | 35 | CA | GLY | 6 | -28.113 | 22.385 | 34.125 | 1.00 | 6.51 |
| ATOM | 36 | C | GLY | 6 | -26.697 | 22.143 | 33.678 | 1.00 | 7.67 |
| ATOM | 37 | O | GLY | 6 | -26.264 | 20.957 | 33.687 | 1.00 | 8.08 |
| ATOM | 38 | N | LEU | 7 | -25.941 | 23.127 | 33.235 | 1.00 | 7.02 |
| ATOM | 39 | CD2 | LEU | 7 | -25.075 | 23.250 | 29.859 | 1.00 | 15.01 |
| ATOM | 40 | CD1 | LEU | 7 | -24.009 | 25.544 | 29.892 | 1.00 | 12.10 |
| ATOM | 41 | CG | LEU | 7 | -24.823 | 24.494 | 30.662 | 1.00 | 11.57 |
| ATOM | 42 | CB | LEU | 7 | -24.100 | 24.149 | 31.987 | 1.00 | 7.81 |
| ATOM | 43 | CA | LEU | 7 | -24.543 | 22.889 | 32.774 | 1.00 | 7.23 |
| ATOM | 44 | C | LEU | 7 | -23.543 | 22.624 | 33.891 | 1.00 | 8.17 |
| ATOM | 45 | O | LEU | 7 | -23.779 | 23.055 | 35.054 | 1.00 | 8.83 |
| ATOM | 46 | N | ALA | 8 | -22.450 | 21.931 | 33.560 | 1.00 | 7.85 |
| ATOM | 47 | CB | ALA | 8 | -20.568 | 20.517 | 33.998 | 1.00 | 7.20 |
| ATOM | 48 | CA | ALA | 8 | -21.436 | 21.658 | 34.583 | 1.00 | 6.67 |
| ATOM | 49 | C | ALA | 8 | -20.554 | 22.867 | 34.856 | 1.00 | 8.14 |
| ATOM | 50 | O | ALA | 8 | -20.241 | 23.793 | 34.058 | 1.00 | 7.62 |
| ATOM | 51 | N | TYR | 9 | -20.078 | 22.906 | 36.110 | 1.00 | 6.90 |
| ATOM | 52 | CA | TYR | 9 | -19.074 | 23.854 | 36.602 | 1.00 | 7.03 |
| ATOM | 53 | C | TYR | 9 | -18.138 | 22.960 | 37.480 | 1.00 | 8.21 |
| ATOM | 54 | O | TYR | 9 | -18.560 | 21.945 | 38.048 | 1.00 | 7.61 |

| | | | | | | | | |
|---|---|---|---|---|---|---|---|---|
| ATOM | 55 | CB | TYR | 9 | -19.474 | 25.108 | 37.320 | 1.00 7.45 |
| ATOM | 56 | CG | TYR | 9 | -20.138 | 24.925 | 38.664 | 1.00 9.14 |
| ATOM | 57 | CD1 | TYR | 9 | -19.401 | 24.898 | 39.853 | 1.00 8.86 |
| ATOM | 58 | CD2 | TYR | 9 | -21.559 | 24.818 | 38.673 | 1.00 8.66 |
| ATOM | 59 | CE1 | TYR | 9 | -20.044 | 24.756 | 41.062 | 1.00 7.11 |
| ATOM | 60 | CE2 | TYR | 9 | -22.214 | 24.696 | 39.930 | 1.00 8.78 |
| ATOM | 61 | CZ | TYR | 9 | -21.438 | 24.673 | 41.072 | 1.00 7.41 |
| ATOM | 62 | OH | TYR | 9 | -22.115 | 24.537 | 42.248 | 1.00 8.28 |
| ATOM | 63 | N | THR | 10 | -16.867 | 23.367 | 37.552 | 1.00 8.23 |
| ATOM | 64 | CG2 | THR | 10 | -15.380 | 21.144 | 36.171 | 1.00 21.51 |
| ATOM | 65 | OG1 | THR | 10 | -14.022 | 22.954 | 36.816 | 1.00 17.27 |
| ATOM | 66 | CB | THR | 10 | -14.816 | 21.869 | 37.398 | 1.00 15.54 |
| ATOM | 67 | CA | THR | 10 | -15.881 | 22.592 | 38.334 | 1.00 12.22 |
| ATOM | 68 | C | THR | 10 | -15.190 | 23.495 | 39.381 | 1.00 12.59 |
| ATOM | 69 | O | THR | 10 | -15.040 | 24.724 | 39.295 | 1.00 11.83 |
| ATOM | 70 | N | MET | 11 | -14.719 | 22.854 | 40.422 | 1.00 13.86 |
| ATOM | 71 | CE | MET | 11 | -18.117 | 21.521 | 42.992 | 0.70 10.20 |
| ATOM | 72 | SD | MET | 11 | -16.364 | 21.817 | 43.260 | 0.70 13.92 |
| ATOM | 73 | CG | MET | 11 | -16.351 | 23.607 | 42.742 | 0.70 8.87 |
| ATOM | 74 | CB | MET | 11 | -14.945 | 24.074 | 42.557 | 0.70 13.60 |
| ATOM | 79 | CA | MET | 11 | -14.003 | 23.423 | 41.576 | 1.00 14.74 |
| ATOM | 80 | C | MET | 11 | -13.204 | 22.219 | 42.141 | 1.00 16.84 |
| ATOM | 81 | O | MET | 11 | -13.132 | 22.126 | 43.360 | 1.00 18.29 |
| ATOM | 82 | N | GLY | 12 | -12.650 | 21.380 | 41.252 | 1.00 17.41 |
| ATOM | 83 | CA | GLY | 12 | -11.931 | 20.160 | 41.721 | 1.00 20.30 |
| ATOM | 84 | C | GLY | 12 | -12.961 | 19.034 | 41.377 | 1.00 22.00 |
| ATOM | 85 | O | GLY | 12 | -12.730 | 18.252 | 40.444 | 1.00 25.04 |
| ATOM | 86 | N | GLY | 13 | -14.079 | 19.064 | 42.126 | 1.00 17.68 |
| ATOM | 87 | CA | GLY | 13 | -15.219 | 18.171 | 41.900 | 1.00 15.21 |
| ATOM | 88 | C | GLY | 13 | -16.127 | 18.873 | 40.846 | 1.00 15.26 |
| ATOM | 89 | O | GLY | 13 | -15.681 | 19.862 | 40.228 | 1.00 14.61 |
| ATOM | 90 | N | ARG | 14 | -17.370 | 18.410 | 40.657 | 1.00 12.77 |
| ATOM | 91 | NH2 | ARG | 14 | -20.479 | 14.276 | 37.036 | 1.00 17.15 |
| ATOM | 92 | NH1 | ARG | 14 | -21.587 | 16.075 | 36.340 | 1.00 13.21 |
| ATOM | 93 | CZ | ARG | 14 | -20.415 | 15.529 | 36.584 | 1.00 16.51 |
| ATOM | 94 | NE | ARG | 14 | -19.265 | 16.236 | 36.423 | 1.00 15.10 |
| ATOM | 95 | CD | ARG | 14 | -19.240 | 17.643 | 36.031 | 1.00 15.25 |
| ATOM | 96 | CG | ARG | 14 | -19.255 | 18.517 | 37.291 | 1.00 14.76 |
| ATOM | 97 | CB | ARG | 14 | -18.333 | 18.056 | 38.435 | 1.00 11.53 |
| ATOM | 98 | CA | ARG | 14 | -18.269 | 19.018 | 39.659 | 1.00 11.00 |
| ATOM | 99 | C | ARG | 14 | -19.665 | 19.162 | 40.278 | 1.00 9.52 |
| ATOM | 100 | O | ARG | 14 | -20.027 | 18.274 | 41.091 | 1.00 8.13 |
| ATOM | 101 | N | CYS | 15 | -20.368 | 20.221 | 39.853 | 1.00 8.85 |
| ATOM | 102 | CA | CYS | 15 | -21.782 | 20.417 | 40.285 | 1.00 6.14 |
| ATOM | 103 | C | CYS | 15 | -22.455 | 21.027 | 39.084 | 1.00 6.53 |
| ATOM | 104 | O | CYS | 15 | -21.754 | 21.176 | 38.036 | 1.00 8.10 |
| ATOM | 105 | CB | CYS | 15 | -21.897 | 21.271 | 41.568 | 1.00 7.27 |
| ATOM | 106 | SG | CYS | 15 | -21.795 | 20.241 | 43.088 | 1.00 8.70 |
| ATOM | 107 | N | SER | 16 | -23.746 | 21.368 | 39.154 | 1.00 5.13 |
| ATOM | 108 | CA | SER | 16 | -24.402 | 21.936 | 37.975 | 1.00 4.73 |
| ATOM | 109 | C | SER | 16 | -24.969 | 23.294 | 38.269 | 1.00 6.73 |
| ATOM | 110 | O | SER | 16 | -25.331 | 23.536 | 39.470 | 1.00 7.15 |
| ATOM | 111 | CB | SER | 16 | -25.540 | 20.930 | 37.602 | 1.00 5.02 |
| ATOM | 112 | OG | SER | 16 | -25.031 | 19.670 | 37.228 | 1.00 7.01 |

```
ATOM    113  N    VAL   17     -25.177  24.129  37.276  1.00   5.71
ATOM    114  CA   VAL   17     -25.780  25.469  37.450  1.00   6.30
ATOM    115  C    VAL   17     -27.274  25.365  37.742  1.00   6.27
ATOM    116  O    VAL   17     -27.904  24.514  37.084  1.00   6.87
ATOM    117  CB   VAL   17     -25.589  26.211  36.113  1.00   4.80
ATOM    118  CG1  VAL   17     -26.252  27.572  36.079  1.00   2.00
ATOM    119  CG2  VAL   17     -24.108  26.435  35.892  1.00   5.56
ATOM    120  N    GLY   18     -27.836  26.136  38.622  1.00   5.84
ATOM    121  CA   GLY   18     -29.277  26.067  38.899  1.00   4.89
ATOM    122  C    GLY   18     -29.898  27.072  37.958  1.00   7.79
ATOM    123  O    GLY   18     -30.578  26.683  36.960  1.00   8.56
ATOM    124  N    PHE   19     -29.783  28.366  38.175  1.00   6.84
ATOM    125  CA   PHE   19     -30.368  29.391  37.291  1.00   8.35
ATOM    126  C    PHE   19     -29.457  30.625  37.254  1.00   8.67
ATOM    127  O    PHE   19     -28.889  30.984  38.285  1.00   7.20
ATOM    128  CB   PHE   19     -31.761  29.873  37.827  1.00   6.74
ATOM    129  CG   PHE   19     -32.786  28.779  38.033  1.00   8.40
ATOM    130  CD1  PHE   19     -33.490  28.300  36.918  1.00   9.81
ATOM    131  CD2  PHE   19     -32.921  28.194  39.301  1.00   8.27
ATOM    132  CE1  PHE   19     -34.414  27.241  37.060  1.00   7.45
ATOM    133  CE2  PHE   19     -33.804  27.129  39.460  1.00   7.36
ATOM    134  CZ   PHE   19     -34.541  26.662  38.347  1.00   8.66
ATOM    135  N    ALA   20     -29.375  31.284  36.114  1.00   8.32
ATOM    136  CB   ALA   20     -28.552  32.954  34.501  1.00   7.08
ATOM    137  CA   ALA   20     -28.577  32.514  35.976  1.00   6.99
ATOM    138  C    ALA   20     -29.347  33.558  36.793  1.00   8.39
ATOM    139  O    ALA   20     -30.614  33.548  36.744  1.00   6.62
ATOM    140  N    ALA   21     -28.653  34.461  37.453  1.00   6.45
ATOM    141  CB   ALA   21     -29.774  34.943  39.600  1.00   6.04
ATOM    142  CA   ALA   21     -29.305  35.514  38.244  1.00   9.09
ATOM    143  C    ALA   21     -28.267  36.598  38.599  1.00  10.25
ATOM    144  O    ALA   21     -27.048  36.412  38.434  1.00  10.39
ATOM    145  N    THR   22     -28.734  37.704  39.154  1.00  10.87
ATOM    146  CA   THR   22     -27.795  38.747  39.633  1.00   9.81
ATOM    147  C    THR   22     -28.044  38.773  41.139  1.00  12.70
ATOM    148  O    THR   22     -29.153  38.378  41.607  1.00  13.28
ATOM    149  CB   THR   22     -28.009  40.191  39.000  1.00  12.32
ATOM    150  OG1  THR   22     -29.443  40.520  39.201  1.00  17.96
ATOM    151  CG2  THR   22     -27.730  40.314  37.512  1.00  10.22
ATOM    152  N    ASN   23     -27.067  39.261  41.919  1.00  12.56
ATOM    153  ND2  ASN   23     -23.651  39.789  44.187  1.00  14.15
ATOM    154  OD1  ASN   23     -25.034  41.090  43.182  1.00  11.99
ATOM    155  CG   ASN   23     -24.917  40.044  43.825  1.00  13.60
ATOM    156  CB   ASN   23     -26.025  39.065  44.153  1.00  12.41
ATOM    157  CA   ASN   23     -27.308  39.367  43.381  1.00  14.31
ATOM    158  C    ASN   23     -27.947  40.754  43.600  1.00  15.71
ATOM    159  O    ASN   23     -28.252  41.558  42.664  1.00  13.68
ATOM    160  N    ALA   24     -28.043  41.088  44.883  1.00  16.68
ATOM    161  CB   ALA   24     -28.899  42.370  46.862  1.00  19.20
ATOM    162  CA   ALA   24     -28.626  42.344  45.371  1.00  20.06
ATOM    163  C    ALA   24     -27.831  43.543  44.936  1.00  22.43
ATOM    164  O    ALA   24     -28.408  44.658  44.795  1.00  24.93
ATOM    165  N    ALA   25     -26.556  43.412  44.648  1.00  23.59
ATOM    166  CA   ALA   25     -25.727  44.513  44.128  1.00  20.79
```

```
ATOM    167  C    ALA  25     -25.765  44.542  42.613  1.00  21.34
ATOM    168  O    ALA  25     -25.018  45.388  42.040  1.00  24.26
ATOM    169  CB   ALA  25     -24.278  44.379  44.584  1.00  24.28'
ATOM    170  N    GLY  26     -26.508  43.687  41.910  1.00  16.97
ATOM    171  CA   GLY  26     -26.453  43.763  40.456  1.00  15.31
ATOM    172  C    GLY  26     -25.320  43.024  39.803  1.00  13.98
ATOM    173  O    GLY  26     -25.158  43.168  38.560  1.00  15.90
ATOM    174  N    GLN  27     -24.594  42.196  40.523  1.00  13.26
ATOM    175  NE2  GLN  27     -19.688  42.607  42.319  1.00  23.84
ATOM    176  OE1  GLN  27     -21.306  41.674  43.669  1.00  19.08
ATOM    177  CD   GLN  27     -20.952  42.234  42.626  1.00  20.42
ATOM    178  CG   GLN  27     -21.934  42.487  41.519  1.00  16.87
ATOM    179  CB   GLN  27     -22.364  41.130  40.909  1.00  13.66
ATOM    180  CA   GLN  27     -23.488  41.430  39.904  1.00  11.98
ATOM    181  C    GLN  27     -24.023  40.113  39.345  1.00  11.67
ATOM    182  O    GLN  27     -24.829  39.428  39.949  1.00  11.63
ATOM    183  N    PRO  28     -23.539  39.714  38.197  1.00  10.36
ATOM    184  CG   PRO  28     -22.111  39.444  36.367  1.00  11.95
ATOM    185  CD   PRO  28     -22.544  40.519  37.403  1.00  10.61
ATOM    186  CB   PRO  28     -23.429  38.692  36.116  1.00  11.06
ATOM    187  CA   PRO  28     -23.977  38.497  37.537  1.00   9.08
ATOM    188  C    PRO  28     -23.418  37.248  38.194  1.00   9.80
ATOM    189  O    PRO  28     -22.278  37.282  38.749  1.00   9.50
ATOM    190  N    GLY  29     -24.245  36.179  38.101  1.00   6.29
ATOM    191  CA   GLY  29     -23.721  34.885  38.671  1.00   4.48
ATOM    192  C    GLY  29     -24.827  33.875  38.440  1.00   6.36
ATOM    193  O    GLY  29     -25.604  34.036  37.454  1.00   7.58
ATOM    194  N    PHE  30     -24.889  32.917  39.339  1.00   7.28
ATOM    195  CA   PHE  30     -25.971  31.891  39.292  1.00   7.77
ATOM    196  C    PHE  30     -26.232  31.306  40.703  1.00   6.83
ATOM    197  O    PHE  30     -25.281  31.334  41.532  1.00   8.49
ATOM    198  CB   PHE  30     -25.653  30.741  38.312  1.00   3.78
ATOM    199  CG   PHE  30     -24.384  29.955  38.483  1.00   5.51
ATOM    200  CD1  PHE  30     -24.299  28.836  39.311  1.00   5.54
ATOM    201  CD2  PHE  30     -23.251  30.336  37.752  1.00   8.26
ATOM    202  CE1  PHE  30     -23.126  28.108  39.451  1.00   8.21
ATOM    203  CE2  PHE  30     -21.996  29.661  37.898  1.00   6.20
ATOM    204  CZ   PHE  30     -21.971  28.509  38.739  1.00   7.61
ATOM    205  N    VAL  31     -27.413  30.739  40.862  1.00   4.85
ATOM    206  CA   VAL  31     -27.751  30.017  42.118  1.00   6.26
ATOM    207  C    VAL  31     -27.445  28.530  41.828  1.00   6.68
ATOM    208  O    VAL  31     -27.515  28.036  40.680  1.00   4.79
ATOM    209  CB   VAL  31     -29.141  30.296  42.666  1.00   7.03
ATOM    210  CG1  VAL  31     -29.230  31.765  43.136  1.00  11.46
ATOM    211  CG2  VAL  31     -30.190  29.902  41.646  1.00   8.54
ATOM    212  N    THR  32     -27.150  27.786  42.910  1.00   5.51
ATOM    213  CA   THR  32     -26.762  26.373  42.892  1.00   7.30
ATOM    214  C    THR  32     -26.833  25.866  44.356  1.00   8.85
ATOM    215  O    THR  32     -27.382  26.568  45.240  1.00   6.58
ATOM    216  CB   THR  32     -25.318  26.271  42.249  1.00   6.85
ATOM    217  OG1  THR  32     -24.927  24.904  42.030  1.00   6.22
ATOM    218  CG2  THR  32     -24.141  26.895  43.109  1.00   4.90
ATOM    219  N    ALA  33     -26.318  24.676  44.619  1.00   8.92
ATOM    220  CA   ALA  33     -26.313  24.007  45.928  1.00   9.53
```

```
ATOM    221  C    ALA   33     -25.158  24.465  46.827  1.00   9.16
ATOM    222  O    ALA   33     -24.007  24.503  46.369  1.00   8.53
ATOM    223  CB   ALA   33     -26.294  22.473  45.773  1.00   7.77
ATOM    224  N    GLY   34     -25.408  24.724  48.076  1.00   7.16
ATOM    225  CA   GLY   34     -24.348  25.143  49.024  1.00   8.05
ATOM    226  C    GLY   34     -23.390  24.043  49.347  1.00   7.39
ATOM    227  O    GLY   34     -22.194  24.315  49.698  1.00   8.30
ATOM    228  N    HIS   35     -23.788  22.780  49.271  1.00   7.52
ATOM    229  CA   HIS   35     -22.821  21.714  49.636  1.00   6.58
ATOM    230  C    HIS   35     -21.744  21.601  48.560  1.00   8.95
ATOM    231  O    HIS   35     -20.702  20.945  48.747  1.00   8.96
ATOM    232  CB   HIS   35     -23.497  20.364  49.883  1.00   8.85
ATOM    233  CG   HIS   35     -23.991  19.599  48.686  1.00   6.87
ATOM    234  ND1  HIS   35     -25.305  19.481  48.321  1.00   8.56
ATOM    235  CD2  HIS   35     -23.326  18.872  47.769  1.00   5.55
ATOM    236  CE1  HIS   35     -25.414  18.744  47.228  1.00   7.54
ATOM    237  NE2  HIS   35     -24.217  18.313  46.906  1.00   8.64
ATOM    238  N    CYS   36     -21.930  22.183  47.376  1.00   8.15
ATOM    239  CA   CYS   36     -20.940  22.145  46.312  1.00   8.05
ATOM    240  C    CYS   36     -19.746  23.062  46.679  1.00  11.13
ATOM    241  O    CYS   36     -18.715  22.841  45.999  1.00  10.34
ATOM    242  CB   CYS   36     -21.518  22.598  44.977  1.00   5.97
ATOM    243  SG   CYS   36     -22.774  21.389  44.403  1.00   9.16
ATOM    244  N    GLY   37     -19.855  24.012  47.601  1.00   9.60
ATOM    245  CA   GLY   37     -18.632  24.821  47.862  1.00   8.52
ATOM    246  C    GLY   37     -18.853  25.793  48.998  1.00  11.72
ATOM    247  O    GLY   37     -19.923  26.350  49.153  1.00  12.57
ATOM    248  N    ARG   38     -17.807  26.044  49.767  1.00   9.44
ATOM    249  NH2  ARG   38     -13.066  27.478  54.730  0.00  41.69
ATOM    250  NH1  ARG   38     -14.258  25.862  55.765  0.00  42.03
ATOM    251  CZ   ARG   38     -13.968  26.494  54.619  0.00  41.38
ATOM    252  NE   ARG   38     -14.559  26.142  53.467  0.00  39.87
ATOM    253  CD   ARG   38     -15.763  25.165  53.320  0.00  37.50
ATOM    254  CG   ARG   38     -17.064  25.666  52.814  1.00  23.13
ATOM    255  CB   ARG   38     -16.602  26.727  51.799  1.00  14.90
ATOM    256  CA   ARG   38     -17.812  27.040  50.845  1.00  12.65
ATOM    257  C    ARG   38     -17.566  28.415  50.239  1.00  11.84
ATOM    258  O    ARG   38     -16.987  28.562  49.137  1.00  10.80
ATOM    259  N    VAL   39     -17.953  29.488  50.953  1.00  12.22
ATOM    260  CA   VAL   39     -17.723  30.881  50.483  1.00  11.55
ATOM    261  C    VAL   39     -16.224  31.002  50.149  1.00  11.46
ATOM    262  O    VAL   39     -15.406  30.540  50.944  1.00  12.65
ATOM    263  CB   VAL   39     -18.195  31.902  51.513  1.00  14.37
ATOM    264  CG1  VAL   39     -17.541  33.262  51.282  1.00  18.26
ATOM    265  CG2  VAL   39     -19.720  32.035  51.617  1.00  19.01
ATOM    266  N    GLY   40     -15.853  31.595  49.017  1.00  10.59
ATOM    267  CA   GLY   40     -14.467  31.715  48.658  1.00   9.21
ATOM    268  C    GLY   40     -13.962  30.690  47.689  1.00  11.61
ATOM    269  O    GLY   40     -12.904  30.954  47.066  1.00  13.99
ATOM    270  N    THR   41     -14.603  29.592  47.441  1.00  10.26
ATOM    271  CG2  THR   41     -14.886  26.180  45.550  1.00   8.90
ATOM    272  OG1  THR   41     -15.058  26.792  47.930  1.00  14.49
ATOM    273  CB   THR   41     -15.123  27.285  46.571  1.00  12.41
ATOM    274  CA   THR   41     -14.199  28.566  46.525  1.00   9.98
```

```
ATOM    275  C    THR    41     -14.360  29.148  45.121  1.00  11.13
ATOM    276  O    THR    41     -15.404  29.657  44.713  1.00  10.17
ATOM    277  N    GLN    42     -13.297  28.983  44.365  1.00  12.36
ATOM    278  NE2  GLN    42     -11.317  32.840  43.178  0.70  32.68
ATOM    279  OE1  GLN    42      -9.407  31.714  42.552  0.70  35.48
ATOM    280  CD   GLN    42     -10.512  31.791  43.080  0.70  30.29
ATOM    281  CG   GLN    42     -11.132  30.558  43.680  0.70  24.69
ATOM    282  CB   GLN    42     -11.801  29.729  42.592  0.70  18.80
ATOM    288  CA   GLN    42     -13.263  29.456  42.977  1.00  11.77
ATOM    289  C    GLN    42     -13.852  28.392  42.063  1.00  13.86
ATOM    290  O    GLN    42     -13.615  27.187  42.330  1.00  12.07
ATOM    291  N    VAL    43     -14.544  28.817  41.002  1.00  13.96
ATOM    292  CG2  VAL    43     -17.397  28.751  39.309  1.00  15.91
ATOM    293  CG1  VAL    43     -17.192  27.656  41.542  1.00  10.29
ATOM    294  CB   VAL    43     -16.657  27.731  40.117  1.00  14.08
ATOM    295  CA   VAL    43     -15.132  27.886  40.018  1.00  11.05
ATOM    296  C    VAL    43     -14.717  28.297  38.584  1.00  10.70
ATOM    297  O    VAL    43     -14.393  29.467  38.214  1.00   8.75
ATOM    298  N    THR    44     -14.726  27.266  37.757  1.00   8.19
ATOM    299  CG2  THR    44     -13.085  26.655  34.277  1.00  16.80
ATOM    300  OG1  THR    44     -12.054  27.080  36.423  1.00  14.72
ATOM    301  CB   THR    44     -13.232  26.536  35.773  1.00   7.96
ATOM    302  CA   THR    44     -14.459  27.387  36.328  1.00   8.95
ATOM    303  C    THR    44     -15.708  26.877  35.588  1.00  10.78
ATOM    304  O    THR    44     -16.155  25.743  35.947  1.00   9.00
ATOM    305  N    ILE    45     -16.219  27.660  34.626  1.00  10.77
ATOM    306  CA   ILE    45     -17.352  27.175  33.850  1.00  11.78
ATOM    307  C    ILE    45     -16.950  27.476  32.396  1.00  10.56
ATOM    308  O    ILE    45     -16.976  28.673  32.030  1.00  10.62
ATOM    309  CB   ILE    45     -18.743  27.767  34.312  1.00   8.73
ATOM    310  CG1  ILE    45     -19.767  27.359  33.217  1.00  14.25
ATOM    311  CG2  ILE    45     -18.635  29.300  34.483  1.00  14.91
ATOM    312  CD1  ILE    45     -21.239  27.351  33.717  1.00  17.74
ATOM    313  N    GLY    46     -16.588  26.493  31.623  1.00  11.49
ATOM    314  CA   GLY    46     -16.162  26.796  30.214  1.00  13.72
ATOM    315  C    GLY    46     -15.009  27.812  30.282  1.00  12.34
ATOM    316  O    GLY    46     -14.011  27.661  31.002  1.00  14.15
ATOM    317  N    ASN    47     -15.134  28.895  29.512  1.00  13.14
ATOM    318  ND2  ASN    47     -15.075  31.342  26.221  1.00  26.89
ATOM    319  OD1  ASN    47     -16.257  31.266  28.086  1.00  18.12
ATOM    320  CG   ASN    47     -15.180  31.045  27.520  1.00  19.67
ATOM    321  CB   ASN    47     -13.914  30.476  28.081  1.00  17.20
ATOM    322  CA   ASN    47     -14.106  29.967  29.522  1.00  14.86
ATOM    323  C    ASN    47     -14.409  31.129  30.484  1.00  14.20
ATOM    324  O    ASN    47     -13.929  32.264  30.367  1.00  16.69
ATOM    325  N    GLY    48     -15.234  30.900  31.476  1.00  11.79
ATOM    326  CA   GLY    48     -15.629  31.860  32.487  1.00  10.60
ATOM    327  C    GLY    48     -15.114  31.350  33.840  1.00   8.68
ATOM    328  O    GLY    48     -14.741  30.180  34.021  1.00   8.85
ATOM    329  N    ARG    49     -15.067  32.286  34.782  1.00   8.71
ATOM    330  NH2  ARG    49     -10.753  29.684  38.714  0.00  43.61
ATOM    331  NH1  ARG    49      -9.430  30.717  37.086  0.00  39.51
ATOM    332  CZ   ARG    49     -10.647  30.223  37.466  0.00  42.12
ATOM    333  NE   ARG    49     -11.803  30.174  36.714  0.00  38.98
```

```
ATOM    334  CD  ARG    49     -11.625  30.774  35.625  1.00 24.44
ATOM    335  CG  ARG    49     -12.079  32.161  35.395  1.00 20.17
ATOM    336  CB  ARG    49     -13.190  32.537  36.355  1.00 13.15
ATOM    337  CA  ARG    49     -14.600  31.985  36.143  1.00  8.87
ATOM    338  C   ARG    49     -15.485  32.746  37.136  1.00  9.56
ATOM    339  O   ARG    49     -16.026  33.814  36.747  1.00 10.73
ATOM    340  N   GLY    50     -15.644  32.236  38.337  1.00 10.04
ATOM    341  CA  GLY    50     -16.416  32.933  39.372  1.00  6.68
ATOM    342  C   GLY    50     -15.985  32.438  40.758  1.00  7.46
ATOM    343  O   GLY    50     -15.035  31.654  40.838  1.00  8.57
ATOM    344  N   VAL    51     -16.755  32.885  41.756  1.00  9.13
ATOM    345  CG2 VAL    51     -15.047  33.181  45.219  1.00  9.31
ATOM    346  CG1 VAL    51     -16.041  34.936  43.760  1.00  9.54
ATOM    347  CB  VAL    51     -15.469  33.510  43.768  1.00 10.40
ATOM    348  CA  VAL    51     -16.439  32.474  43.145  1.00  8.97
ATOM    349  C   VAL    51     -17.739  32.363  43.951  1.00  8.46
ATOM    350  O   VAL    51     -18.657  33.166  43.726  1.00  8.01
ATOM    351  N   PHE    52     -17.778  31.394  44.846  1.00  7.71
ATOM    352  CD2 PHE    52     -20.510  28.198  46.287  1.00  7.34
ATOM    353  CE2 PHE    52     -20.952  27.038  45.614  1.00 12.48
ATOM    354  CZ  PHE    52     -20.103  26.415  44.672  1.00 11.92
ATOM    355  CE1 PHE    52     -18.857  26.983  44.355  1.00  8.56
ATOM    356  CD1 PHE    52     -18.454  28.151  45.012  1.00  7.30
ATOM    357  CG  PHE    52     -19.269  28.765  45.964  1.00 10.46
ATOM    358  CB  PHE    52     -18.820  30.015  46.703  1.00  9.22
ATOM    359  CA  PHE    52     -18.916  31.237  45.766  1.00  9.28
ATOM    360  C   PHE    52     -18.928  32.498  46.637  1.00 10.41
ATOM    361  O   PHE    52     -17.979  32.752  47.403  1.00 10.33
ATOM    362  N   GLU    53     -20.038  33.239  46.481  1.00  8.81
ATOM    363  OE2 GLU    53     -22.012  37.756  45.426  1.00 27.06
ATOM    364  OE1 GLU    53     -21.229  39.265  46.722  1.00 33.78
ATOM    365  CD  GLU    53     -21.338  38.087  46.413  1.00 28.63
ATOM    366  CG  GLU    53     -20.701  36.961  47.162  1.00 15.08
ATOM    367  CB  GLU    53     -20.818  35.612  46.441  1.00 10.91
ATOM    368  CA  GLU    53     -20.172  34.475  47.239  1.00 10.55
ATOM    369  C   GLU    53     -21.035  34.208  48.485  1.00 13.01
ATOM    370  O   GLU    53     -20.664  34.743  49.558  1.00 11.89
ATOM    371  N   GLN    54     -22.095  33.444  48.352  1.00  9.12
ATOM    372  NE2 GLN    54     -26.256  36.329  49.251  1.00 43.84
ATOM    373  OE1 GLN    54     -25.933  35.594  51.419  1.00 46.53
ATOM    374  CD  GLN    54     -25.586  35.741  50.241  1.00 40.72
ATOM    375  CG  GLN    54     -24.256  35.205  49.756  1.00 29.81
ATOM    376  CB  GLN    54     -24.346  33.707  49.555  1.00 17.82
ATOM    377  CA  GLN    54     -22.955  33.105  49.508  1.00 10.81
ATOM    378  C   GLN    54     -23.164  31.600  49.527  1.00 12.82
ATOM    379  O   GLN    54     -23.418  31.101  48.410  1.00 13.75
ATOM    380  N   SER    55     -23.074  30.926  50.665  1.00 10.56
ATOM    381  OG  SER    55     -22.169  27.372  50.204  1.00 14.02
ATOM    382  CB  SER    55     -21.995  28.781  50.228  1.00  9.88
ATOM    383  CA  SER    55     -23.280  29.470  50.637  1.00 11.20
ATOM    384  C   SER    55     -23.730  28.998  52.014  1.00 12.70
ATOM    385  O   SER    55     -23.084  29.298  53.011  1.00 11.84
ATOM    386  N   VAL    56     -24.824  28.274  52.086  1.00 11.38
ATOM    387  CA  VAL    56     -25.345  27.735  53.342  1.00  9.56
```

```
ATOM    388  C   VAL    56     -25.516  26.223  53.218  1.00  11.47
ATOM    389  O   VAL    56     -26.250  25.756  52.302  1.00  10.80
ATOM    390  CB  VAL    56     -26.691  28.365  53.715  1.00  12.57
ATOM    391  CG1 VAL    56     -27.250  27.561  54.895  1.00  13.65
ATOM    392  CG2 VAL    56     -26.542  29.809  54.111  1.00  14.61
ATOM    393  N   PHE    57     -24.903  25.475  54.116  1.00   9.44
ATOM    394  CA  PHE    57     -25.035  24.030  54.173  1.00  10.86
ATOM    395  C   PHE    57     -24.351  23.597  55.503  1.00  12.68
ATOM    396  O   PHE    57     -23.200  24.057  55.632  1.00  14.31
ATOM    397  CB  PHE    57     -24.383  23.289  52.962  1.00   9.20
ATOM    398  CG  PHE    57     -24.530  21.797  53.071  1.00   7.41
ATOM    399  CD1 PHE    57     -23.489  20.999  53.547  1.00  10.87
ATOM    400  CD2 PHE    57     -25.748  21.211  52.762  1.00  10.76
ATOM    401  CE1 PHE    57     -23.654  19.621  53.690  1.00  16.75
ATOM    402  CE2 PHE    57     -25.948  19.851  52.869  1.00   9.80
ATOM    403  CZ  PHE    57     -24.897  19.033  53.326  1.00  17.07
ATOM    404  N   PRO    58     -24.888  22.759  56.355  1.00  11.76
ATOM    405  CA  PRO    58     -26.182  22.082  56.294  1.00  11.15
ATOM    406  C   PRO    58     -27.302  22.967  56.755  1.00   9.63
ATOM    407  O   PRO    58     -27.072  24.207  56.657  1.00  10.82
ATOM    408  CB  PRO    58     -25.955  20.768  57.043  1.00  11.03
ATOM    409  CG  PRO    58     -24.947  21.178  58.078  1.00  12.71
ATOM    410  CD  PRO    58     -24.125  22.322  57.531  1.00  12.73
ATOM    411  N   GLY    59     -28.466  22.432  57.103  1.00  10.97
ATOM    412  CA  GLY    59     -29.594  23.338  57.495  1.00  11.26
ATOM    413  C   GLY    59     -30.330  23.680  56.200  1.00  10.98
ATOM    414  O   GLY    59     -31.477  23.240  56.091  1.00  11.30
ATOM    415  N   ASN    60     -29.767  24.482  55.291  1.00  10.66
ATOM    416  CA  ASN    60     -30.400  24.729  53.962  1.00   8.17
ATOM    417  C   ASN    60     -29.377  24.099  52.981  1.00   9.56
ATOM    418  O   ASN    60     -28.346  23.532  53.474  1.00   8.76
ATOM    419  CB  ASN    60     -30.598  26.175  53.595  1.00   9.50
ATOM    420  CG  ASN    60     -31.369  26.934  54.664  1.00  12.19
ATOM    421  OD1 ASN    60     -30.872  27.984  55.082  1.00  16.81
ATOM    422  ND2 ASN    60     -32.478  26.340  55.060  1.00  15.11
ATOM    423  N   ASP    61     -29.582  24.193  51.661  1.00   7.15
ATOM    424  CA  ASP    61     -28.544  23.661  50.701  1.00   7.83
ATOM    425  C   ASP    61     -28.598  24.692  49.547  1.00   8.69
ATOM    426  O   ASP    61     -29.213  24.393  48.519  1.00   7.71
ATOM    427  CB  ASP    61     -28.818  22.216  50.313  1.00   4.48
ATOM    428  CG  ASP    61     -27.637  21.575  49.640  1.00   6.18
ATOM    429  OD1 ASP    61     -27.591  20.419  49.245  1.00   6.86
ATOM    430  OD2 ASP    61     -26.622  22.316  49.431  1.00   8.20
ATOM    431  N   ALA    62     -28.041  25.868  49.751  1.00   7.72
ATOM    432  CB  ALA    62     -29.258  27.857  49.385  1.00   8.64
ATOM    433  CA  ALA    62     -28.134  26.967  48.775  1.00   8.98
ATOM    434  C   ALA    62     -26.880  27.802  48.618  1.00   9.19
ATOM    435  O   ALA    62     -26.114  27.939  49.618  1.00  10.25
ATOM    436  N   ALA    63     -26.667  28.360  47.434  1.00   7.69
ATOM    437  CA  ALA    63     -25.476  29.189  47.173  1.00   7.50
ATOM    438  C   ALA    63     -25.668  30.110  45.987  1.00   7.33
ATOM    439  O   ALA    63     -26.526  29.843  45.116  1.00   6.36
ATOM    440  CB  ALA    63     -24.247  28.263  46.886  1.00   4.57
ATOM    441  N   PHE    64     -24.889  31.172  45.985  1.00   8.23
```

```
ATOM    442  CD2 PHE    64     -24.221  35.364  43.942  1.00   6.73
ATOM    443  CE2 PHE    64     -24.051  36.237  42.841  1.00   7.23
ATOM    444  CZ  PHE    64     -25.063  36.205  41.842  1.00   6.08
ATOM    445  CE1 PHE    64     -26.166  35.352  41.959  1.00  10.30
ATOM    446  CD1 PHE    64     -26.263  34.453  43.038  1.00  10.04
ATOM    447  CG  PHE    64     -25.287  34.477  44.027  1.00   6.69
ATOM    448  CB  PHE    64     -25.415  33.537  45.240  1.00   6.42
ATOM    449  CA  PHE    64     -24.840  32.152  44.922  1.00   7.87
ATOM    450  C   PHE    64     -23.351  32.196  44.518  1.00  10.06
ATOM    451  O   PHE    64     -22.454  32.478  45.362  1.00  10.39
ATOM    452  N   VAL    65     -23.080  31.952  43.234  1.00   8.61
ATOM    453  CA  VAL    65     -21.722  32.028  42.662  1.00   8.62
ATOM    454  C   VAL    65     -21.686  33.327  41.831  1.00   8.89
ATOM    455  O   VAL    65     -22.514  33.548  40.948  1.00   7.44
ATOM    456  CB  VAL    65     -21.338  30.840  41.722  1.00  11.34
ATOM    457  CG1 VAL    65     -20.018  31.055  40.967  1.00  10.37
ATOM    458  CG2 VAL    65     -21.333  29.530  42.493  1.00   9.94
ATOM    459  N   ARG    66     -20.744  34.213  42.094  1.00   6.55
ATOM    460  NH2 ARG    66     -16.111  39.098  43.470  1.00  18.29
ATOM    461  NH1 ARG    66     -17.309  39.979  41.747  1.00  18.67
ATOM    462  CZ  ARG    66     -17.271  39.260  42.832  1.00  18.74
ATOM    463  NE  ARG    66     -18.308  38.673  43.409  1.00  22.97
ATOM    464  CD  ARG    66     -19.672  38.751  42.950  1.00  23.13
ATOM    465  CG  ARG    66     -19.916  37.827  41.797  1.00  18.33
ATOM    466  CB  ARG    66     -19.949  36.464  42.422  1.00  12.11
ATOM    467  CA  ARG    66     -20.545  35.475  41.416  1.00   8.00
ATOM    468  C   ARG    66     -19.501  35.310  40.305  1.00   7.85
ATOM    469  O   ARG    66     -18.447  34.738  40.557  1.00   8.51
ATOM    470  N   GLY    67     -19.828  35.857  39.132  1.00   8.23
ATOM    471  CA  GLY    67     -18.921  35.779  37.962  1.00   3.28
ATOM    472  C   GLY    67     -17.838  36.834  38.114  1.00   7.11
ATOM    473  O   GLY    67     -18.123  38.019  38.332  1.00   9.23
ATOM    474  N   THR    68     -16.585  36.418  37.933  1.00   6.19
ATOM    475  CA  THR    68     -15.407  37.292  37.994  1.00   6.13
ATOM    476  C   THR    68     -14.784  37.468  36.611  1.00  10.55
ATOM    477  O   THR    68     -13.939  38.358  36.375  1.00   9.20
ATOM    478  CB  THR    68     -14.366  36.832  39.071  1.00  13.02
ATOM    479  OG1 THR    68     -13.865  35.569  38.579  1.00   9.29
ATOM    480  CG2 THR    68     -14.870  36.773  40.522  1.00  11.87
ATOM    481  N   SER    69     -15.205  36.672  35.618  1.00  12.02
ATOM    482  CA  SER    69     -14.736  36.796  34.233  1.00  11.62
ATOM    483  C   SER    69     -15.660  36.069  33.264  1.00  12.37
ATOM    484  O   SER    69     -15.911  34.865  33.480  1.00  11.23
ATOM    485  CB  SER    69     -13.337  36.184  34.027  1.00  12.32
ATOM    486  OG  SER    69     -12.823  36.389  32.763  1.00  15.07
ATOM    487  N   ASN    70     -16.100  36.767  32.236  1.00  12.58
ATOM    488  ND2 ASN    70     -16.685  36.201  28.330  1.00  20.03
ATOM    489  OD1 ASN    70     -15.425  34.370  28.194  1.00  19.07
ATOM    490  CG  ASN    70     -15.954  35.243  28.878  1.00  14.54
ATOM    491  CB  ASN    70     -15.848  35.335  30.379  1.00   8.27
ATOM    492  CA  ASN    70     -16.894  36.195  31.131  1.00  11.17
ATOM    493  C   ASN    70     -18.166  35.424  31.400  1.00  10.53
ATOM    494  O   ASN    70     -18.343  34.319  30.817  1.00  14.17
ATOM    495  N   PHE    71     -19.048  35.946  32.209  1.00   8.98
```

```
ATOM    496  CD2 PHE    71     -21.139  34.054  36.002  1.00   5.72
ATOM    497  CE2 PHE    71     -20.735  33.063  36.900  1.00   7.44
ATOM    498  CZ  PHE    71     -19.483  32.395  36.669  1.00  10.35
ATOM    499  CE1 PHE    71     -18.713  32.681  35.550  1.00  10.41
ATOM    500  CD1 PHE    71     -19.159  33.681  34.652  1.00   9.67
ATOM    501  CG  PHE    71     -20.350  34.372  34.873  1.00   5.76
ATOM    502  CB  PHE    71     -20.839  35.417  33.897  1.00   7.11
ATOM    503  CA  PHE    71     -20.346  35.257  32.435  1.00  10.26
ATOM    504  C   PHE    71     -21.337  35.958  31.503  1.00  11.61
ATOM    505  O   PHE    71     -21.429  37.207  31.537  1.00  14.68
ATOM    506  N   THR    72     -22.071  35.275  30.691  1.00  11.03
ATOM    507  CA  THR    72     -23.133  35.902  29.860  1.00   9.26
ATOM    508  C   THR    72     -24.405  35.261  30.425  1.00   9.51
ATOM    509  O   THR    72     -24.562  34.027  30.269  1.00  11.35
ATOM    510  CB  THR    72     -23.036  35.596  28.328  1.00  15.61
ATOM    511  OG1 THR    72     -21.768  36.189  27.928  1.00  15.86
ATOM    512  CG2 THR    72     -24.177  36.178  27.494  1.00  14.54
ATOM    513  N   LEU    73     -25.282  36.028  31.020  1.00  11.12
ATOM    514  CA  LEU    73     -26.502  35.479  31.608  1.00   9.31
ATOM    515  C   LEU    73     -27.504  35.184  30.484  1.00   9.04
ATOM    516  O   LEU    73     -27.563  35.896  29.460  1.00   8.44
ATOM    517  CB  LEU    73     -27.046  36.412  32.687  1.00   8.84
ATOM    518  CG  LEU    73     -26.215  36.869  33.883  1.00  13.85
ATOM    519  CD1 LEU    73     -27.074  37.521  34.968  1.00  12.85
ATOM    520  CD2 LEU    73     -25.471  35.702  34.530  1.00   9.85
ATOM    521  N   THR    74     -28.295  34.161  30.737  1.00   7.42
ATOM    522  CG2 THR    74     -27.696  32.554  28.200  1.00   3.40
ATOM    523  OG1 THR    74     -29.174  31.283  29.642  1.00   9.42
ATOM    524  CB  THR    74     -29.063  32.532  28.922  1.00   7.73
ATOM    525  CA  THR    74     -29.389  33.735  29.859  1.00   7.40
ATOM    526  C   THR    74     -30.600  33.347  30.732  1.00  10.05
ATOM    527  O   THR    74     -30.473  33.184  31.959  1.00   7.44
ATOM    528  N   ASN    75     -31.775  33.201  30.069  1.00   8.53
ATOM    529  ND2 ASN    75     -36.021  33.747  28.974  1.00  14.07
ATOM    530  OD1 ASN    75     -33.929  33.279  28.252  1.00  14.16
ATOM    531  CG  ASN    75     -34.723  33.526  29.157  1.00  15.69
ATOM    532  CB  ASN    75     -34.178  33.518  30.570  1.00  11.17
ATOM    533  CA  ASN    75     -32.924  32.729  30.849  1.00   9.39
ATOM    534  C   ASN    75     -33.156  31.252  30.465  1.00  10.95
ATOM    535  O   ASN    75     -34.322  30.835  30.620  1.00  13.03
ATOM    536  N   LEU    76     -32.177  30.516  29.993  1.00   7.99
ATOM    537  CD2 LEU    76     -32.993  29.592  26.412  1.00  11.04
ATOM    538  CD1 LEU    76     -30.530  29.917  26.112  1.00  13.41
ATOM    539  CG  LEU    76     -31.687  29.987  27.082  1.00  11.12
ATOM    540  CB  LEU    76     -31.416  29.013  28.250  1.00  10.63
ATOM    541  CA  LEU    76     -32.315  29.158  29.530  1.00   8.79
ATOM    542  C   LEU    76     -31.876  28.059  30.512  1.00   8.97
ATOM    543  O   LEU    76     -31.038  28.290  31.385  1.00   6.01
ATOM    544  N   VAL    77     -32.529  26.936  30.323  1.00   8.54
ATOM    545  CA  VAL    77     -32.285  25.689  31.062  1.00   8.05
ATOM    546  C   VAL    77     -32.125  24.578  29.973  1.00   9.00
ATOM    547  O   VAL    77     -33.126  24.380  29.178  1.00   6.78
ATOM    548  CB  VAL    77     -33.397  25.290  32.052  1.00   8.09
ATOM    549  CG1 VAL    77     -33.049  23.911  32.715  1.00   5.84
```

```
ATOM    550  CG2  VAL    77     -33.575  26.350  33.142  1.00 10.07
ATOM    551  N    SER    78     -31.017  23.871  29.974  1.00  8.67
ATOM    552  OG   SER    78     -29.161  21.344  27.899  1.00  9.85
ATOM    553  CB   SER    78     -29.355  22.409  28.857  1.00 12.29
ATOM    554  CA   SER    78     -30.831  22.814  28.929  1.00  8.23
ATOM    555  C    SER    78     -31.710  21.583  29.189  1.00  9.82
ATOM    556  O    SER    78     -31.759  21.055  30.305  1.00  7.69
ATOM    557  N    ARG    79     -32.337  21.082  28.116  1.00  9.80
ATOM    558  NH2  ARG    79     -37.443  22.028  24.212  1.00 31.34
ATOM    559  NH1  ARG    79     -38.500  22.780  26.184  1.00 27.56
ATOM    560  CZ   ARG    79     -37.601  21.991  25.554  1.00 28.07
ATOM    561  NE   ARG    79     -36.785  21.131  26.161  1.00 21.89
ATOM    562  CD   ARG    79     -36.718  20.936  27.589  1.00 18.78
ATOM    563  CG   ARG    79     -35.265  21.118  27.992  1.00  9.14
ATOM    564  CB   ARG    79     -34.499  19.957  27.396  1.00  7.07
ATOM    565  CA   ARG    79     -33.163  19.879  28.166  1.00 10.01
ATOM    566  C    ARG    79     -32.272  18.740  27.659  1.00 11.09
ATOM    567  O    ARG    79     -32.799  17.622  27.476  1.00 11.76
ATOM    568  N    TYR    80     -30.980  18.901  27.456  1.00 10.89
ATOM    569  OH   TYR    80     -25.669  19.608  31.411  1.00 13.70
ATOM    570  CD2  TYR    80     -28.969  18.626  30.175  1.00  8.55
ATOM    571  CE2  TYR    80     -28.018  19.277  30.962  1.00  9.07
ATOM    572  CZ   TYR    80     -26.667  19.006  30.683  1.00 13.15
ATOM    573  CE1  TYR    80     -26.290  18.103  29.673  1.00 13.12
ATOM    574  CD1  TYR    80     -27.305  17.481  28.921  1.00 12.00
ATOM    575  CG   TYR    80     -28.646  17.742  29.153  1.00 10.87
ATOM    576  CB   TYR    80     -29.686  17.010  28.331  1.00 11.71
ATOM    577  CA   TYR    80     -30.100  17.809  27.036  1.00 13.19
ATOM    578  C    TYR    80     -30.669  16.889  25.939  1.00 15.57
ATOM    579  O    TYR    80     -31.074  17.414  24.848  1.00 16.53
ATOM    580  N    ASN    81     -30.732  15.583  26.157  1.00 15.67
ATOM    581  ND2  ASN    81     -30.251  12.075  23.672  0.50 23.42
ATOM    582  OD1  ASN    81     -31.653  10.851  24.930  0.50 22.68
ATOM    583  CG   ASN    81     -31.012  11.924  24.769  0.50 24.69
ATOM    584  CB   ASN    81     -30.915  13.117  25.699  0.50 20.33
ATOM    589  CA   ASN    81     -31.169  14.536  25.163  1.00 17.67
ATOM    590  C    ASN    81     -32.611  14.689  24.807  1.00 18.70
ATOM    591  O    ASN    81     -33.067  14.207  23.731  1.00 20.41
ATOM    592  N    THR    82     -33.405  15.385  25.621  1.00 15.25
ATOM    593  CG2  THR    82     -36.933  16.845  26.136  1.00 15.50
ATOM    594  OG1  THR    82     -35.944  14.838  27.235  1.00 15.80
ATOM    595  CB   THR    82     -35.663  16.070  26.495  1.00 13.76
ATOM    596  CA   THR    82     -34.787  15.661  25.275  1.00 16.61
ATOM    597  C    THR    82     -34.775  16.712  24.128  1.00 19.57
ATOM    598  O    THR    82     -35.725  16.765  23.314  1.00 20.18
ATOM    599  N    GLY    83     -33.765  17.555  23.973  1.00 17.44
ATOM    600  CA   GLY    83     -33.611  18.551  22.941  1.00 16.21
ATOM    601  C    GLY    83     -34.082  19.964  23.286  1.00 12.64
ATOM    602  O    GLY    83     -35.127  20.225  23.908  1.00 12.83
ATOM    603  N    GLY    84     -33.281  20.926  22.859  1.00 11.84
ATOM    604  CA   GLY    84     -33.604  22.331  23.082  1.00 11.09
ATOM    605  C    GLY    84     -33.492  22.741  24.541  1.00  9.78
ATOM    606  O    GLY    84     -32.796  22.177  25.384  1.00 10.83
ATOM    607  N    TYR    85     -34.104  23.875  24.825  1.00 10.88
```

```
ATOM    608  OH   TYR    85     -28.004  24.555  24.203  1.00 18.98
ATOM    609  CD2  TYR    85     -31.561  25.395  24.068  1.00 12.07
ATOM    610  CE2  TYR    85     -30.266  25.023  23.693  1.00 13.73
ATOM    611  CZ   TYR    85     -29.263  24.890  24.644  1.00 15.05
ATOM    612  CE1  TYR    85     -29.519  25.081  26.012  1.00 12.94
ATOM    613  CD1  TYR    85     -30.826  25.421  26.395  1.00 12.96
ATOM    614  CG   TYR    85     -31.850  25.570  25.445  1.00 11.64
ATOM    615  CB   TYR    85     -33.264  25.866  25.882  1.00 10.50
ATOM    616  CA   TYR    85     -34.079  24.539  26.116  1.00 10.86
ATOM    617  C    TYR    85     -35.418  25.002  26.674  1.00 13.82
ATOM    618  O    TYR    85     -36.268  25.491  25.854  1.00 14.41
ATOM    619  N    ALA    86     -35.569  24.891  27.969  1.00  9.86
ATOM    620  CB   ALA    86     -37.046  24.630  29.971  1.00  9.75
ATOM    621  CA   ALA    86     -36.735  25.425  28.695  1.00 11.67
ATOM    622  C    ALA    86     -36.361  26.918  28.958  1.00 11.87
ATOM    623  O    ALA    86     -35.188  27.341  28.972  1.00  9.92
ATOM    624  N    THR    87     -37.345  27.829  29.131  1.00 10.43
ATOM    625  CG2  THR    87     -36.841  29.875  26.861  1.00 17.11
ATOM    626  OG1  THR    87     -38.959  29.934  28.083  1.00 17.19
ATOM    627  CB   THR    87     -37.539  30.174  28.200  1.00 17.24
ATOM    628  CA   THR    87     -37.057  29.241  29.379  1.00 10.64
ATOM    629  C    THR    87     -37.640  29.593  30.724  1.00 11.34
ATOM    630  O    THR    87     -38.696  29.055  31.041  1.00 13.09
ATOM    631  N    VAL    88     -37.001  30.448  31.521  1.00 10.66
ATOM    632  CA   VAL    88     -37.441  30.863  32.856  1.00  9.45
ATOM    633  C    VAL    88     -38.255  32.155  32.696  1.00 11.88
ATOM    634  O    VAL    88     -37.698  33.094  32.136  1.00 10.63
ATOM    635  CB   VAL    88     -36.246  31.053  33.821  1.00  7.00
ATOM    636  CG1  VAL    88     -36.652  31.636  35.192  1.00  5.32
ATOM    637  CG2  VAL    88     -35.478  29.746  33.985  1.00  9.05
ATOM    638  N    ALA    89     -39.467  32.233  33.201  1.00 10.89
ATOM    639  CB   ALA    89     -41.539  33.201  32.260  1.00  9.11
ATOM    640  CA   ALA    89     -40.325  33.440  33.132  1.00 11.01
ATOM    641  C    ALA    89     -40.690  33.918  34.548  1.00 11.13
ATOM    642  O    ALA    89     -41.242  35.028  34.655  1.00 13.90
ATOM    643  N    GLY    90     -40.351  33.181  35.617  1.00  9.54
ATOM    644  CA   GLY    90     -40.632  33.592  36.976  1.00  8.75
ATOM    645  C    GLY    90     -40.322  32.409  37.921  1.00 10.19
ATOM    646  O    GLY    90     -39.660  31.477  37.500  1.00  9.62
ATOM    647  N    HIS    91     -40.857  32.540  39.135  1.00 11.81
ATOM    648  CD2  HIS    91     -40.073  33.404  43.018  1.00 18.32
ATOM    649  NE2  HIS    91     -40.052  34.763  43.177  1.00 17.97
ATOM    650  CE1  HIS    91     -39.622  35.366  42.127  1.00 17.17
ATOM    651  ND1  HIS    91     -39.350  34.411  41.259  1.00 16.07
ATOM    652  CG   HIS    91     -39.605  33.184  41.765  1.00 16.04
ATOM    653  CB   HIS    91     -39.411  31.883  41.060  1.00 11.82
ATOM    654  CA   HIS    91     -40.637  31.530  40.180  1.00 10.58
ATOM    655  C    HIS    91     -41.854  31.229  41.025  1.00 12.38
ATOM    656  O    HIS    91     -41.723  31.032  42.248  1.00 13.11
ATOM    657  N    ASN    92     -43.013  31.126  40.369  1.00 12.16
ATOM    658  ND2  ASN    92     -46.608  32.760  41.360  1.00 44.37
ATOM    659  OD1  ASN    92     -45.564  33.225  39.385  1.00 40.52
ATOM    660  CG   ASN    92     -45.903  32.418  40.259  1.00 35.33
ATOM    661  CB   ASN    92     -45.524  30.938  40.252  1.00 23.82
```

```
ATOM    662  CA  ASN    92     -44.261  30.746  41.119  1.00  13.35
ATOM    663  C   ASN    92     -44.164  29.268  41.493  1.00  12.66
ATOM    664  O   ASN    92     -43.930  28.437  40.582  1.00  11.76
ATOM    665  N   GLN    93     -44.364  28.935  42.749  1.00  11.08
ATOM    666  NE2 GLN    93     -42.340  27.432  47.693  1.00  21.50
ATOM    667  OE1 GLN    93     -44.559  27.501  47.458  1.00  31.26
ATOM    668  CD  GLN    93     -43.422  27.632  46.972  1.00  27.63
ATOM    669  CG  GLN    93     -43.291  28.002  45.511  1.00  20.72
ATOM    670  CB  GLN    93     -44.409  27.379  44.700  1.00  15.24
ATOM    671  CA  GLN    93     -44.262  27.516  43.171  1.00  12.74
ATOM    672  C   GLN    93     -45.394  26.705  42.566  1.00  13.82
ATOM    673  O   GLN    93     -46.572  27.162  42.672  1.00  15.94
ATOM    674  N   ALA    94     -45.166  25.549  42.048  1.00  11.74
ATOM    675  CA  ALA    94     -46.178  24.676  41.481  1.00  11.41
ATOM    676  C   ALA    94     -46.815  23.934  42.649  1.00  14.20
ATOM    677  O   ALA    94     -46.120  23.587  43.637  1.00  14.08
ATOM    678  CB  ALA    94     -45.495  23.704  40.529  1.00   6.58
ATOM    679  N   PRO    95     -48.112  23.645  42.551  1.00  14.96
ATOM    680  CG  PRO    95     -50.259  23.275  41.661  1.00  15.96
ATOM    681  CD  PRO    95     -48.954  24.020  41.412  1.00  15.38
ATOM    682  CB  PRO    95     -50.261  22.810  43.087  1.00  13.99
ATOM    683  CA  PRO    95     -48.815  22.843  43.571  1.00  13.77
ATOM    684  C   PRO    95     -48.308  21.414  43.670  1.00  12.85
ATOM    685  O   PRO    95     -47.789  20.722  42.764  1.00  13.21
ATOM    686  N   ILE    96     -48.439  20.860  44.892  1.00   9.64
ATOM    687  CD1 ILE    96     -46.305  19.698  47.937  1.00  20.39
ATOM    688  CG1 ILE    96     -47.785  19.940  47.690  1.00  17.20
ATOM    689  CB  ILE    96     -48.425  19.023  46.634  1.00  13.72
ATOM    690  CG2 ILE    96     -48.131  17.530  46.952  1.00  17.91
ATOM    691  CA  ILE    96     -48.058  19.444  45.141  1.00  11.51
ATOM    692  C   ILE    96     -48.841  18.627  44.138  1.00  13.14
ATOM    693  O   ILE    96     -50.052  18.979  43.880  1.00  15.21
ATOM    694  N   GLY    97     -48.332  17.575  43.528  1.00  10.18
ATOM    695  CA  GLY    97     -49.020  16.783  42.537  1.00   9.00
ATOM    696  C   GLY    97     -48.645  17.200  41.126  1.00  11.33
ATOM    697  O   GLY    97     -48.867  16.374  40.221  1.00  12.32
ATOM    698  N   SER    98     -48.108  18.393  40.935  1.00  10.97
ATOM    699  OG  SER    98     -48.122  21.262  40.073  0.70  15.96
ATOM    700  CB  SER    98     -47.149  20.355  39.724  0.70  13.01
ATOM    703  CA  SER    98     -47.643  18.918  39.637  1.00  11.70
ATOM    704  C   SER    98     -46.376  18.198  39.140  1.00  11.01
ATOM    705  O   SER    98     -45.567  17.708  39.906  1.00  12.53
ATOM    706  N   SER    99     -46.203  18.149  37.825  1.00   8.54
ATOM    707  OG  SER    99     -45.372  18.423  34.957  1.00  12.93
ATOM    708  CB  SER    99     -45.157  17.258  35.747  1.00   7.78
ATOM    709  CA  SER    99     -45.010  17.562  37.226  1.00   8.54
ATOM    710  C   SER    99     -43.921  18.659  37.391  1.00   7.90
ATOM    711  O   SER    99     -44.195  19.884  37.534  1.00  10.31
ATOM    712  N   VAL   100     -42.675  18.231  37.384  1.00   9.21
ATOM    713  CA  VAL   100     -41.468  19.082  37.505  1.00   5.59
ATOM    714  C   VAL   100     -40.375  18.343  36.773  1.00   5.35
ATOM    715  O   VAL   100     -40.380  17.108  36.785  1.00   9.03
ATOM    716  CB  VAL   100     -41.112  19.395  38.979  1.00   5.88
ATOM    717  CG1 VAL   100     -40.630  18.114  39.670  1.00   8.61
```

```
ATOM    718  CG2 VAL   100     -40.142  20.579  39.127  1.00   5.24
ATOM    719  N   CYS   101     -39.423  19.055  36.168  1.00   5.24
ATOM    720  CA  CYS   101     -38.304  18.494  35.437  1.00   4.35
ATOM    721  C   CYS   101     -36.989  18.996  36.086  1.00   5.37
ATOM    722  O   CYS   101     -36.984  20.152  36.529  1.00   8.17
ATOM    723  CB  CYS   101     -38.312  18.824  33.935  1.00   5.99
ATOM    724  SG  CYS   101     -39.723  18.001  33.063  1.00   8.35
ATOM    725  N   ARG   102     -35.982  18.175  36.084  1.00   6.08
ATOM    726  CA  ARG   102     -34.649  18.527  36.587  1.00   7.57
ATOM    727  C   ARG   102     -33.605  18.534  35.462  1.00   8.71
ATOM    728  O   ARG   102     -33.604  17.647  34.598  1.00   8.00
ATOM    729  CB  ARG   102     -34.261  17.489  37.655  1.00   4.69
ATOM    730  CG  ARG   102     -32.859  17.784  38.286  1.00   3.27
ATOM    731  CD  ARG   102     -32.303  16.653  39.077  1.00   6.25
ATOM    732  NE  ARG   102     -32.250  15.402  38.343  1.00   7.04
ATOM    733  CZ  ARG   102     -31.471  15.083  37.294  1.00   9.62
ATOM    734  NH1 ARG   102     -31.692  13.864  36.773  1.00   9.55
ATOM    735  NH2 ARG   102     -30.608  15.953  36.805  1.00   5.91
ATOM    736  N   SER   103     -32.662  19.454  35.404  1.00   7.27
ATOM    737  CA  SER   103     -31.567  19.475  34.435  1.00   4.96
ATOM    738  C   SER   103     -30.259  19.365  35.228  1.00   6.42
ATOM    739  O   SER   103     -30.059  20.177  36.162  1.00   6.49
ATOM    740  CB  SER   103     -31.571  20.781  33.624  1.00   5.59
ATOM    741  OG  SER   103     -30.581  20.673  32.575  1.00   7.71
ATOM    742  N   GLY   104     -29.359  18.411  34.965  1.00   7.52
ATOM    743  CA  GLY   104     -28.071  18.282  35.661  1.00   5.92
ATOM    744  C   GLY   104     -27.031  17.745  34.686  1.00   6.41
ATOM    745  O   GLY   104     -27.354  17.083  33.665  1.00   7.09
ATOM    746  N   SER   105     -25.757  18.002  34.912  1.00   7.88
ATOM    747  OG  SER   105     -22.953  18.433  35.504  1.00  11.75
ATOM    748  CB  SER   105     -23.430  18.504  34.179  1.00   7.00
ATOM    749  CA  SER   105     -24.638  17.559  34.049  1.00  10.37
ATOM    750  C   SER   105     -24.255  16.085  34.102  1.00  10.06
ATOM    751  O   SER   105     -23.505  15.679  33.176  1.00  10.75
ATOM    752  N   THR   106     -24.719  15.248  35.018  1.00   9.74
ATOM    753  CA  THR   106     -24.403  13.811  35.029  1.00   9.92
ATOM    754  C   THR   106     -25.458  13.046  34.238  1.00   8.56
ATOM    755  O   THR   106     -25.079  12.174  33.464  1.00  10.42
ATOM    756  CB  THR   106     -24.322  13.103  36.435  1.00  10.71
ATOM    757  OG1 THR   106     -23.436  13.978  37.167  1.00  10.45
ATOM    758  CG2 THR   106     -23.782  11.671  36.508  1.00   6.76
ATOM    759  N   THR   107     -26.723  13.319  34.467  1.00   7.87
ATOM    760  CA  THR   107     -27.804  12.599  33.831  1.00   5.96
ATOM    761  C   THR   107     -28.634  13.349  32.838  1.00   7.88
ATOM    762  O   THR   107     -29.531  12.664  32.266  1.00   8.47
ATOM    763  CB  THR   107     -28.695  11.935  34.969  1.00   8.85
ATOM    764  OG1 THR   107     -29.241  13.086  35.695  1.00   7.24
ATOM    765  CG2 THR   107     -27.869  11.012  35.858  1.00   8.14
ATOM    766  N   GLY   108     -28.523  14.609  32.643  1.00   7.16
ATOM    767  CA  GLY   108     -29.341  15.323  31.611  1.00   8.94
ATOM    768  C   GLY   108     -30.668  15.756  32.223  1.00  10.50
ATOM    769  O   GLY   108     -30.722  16.175  33.436  1.00   8.98
ATOM    770  N   TRP   109     -31.691  15.642  31.408  1.00   6.52
ATOM    771  CD2 TRP   109     -35.413  18.684  30.968  1.00   5.39
```

```
ATOM    772  CE3 TRP   109     -34.790  19.728  31.656  1.00   5.67
ATOM    773  CZ3 TRP   109     -35.588  20.864  31.900  1.00  10.11
ATOM    774  CH2 TRP   109     -36.931  20.950  31.533  1.00   7.46
ATOM    775  CZ2 TRP   109     -37.555  19.912  30.864  1.00   5.36
ATOM    776  CE2 TRP   109     -36.762  18.789  30.603  1.00   8.40
ATOM    777  NE1 TRP   109     -37.097  17.619  29.964  1.00  11.33
ATOM    778  CD1 TRP   109     -35.996  16.771  29.909  1.00   8.89
ATOM    779  CG  TRP   109     -34.928  17.409  30.506  1.00   7.87
ATOM    780  CB  TRP   109     -33.558  16.856  30.594  1.00   4.08
ATOM    781  CA  TRP   109     -33.070  16.106  31.803  1.00   6.13
ATOM    782  C   TRP   109     -34.031  15.013  32.176  1.00   7.55
ATOM    783  O   TRP   109     -34.244  14.017  31.372  1.00   8.28
ATOM    784  N   HIS   110     -34.566  15.040  33.380  1.00   6.29
ATOM    785  CD2 HIS   110     -32.409  12.573  33.819  1.00   8.99
ATOM    786  NE2 HIS   110     -31.845  11.558  33.121  1.00  10.03
ATOM    787  CE1 HIS   110     -32.751  10.595  32.981  1.00  12.94
ATOM    788  ND1 HIS   110     -33.856  11.027  33.562  1.00  12.68
ATOM    789  CG  HIS   110     -33.678  12.246  34.128  1.00   9.92
ATOM    790  CB  HIS   110     -34.761  13.004  34.840  1.00   8.94
ATOM    791  CA  HIS   110     -35.487  13.971  33.861  1.00   7.82
ATOM    792  C   HIS   110     -36.648  14.637  34.584  1.00   7.74
ATOM    793  O   HIS   110     -36.444  15.708  35.190  1.00   8.03
ATOM    794  N   CYS   111     -37.832  13.990  34.506  1.00   7.77
ATOM    795  CA  CYS   111     -39.052  14.589  35.065  1.00   7.64
ATOM    796  C   CYS   111     -39.864  13.660  35.952  1.00   9.31
ATOM    797  O   CYS   111     -39.559  12.451  35.928  1.00  11.03
ATOM    798  CB  CYS   111     -39.988  15.100  33.925  1.00   9.61
ATOM    799  SG  CYS   111     -39.150  16.153  32.711  1.00   9.12
ATOM    800  N   GLY   112     -40.828  14.245  36.638  1.00   8.81
ATOM    801  CA  GLY   112     -41.625  13.408  37.597  1.00   8.51
ATOM    802  C   GLY   112     -42.521  14.315  38.399  1.00  10.25
ATOM    803  O   GLY   112     -42.794  15.437  37.941  1.00  12.04
ATOM    804  N   THR   113     -42.979  13.969  39.595  1.00  10.08
ATOM    805  CA  THR   113     -43.870  14.809  40.372  1.00   8.62
ATOM    806  C   THR   113     -43.359  15.387  41.685  1.00   9.71
ATOM    807  O   THR   113     -42.441  14.786  42.268  1.00  10.48
ATOM    808  CB  THR   113     -45.240  13.996  40.648  1.00  17.08
ATOM    809  OG1 THR   113     -44.930  12.755  41.340  1.00  19.10
ATOM    810  CG2 THR   113     -46.004  13.705  39.362  1.00  15.24
ATOM    811  N   ILE   114     -43.963  16.488  42.073  1.00   8.35
ATOM    812  CA  ILE   114     -43.662  17.108  43.365  1.00   9.73
ATOM    813  C   ILE   114     -44.554  16.338  44.383  1.00  13.59
ATOM    814  O   ILE   114     -45.816  16.336  44.198  1.00  12.54
ATOM    815  CB  ILE   114     -44.008  18.621  43.384  1.00  10.58
ATOM    816  CG1 ILE   114     -43.089  19.319  42.341  1.00  12.00
ATOM    817  CG2 ILE   114     -43.864  19.215  44.814  1.00  12.84
ATOM    818  CD1 ILE   114     -43.555  20.750  42.065  1.00  10.62
ATOM    819  N   GLN   115     -43.977  15.668  45.379  1.00  12.39
ATOM    820  NE2 GLN   115     -43.951  10.378  45.759  1.00  33.00
ATOM    821  OE1 GLN   115     -42.098  11.415  46.407  1.00  34.76
ATOM    822  CD  GLN   115     -43.243  11.496  45.943  1.00  30.30
ATOM    823  CG  GLN   115     -43.993  12.758  45.524  1.00  18.83
ATOM    824  CB  GLN   115     -44.077  13.606  46.811  1.00  11.43
ATOM    825  CA  GLN   115     -44.732  14.936  46.396  1.00  11.59
```

```
ATOM    826  C   GLN   115     -44.956  15.640  47.693  1.00 11.61
ATOM    827  O   GLN   115     -46.105  15.494  48.196  1.00 14.96
ATOM    828  N   ALA   116     -44.037  16.355  48.292  1.00 12.17
ATOM    829  CA  ALA   116     -44.291  16.976  49.618  1.00 10.65
ATOM    830  C   ALA   116     -43.263  18.055  49.863  1.00  9.88
ATOM    831  O   ALA   116     -42.162  17.978  49.326  1.00 13.41
ATOM    832  CB  ALA   116     -44.101  15.894  50.689  1.00 10.10
ATOM    833  N   ARG   117     -43.586  19.020  50.636  1.00  9.81
ATOM    834  NH2 ARG   117     -43.870  23.560  45.115  1.00 13.10
ATOM    835  NH1 ARG   117     -45.496  23.020  46.568  1.00 17.40
ATOM    836  CZ  ARG   117     -44.191  23.340  46.386  1.00 16.37
ATOM    837  NE  ARG   117     -43.268  23.465  47.330  1.00 14.91
ATOM    838  CD  ARG   117     -43.450  23.251  48.783  1.00 13.89
ATOM    839  CG  ARG   117     -43.323  21.801  49.092  1.00 10.78
ATOM    840  CB  ARG   117     -43.392  21.470  50.596  1.00 10.30
ATOM    841  CA  ARG   117     -42.725  20.137  50.983  1.00 10.62
ATOM    842  C   ARG   117     -42.465  20.023  52.496  1.00 12.42
ATOM    843  O   ARG   117     -43.122  19.229  53.201  1.00 14.36
ATOM    844  N   GLY   118     -41.566  20.803  52.999  1.00 10.94
ATOM    845  CA  GLY   118     -41.246  20.891  54.430  1.00 14.46
ATOM    846  C   GLY   118     -40.590  19.675  55.005  1.00 13.77
ATOM    847  O   GLY   118     -40.761  19.531  56.229  1.00 14.95
ATOM    848  N   GLN   119     -39.874  18.886  54.215  1.00 11.83
ATOM    849  NE2 GLN   119     -42.518  16.522  54.159  1.00 27.14
ATOM    850  OE1 GLN   119     -41.331  14.597  53.939  1.00 29.04
ATOM    851  CD  GLN   119     -41.505  15.779  53.683  1.00 26.05
ATOM    852  CG  GLN   119     -40.511  16.511  52.791  1.00 23.83
ATOM    853  CB  GLN   119     -39.161  16.633  53.499  1.00 15.28
ATOM    854  CA  GLN   119     -39.228  17.649  54.654  1.00 12.25
ATOM    855  C   GLN   119     -37.819  17.866  55.191  1.00 13.13
ATOM    856  O   GLN   119     -37.023  18.655  54.674  1.00 11.96
ATOM    857  N   SER   120     -37.520  17.136  56.272  1.00 12.77
ATOM    858  OG  SER   120     -36.874  16.674  59.024  0.50 13.43
ATOM    859  CB  SER   120     -36.074  17.591  58.330  0.50 15.06
ATOM    862  CA  SER   120     -36.147  17.234  56.873  1.00 11.79
ATOM    863  C   SER   120     -35.513  15.938  56.438  1.00 14.19
ATOM    864  O   SER   120     -36.167  14.855  56.352  1.00 14.17
ATOM    865  N   VAL   121     -34.228  16.035  56.037  1.00 14.53
ATOM    866  CG2 VAL   121     -34.392  15.445  53.235  1.00 20.02
ATOM    867  CG1 VAL   121     -32.537  13.814  53.494  1.00 22.53
ATOM    868  CB  VAL   121     -33.176  15.085  54.041  1.00 19.23
ATOM    869  CA  VAL   121     -33.466  14.920  55.565  1.00 14.60
ATOM    870  C   VAL   121     -32.106  14.892  56.248  1.00 17.85
ATOM    871  O   VAL   121     -31.399  15.890  56.335  1.00 16.78
ATOM    872  N   SER   122     -31.749  13.694  56.677  1.00 18.77
ATOM    873  OG  SER   122     -31.320  13.436  59.447  1.00 35.50
ATOM    874  CB  SER   122     -30.306  12.902  58.611  1.00 26.24
ATOM    875  CA  SER   122     -30.397  13.594  57.262  1.00 20.95
ATOM    876  C   SER   122     -29.504  12.911  56.238  1.00 20.78
ATOM    877  O   SER   122     -29.704  11.746  55.840  1.00 25.20
ATOM    878  N   TYR   123     -28.548  13.651  55.794  1.00 19.04
ATOM    879  CA  TYR   123     -27.479  13.164  54.927  1.00 21.72
ATOM    880  C   TYR   123     -26.478  12.615  55.995  1.00 25.29
ATOM    881  O   TYR   123     -26.521  13.015  57.187  1.00 26.53
```

```
ATOM    882  CB   TYR  123     -26.981  14.342  54.135  1.00 18.93
ATOM    883  CG   TYR  123     -27.915  14.920  53.100  1.00 18.61
ATOM    884  CD1  TYR  123     -27.849  16.273  52.784  1.00 15.70
ATOM    885  CD2  TYR  123     -28.840  14.144  52.381  1.00 21.00
ATOM    886  CE1  TYR  123     -28.658  16.844  51.808  1.00 15.37
ATOM    887  CE2  TYR  123     -29.712  14.700  51.423  1.00 18.34
ATOM    888  CZ   TYR  123     -29.581  16.067  51.133  1.00 16.62
ATOM    889  OH   TYR  123     -30.390  16.593  50.172  1.00 15.25
ATOM    890  N    PRO  124     -25.578  11.721  55.647  1.00 28.48
ATOM    891  CG   PRO  124     -24.105  10.334  54.354  1.00 32.40
ATOM    892  CD   PRO  124     -25.391  11.155  54.297  1.00 30.53
ATOM    893  CB   PRO  124     -23.748  10.168  55.828  1.00 32.32
ATOM    894  CA   PRO  124     -24.583  11.183  56.598  1.00 31.44
ATOM    895  C    PRO  124     -23.732  12.285  57.226  1.00 32.68
ATOM    896  O    PRO  124     -23.355  12.124  58.408  1.00 33.64
ATOM    897  N    GLU  125     -23.417  13.329  56.485  1.00 32.09
ATOM    898  CA   GLU  125     -22.646  14.515  56.843  1.00 32.45
ATOM    899  C    GLU  125     -23.410  15.484  57.766  1.00 33.22
ATOM    900  O    GLU  125     -22.932  15.954  58.861  1.00 33.87
ATOM    901  CB   GLU  125     -22.144  15.220  55.588  1.00 28.10
ATOM    902  CG   GLU  125     -22.899  15.278  54.299  1.00 34.56
ATOM    903  CD   GLU  125     -23.341  14.605  53.384  0.00 53.35
ATOM    904  OE1  GLU  125     -23.517  15.100  52.231  0.00 59.96
ATOM    905  OE2  GLU  125     -23.156  13.352  53.591  0.00 58.46
ATOM    906  N    GLY  126     -24.666  15.793  57.397  1.00 31.75
ATOM    907  CA   GLY  126     -25.549  16.682  58.182  1.00 28.35
ATOM    908  C    GLY  126     -27.017  16.695  57.720  1.00 25.07
ATOM    909  O    GLY  126     -27.393  16.107  56.682  1.00 25.93
ATOM    910  N    THR  127     -27.811  17.417  58.486  1.00 19.30
ATOM    911  CG2  THR  127     -31.485  17.638  59.616  1.00 15.49
ATOM    912  OG1  THR  127     -29.548  16.190  60.199  1.00 22.50
ATOM    913  CB   THR  127     -29.964  17.487  59.664  1.00 14.93
ATOM    914  CA   THR  127     -29.242  17.558  58.256  1.00 13.91
ATOM    915  C    THR  127     -29.689  18.791  57.491  1.00 11.25
ATOM    916  O    THR  127     -29.203  19.885  57.803  1.00 10.59
ATOM    917  N    VAL  128     -30.649  18.626  56.584  1.00 11.18
ATOM    918  CA   VAL  128     -31.201  19.747  55.791  1.00  9.77
ATOM    919  C    VAL  128     -32.688  19.787  56.164  1.00  8.45
ATOM    920  O    VAL  128     -33.182  18.697  56.393  1.00 11.45
ATOM    921  CB   VAL  128     -30.956  19.633  54.298  1.00  7.25
ATOM    922  CG1  VAL  128     -29.466  19.790  54.013  1.00 11.55
ATOM    923  CG2  VAL  128     -31.377  18.285  53.735  1.00  9.36
ATOM    924  N    THR  129     -33.266  20.960  56.248  1.00  9.49
ATOM    925  CG2  THR  129     -34.182  21.202  59.125  1.00 18.71
ATOM    926  OG1  THR  129     -34.282  23.173  57.758  1.00 14.40
ATOM    927  CB   THR  129     -34.884  21.913  57.959  1.00  8.96
ATOM    928  CA   THR  129     -34.680  21.088  56.613  1.00  9.66
ATOM    929  C    THR  129     -35.407  21.804  55.487  1.00 10.11
ATOM    930  O    THR  129     -34.796  22.467  54.615  1.00 10.92
ATOM    931  N    ASN  130     -36.709  21.619  55.563  1.00 10.84
ATOM    932  ND2  ASN  130     -38.570  25.717  53.765  1.00 35.10
ATOM    933  OD1  ASN  130     -39.854  23.969  54.369  1.00 28.19
ATOM    934  CG   ASN  130     -38.739  24.527  54.362  1.00 30.11
ATOM    935  CB   ASN  130     -37.496  23.827  54.952  1.00 17.09
```

```
ATOM    936  CA  ASN  130    -37.620  22.299  54.616  1.00 12.34
ATOM    937  C   ASN  130    -37.388  21.988  53.136  1.00 11.59
ATOM    938  O   ASN  130    -37.557  22.883  52.268  1.00 11.46
ATOM    939  N   MET  131    -37.056  20.742  52.880  1.00  9.76
ATOM    940  CE  MET  131    -33.020  20.248  50.187  1.00 16.57
ATOM    941  SD  MET  131    -33.597  21.082  51.629  1.00 20.94
ATOM    942  CG  MET  131    -34.411  19.573  52.379  1.00  9.59
ATOM    943  CB  MET  131    -35.664  19.199  51.580  1.00  5.73
ATOM    944  CA  MET  131    -36.732  20.297  51.529  1.00  9.93
ATOM    945  C   MET  131    -38.007  19.797  50.840  1.00  9.00
ATOM    946  O   MET  131    -38.962  19.372  51.519  1.00 10.48
ATOM    947  N   THR  132    -37.995  19.869  49.527  1.00  8.82
ATOM    948  CA  THR  132    -39.129  19.393  48.710  1.00  5.72
ATOM    949  C   THR  132    -38.769  18.054  48.108  1.00  7.44
ATOM    950  O   THR  132    -37.719  17.850  47.428  1.00  9.83
ATOM    951  CB  THR  132    -39.497  20.516  47.675  1.00  6.44
ATOM    952  OG1 THR  132    -39.851  21.700  48.434  1.00  9.35
ATOM    953  CG2 THR  132    -40.681  20.100  46.737  1.00  7.59
ATOM    954  N   ARG  133    -39.640  17.061  48.306  1.00  4.85
ATOM    955  NH2 ARG  133    -42.116  12.875  51.526  1.00 39.69
ATOM    956  NH1 ARG  133    -43.846  11.985  50.304  1.00 32.03
ATOM    957  CZ  ARG  133    -42.539  12.272  50.397  1.00 36.90
ATOM    958  NE  ARG  133    -41.666  11.948  49.418  1.00 28.98
ATOM    959  CD  ARG  133    -40.253  12.204  49.398  1.00 20.06
ATOM    960  CG  ARG  133    -39.832  13.218  48.354  1.00 11.77
ATOM    961  CB  ARG  133    -40.079  14.660  48.801  1.00  6.59
ATOM    962  CA  ARG  133    -39.443  15.674  47.833  1.00  6.76
ATOM    963  C   ARG  133    -40.092  15.457  46.455  1.00  7.46
ATOM    964  O   ARG  133    -41.227  15.963  46.241  1.00  9.38
ATOM    965  N   THR  134    -39.360  14.793  45.552  1.00  9.68
ATOM    966  CG2 THR  134    -39.353  17.060  43.521  1.00  7.44
ATOM    967  OG1 THR  134    -38.110  15.030  42.788  1.00  8.17
ATOM    968  CB  THR  134    -39.392  15.603  43.141  1.00  8.74
ATOM    969  CA  THR  134    -39.921  14.565  44.202  1.00  8.24
ATOM    970  C   THR  134    -39.576  13.135  43.785  1.00  8.06
ATOM    971  O   THR  134    -38.694  12.518  44.396  1.00  9.92
ATOM    972  N   THR  135    -40.301  12.622  42.770  1.00  7.24
ATOM    973  CG2 THR  135    -42.463  10.541  42.733  1.00 12.10
ATOM    974  OG1 THR  135    -41.763  11.403  40.497  1.00 11.13
ATOM    975  CB  THR  135    -41.362  10.601  41.650  1.00 10.58
ATOM    976  CA  THR  135    -40.037  11.294  42.228  1.00  8.03
ATOM    977  C   THR  135    -38.974  11.340  41.147  1.00  7.98
ATOM    978  O   THR  135    -38.731  10.327  40.471  1.00  9.10
ATOM    979  N   VAL  136    -38.326  12.452  40.852  1.00 10.38
ATOM    980  CG2 VAL  136    -38.483  14.754  39.130  1.00  6.65
ATOM    981  CG1 VAL  136    -36.094  14.300  38.374  1.00 10.08
ATOM    982  CB  VAL  136    -37.136  14.096  39.495  1.00  9.89
ATOM    983  CA  VAL  136    -37.296  12.595  39.813  1.00  9.10
ATOM    984  C   VAL  136    -35.990  11.927  40.235  1.00  9.23
ATOM    985  O   VAL  136    -35.640  12.113  41.414  1.00 11.00
ATOM    986  N   CYS  137    -35.273  11.188  39.408  1.00  7.90
ATOM    987  CA  CYS  137    -33.997  10.564  39.780  1.00  8.61
ATOM    988  C   CYS  137    -32.841  11.600  39.681  1.00  9.07
ATOM    989  O   CYS  137    -33.024  12.659  39.015  1.00  9.87
```

```
ATOM    990  CB   CYS  137     -33.702    9.452   38.761  1.00   8.35
ATOM    991  SG   CYS  137     -33.425   10.011   37.031  1.00  11.68
ATOM    992  N    ALA  138     -31.687   11.330   40.300  1.00   7.09
ATOM    993  CB   ALA  138     -30.467   13.454   41.104  1.00   8.40
ATOM    994  CA   ALA  138     -30.503   12.207   40.220  1.00   8.25
ATOM    995  C    ALA  138     -29.294   11.352   40.568  1.00   8.58
ATOM    996  O    ALA  138     -29.409   10.287   41.211  1.00  10.28
ATOM    997  N    GLU  139     -28.105   11.803   40.178  1.00   9.17
ATOM    998  OE2  GLU  139     -27.880    7.597   37.175  1.00  10.81
ATOM    999  OE1  GLU  139     -25.864    8.348   37.135  1.00  10.87
ATOM   1000  CD   GLU  139     -26.946    8.270   37.673  1.00  12.62
ATOM   1001  CG   GLU  139     -27.289    9.053   38.912  1.00  10.79
ATOM   1002  CB   GLU  139     -26.414   10.298   39.196  1.00   8.09
ATOM   1003  CA   GLU  139     -26.818   11.099   40.431  1.00   9.02
ATOM   1004  C    GLU  139     -25.776   12.156   40.775  1.00   9.85
ATOM   1005  O    GLU  139     -25.966   13.362   40.507  1.00   9.59
ATOM   1006  N    PRO  140     -24.677   11.769   41.394  1.00  11.00
ATOM   1007  CG   PRO  140     -23.255   10.606   42.890  1.00  10.81
ATOM   1008  CD   PRO  140     -24.305   10.376   41.788  1.00  10.23
ATOM   1009  CB   PRO  140     -22.595   11.921   42.569  1.00  13.07
ATOM   1010  CA   PRO  140     -23.611   12.741   41.794  1.00  10.28
ATOM   1011  C    PRO  140     -23.095   13.561   40.611  1.00   9.93
ATOM   1012  O    PRO  140     -22.846   13.081   39.498  1.00  11.30
ATOM   1013  N    GLY  141     -23.015   14.865   40.884  1.00   7.17
ATOM   1014  CA   GLY  141     -22.596   15.857   39.927  1.00   7.59
ATOM   1015  C    GLY  141     -23.845   16.611   39.448  1.00   6.72
ATOM   1016  O    GLY  141     -23.742   17.715   38.907  1.00   7.49
ATOM   1017  N    ASP  142     -25.050   16.077   39.671  1.00   7.35
ATOM   1018  CA   ASP  142     -26.325   16.710   39.296  1.00   6.21
ATOM   1019  C    ASP  142     -26.663   17.752   40.369  1.00   5.40
ATOM   1020  O    ASP  142     -27.522   18.627   40.062  1.00   3.95
ATOM   1021  CB   ASP  142     -27.497   15.784   39.058  1.00   7.83
ATOM   1022  CG   ASP  142     -27.531   14.867   37.860  1.00   7.53
ATOM   1023  OD1  ASP  142     -28.075   13.736   37.908  1.00   7.92
ATOM   1024  OD2  ASP  142     -27.048   15.355   36.863  1.00   6.85
ATOM   1025  N    SER  143     -26.112   17.668   41.546  1.00   5.60
ATOM   1026  CA   SER  143     -26.422   18.670   42.589  1.00   5.95
ATOM   1027  C    SER  143     -26.287   20.098   42.102  1.00   7.22
ATOM   1028  O    SER  143     -25.328   20.407   41.346  1.00   7.03
ATOM   1029  CB   SER  143     -25.451   18.527   43.777  1.00   7.47
ATOM   1030  OG   SER  143     -25.764   17.255   44.327  1.00  11.26
ATOM   1031  N    GLY  144     -27.206   20.956   42.571  1.00   5.35
ATOM   1032  CA   GLY  144     -27.301   22.370   42.249  1.00   5.48
ATOM   1033  C    GLY  144     -28.051   22.665   40.945  1.00   6.00
ATOM   1034  O    GLY  144     -28.334   23.858   40.698  1.00   7.24
ATOM   1035  N    GLY  145     -28.295   21.671   40.140  1.00   5.00
ATOM   1036  CA   GLY  145     -28.959   21.818   38.828  1.00   5.08
ATOM   1037  C    GLY  145     -30.400   22.272   38.981  1.00   6.80
ATOM   1038  O    GLY  145     -31.096   22.093   40.013  1.00   8.09
ATOM   1039  N    SER  146     -31.016   22.823   37.953  1.00   4.98
ATOM   1040  CA   SER  146     -32.375   23.344   37.961  1.00   4.54
ATOM   1041  C    SER  146     -33.561   22.389   38.160  1.00   5.95
ATOM   1042  O    SER  146     -33.513   21.305   37.566  1.00   6.69
ATOM   1043  CB   SER  146     -32.609   23.870   36.500  1.00   4.69
```

```
ATOM   1044  OG   SER  146    -31.487  24.440  35.945  1.00   7.80
ATOM   1045  N    TYR  147    -34.584  22.813  38.888  1.00   4.96
ATOM   1046  OH   TYR  147    -34.686  16.409  41.718  1.00  15.17
ATOM   1047  CD2  TYR  147    -36.809  19.212  40.614  1.00   8.25
ATOM   1048  CE2  TYR  147    -36.419  17.910  40.955  1.00  10.83
ATOM   1049  CZ   TYR  147    -35.130  17.695  41.413  1.00  13.00
ATOM   1050  CE1  TYR  147    -34.196  18.722  41.524  1.00   8.41
ATOM   1051  CD1  TYR  147    -34.601  20.028  41.200  1.00   7.28
ATOM   1052  CG   TYR  147    -35.885  20.262  40.762  1.00   6.98
ATOM   1053  CB   TYR  147    -36.258  21.677  40.422  1.00   5.48
ATOM   1054  CA   TYR  147    -35.875  22.091  39.028  1.00   5.55
ATOM   1055  C    TYR  147    -36.829  23.167  38.409  1.00   6.41
ATOM   1056  O    TYR  147    -36.859  24.306  38.918  1.00   6.54
ATOM   1057  N    ILE  148    -37.559  22.845  37.365  1.00   5.67
ATOM   1058  CA   ILE  148    -38.454  23.821  36.710  1.00   6.64
ATOM   1059  C    ILE  148    -39.776  23.154  36.317  1.00   6.20
ATOM   1060  O    ILE  148    -39.743  21.993  35.834  1.00   6.60
ATOM   1061  CB   ILE  148    -37.661  24.408  35.475  1.00   8.25
ATOM   1062  CG1  ILE  148    -38.445  25.567  34.843  1.00  10.19
ATOM   1063  CG2  ILE  148    -37.269  23.309  34.443  1.00  11.02
ATOM   1064  CD1  ILE  148    -37.739  26.438  33.738  1.00  11.12
ATOM   1065  N    SER  149    -40.878  23.912  36.472  1.00   6.67
ATOM   1066  OG   SER  149    -42.874  22.350  38.136  1.00  15.36
ATOM   1067  CB   SER  149    -43.209  23.415  37.231  1.00   9.17
ATOM   1068  CA   SER  149    -42.219  23.396  36.098  1.00   7.08
ATOM   1069  C    SER  149    -42.712  24.364  35.000  1.00   7.85
ATOM   1070  O    SER  149    -43.087  25.496  35.341  1.00   8.98
ATOM   1071  N    GLY  150    -42.632  23.897  33.754  1.00  10.00
ATOM   1072  CA   GLY  150    -43.066  24.798  32.663  1.00  11.86
ATOM   1073  C    GLY  150    -41.990  25.883  32.482  1.00   8.97
ATOM   1074  O    GLY  150    -40.850  25.591  32.148  1.00  12.79
ATOM   1075  N    THR  151    -42.463  27.096  32.745  1.00   9.09
ATOM   1076  CG2  THR  151    -42.428  29.087  30.347  1.00  13.40
ATOM   1077  OG1  THR  151    -43.398  29.844  32.497  1.00  13.13
ATOM   1078  CB   THR  151    -42.170  29.426  31.816  1.00  11.88
ATOM   1079  CA   THR  151    -41.527  28.257  32.661  1.00  10.61
ATOM   1080  C    THR  151    -41.196  28.758  34.085  1.00   9.76
ATOM   1081  O    THR  151    -40.553  29.810  34.179  1.00  10.13
ATOM   1082  N    GLN  152    -41.628  28.099  35.157  1.00   6.87
ATOM   1083  CA   GLN  152    -41.440  28.600  36.494  1.00   7.20
ATOM   1084  C    GLN  152    -40.304  27.909  37.266  1.00   8.56
ATOM   1085  O    GLN  152    -40.488  26.681  37.461  1.00  12.38
ATOM   1086  CB   GLN  152    -42.770  28.493  37.286  1.00   6.03
ATOM   1087  CG   GLN  152    -43.935  29.238  36.607  1.00   9.11
ATOM   1088  CD   GLN  152    -43.668  30.705  36.459  1.00   7.44
ATOM   1089  OE1  GLN  152    -43.411  31.422  37.422  1.00  11.18
ATOM   1090  NE2  GLN  152    -43.686  31.229  35.247  1.00  15.32
ATOM   1091  N    ALA  153    -39.288  28.691  37.696  1.00   7.16
ATOM   1092  CA   ALA  153    -38.166  28.065  38.442  1.00   6.99
ATOM   1093  C    ALA  153    -38.696  27.572  39.786  1.00   6.78
ATOM   1094  O    ALA  153    -39.432  28.329  40.450  1.00   8.03
ATOM   1095  CB   ALA  153    -37.062  29.133  38.567  1.00   6.81
ATOM   1096  N    GLN  154    -38.383  26.349  40.198  1.00   4.41
ATOM   1097  CA   GLN  154    -38.827  25.782  41.460  1.00   6.90
```

```
ATOM   1098  C    GLN  154     -37.692  25.687  42.494  1.00   7.22
ATOM   1099  O    GLN  154     -37.931  26.098  43.640  1.00   7.22
ATOM   1100  CB   GLN  154     -39.459  24.374  41.221  1.00   6.12
ATOM   1101  CG   GLN  154     -40.644  24.402  40.211  1.00   6.24
ATOM   1102  CD   GLN  154     -41.732  25.321  40.671  1.00   9.04
ATOM   1103  OE1  GLN  154     -42.271  25.234  41.795  1.00   9.56
ATOM   1104  NE2  GLN  154     -42.164  26.267  39.859  1.00   4.50
ATOM   1105  N    GLY  155     -36.547  25.153  42.078  1.00   7.56
ATOM   1106  CA   GLY  155     -35.475  24.954  43.098  1.00   7.31
ATOM   1107  C    GLY  155     -34.202  24.370  42.501  1.00   7.69
ATOM   1108  O    GLY  155     -34.029  24.335  41.280  1.00   7.17
ATOM   1109  N    VAL  156     -33.252  24.073  43.370  1.00   6.91
ATOM   1110  CA   VAL  156     -31.925  23.515  42.968  1.00   7.24
ATOM   1111  C    VAL  156     -31.760  22.136  43.631  1.00   5.91
ATOM   1112  O    VAL  156     -32.096  21.942  44.815  1.00   6.78
ATOM   1113  CB   VAL  156     -30.786  24.527  43.154  1.00   6.19
ATOM   1114  CG1  VAL  156     -31.048  25.862  42.407  1.00   5.61
ATOM   1115  CG2  VAL  156     -30.409  24.754  44.616  1.00   8.17
ATOM   1116  N    THR  157     -31.186  21.164  42.911  1.00   3.82
ATOM   1117  CG2  THR  157     -30.184  17.395  42.515  1.00   4.16
ATOM   1118  OG1  THR  157     -30.991  19.138  41.073  1.00   8.01
ATOM   1119  CB   THR  157     -30.243  18.893  42.293  1.00   3.37
ATOM   1120  CA   THR  157     -30.971  19.799  43.383  1.00   4.97
ATOM   1121  C    THR  157     -30.083  19.754  44.627  1.00   5.89
ATOM   1122  O    THR  157     -28.979  20.281  44.589  1.00   5.74
ATOM   1123  N    SER  158     -30.588  19.070  45.635  1.00   5.99
ATOM   1124  CA   SER  158     -29.830  18.914  46.876  1.00   7.64
ATOM   1125  C    SER  158     -29.316  17.473  46.969  1.00  10.26
ATOM   1126  O    SER  158     -28.087  17.229  47.132  1.00  10.04
ATOM   1127  CB   SER  158     -30.619  19.304  48.134  1.00   8.30
ATOM   1128  OG   SER  158     -29.853  18.975  49.296  1.00   9.39
ATOM   1129  N    GLY  159     -30.150  16.443  46.900  1.00   9.83
ATOM   1130  CA   GLY  159     -29.635  15.060  47.040  1.00   9.90
ATOM   1131  C    GLY  159     -30.756  14.048  47.006  1.00  12.82
ATOM   1132  O    GLY  159     -31.878  14.478  46.680  1.00  13.31
ATOM   1133  N    GLY  160     -30.510  12.792  47.352  1.00  12.00
ATOM   1134  CA   GLY  160     -31.646  11.846  47.257  1.00  12.56
ATOM   1135  C    GLY  160     -31.091  10.410  47.219  1.00  15.35
ATOM   1136  O    GLY  160     -29.988  10.197  47.741  1.00  15.70
ATOM   1137  N    SER  161     -31.869   9.497  46.679  1.00  13.10
ATOM   1138  OG   SER  161     -33.410   7.381  47.752  1.00  18.73
ATOM   1139  CB   SER  161     -31.996   7.324  47.833  1.00  16.84
ATOM   1140  CA   SER  161     -31.379   8.089  46.671  1.00  14.66
ATOM   1141  C    SER  161     -31.670   7.448  45.325  1.00  13.50
ATOM   1142  O    SER  161     -32.491   8.066  44.640  1.00  13.10
ATOM   1143  N    GLY  162     -31.078   6.310  45.040  1.00  11.84
ATOM   1144  CA   GLY  162     -31.318   5.641  43.734  1.00  12.53
ATOM   1145  C    GLY  162     -30.457   6.331  42.672  1.00  12.12
ATOM   1146  O    GLY  162     -29.545   7.088  42.957  1.00  11.79
ATOM   1147  N    ASN  163     -30.786   6.068  41.407  1.00  10.66
ATOM   1148  CA   ASN  163     -30.058   6.588  40.269  1.00   8.29
ATOM   1149  C    ASN  163     -31.033   6.671  39.088  1.00  11.02
ATOM   1150  O    ASN  163     -32.220   6.293  39.233  1.00  10.33
ATOM   1151  CB   ASN  163     -28.827   5.741  39.950  1.00  10.88
```

```
ATOM   1152  CG   ASN   163    -29.238    4.312   39.578  1.00  14.23
ATOM   1153  OD1  ASN   163    -29.966    3.979   38.660  1.00  11.31
ATOM   1154  ND2  ASN   163    -28.649    3.362   40.334  1.00  18.48
ATOM   1155  N    CYS   164    -30.499    7.132   37.956  1.00  10.86
ATOM   1156  CA   CYS   164    -31.420    7.271   36.806  1.00  11.83
ATOM   1157  C    CYS   164    -31.687    6.006   35.998  1.00  13.69
ATOM   1158  O    CYS   164    -32.428    6.145   34.993  1.00  15.15
ATOM   1159  CB   CYS   164    -31.100    8.500   35.971  1.00  10.31
ATOM   1160  SG   CYS   164    -31.448   10.097   36.795  1.00   9.57
ATOM   1161  N    ARG   165    -31.110    4.919   36.364  1.00  11.68
ATOM   1162  NH2  ARG   165    -26.089    2.173   38.339  1.00  59.15
ATOM   1163  NH1  ARG   165    -25.617    4.096   37.196  1.00  58.35
ATOM   1164  CZ   ARG   165    -26.258    2.909   37.212  1.00  55.39
ATOM   1165  NE   ARG   165    -27.054    2.356   36.310  1.00  47.93
ATOM   1166  CD   ARG   165    -27.631    2.632   35.037  1.00  40.44
ATOM   1167  CG   ARG   165    -28.933    3.381   34.944  1.00  31.56
ATOM   1168  CB   ARG   165    -30.065    2.765   35.785  1.00  18.33
ATOM   1169  CA   ARG   165    -31.324    3.621   35.703  1.00  17.34
ATOM   1170  C    ARG   165    -32.498    2.928   36.433  1.00  14.57
ATOM   1171  O    ARG   165    -33.499    2.588   35.782  1.00  15.39
ATOM   1172  N    THR   166    -32.347    2.784   37.751  1.00  12.62
ATOM   1173  CG2  THR   166    -31.557    0.620   39.350  1.00  18.19
ATOM   1174  OG1  THR   166    -32.296    2.562   40.679  1.00  17.67
ATOM   1175  CB   THR   166    -32.716    1.474   39.795  1.00  16.75
ATOM   1176  CA   THR   166    -33.407    2.140   38.540  1.00  13.18
ATOM   1177  C    THR   166    -34.528    3.049   39.012  1.00  15.18
ATOM   1178  O    THR   166    -35.581    2.528   39.436  1.00  16.50
ATOM   1179  N    GLY   167    -34.296    4.347   39.040  1.00  13.17
ATOM   1180  CA   GLY   167    -35.255    5.345   39.536  1.00  13.42
ATOM   1181  C    GLY   167    -34.815    5.663   40.997  1.00  14.50
ATOM   1182  O    GLY   167    -33.957    4.993   41.596  1.00  13.35
ATOM   1183  N    GLY   168    -35.330    6.773   41.562  1.00  14.99
ATOM   1184  CA   GLY   168    -34.923    7.118   42.940  1.00  12.40
ATOM   1185  C    GLY   168    -35.852    8.241   43.371  1.00  15.29
ATOM   1186  O    GLY   168    -36.909    8.509   42.754  1.00  14.71
ATOM   1187  N    THR   169    -35.422    8.845   44.471  1.00  14.65
ATOM   1188  CG2  THR   169    -37.341   10.701   47.345  1.00  11.85
ATOM   1189  OG1  THR   169    -37.698    8.540   46.281  1.00  16.91
ATOM   1190  CB   THR   169    -36.711    9.582   46.529  1.00  14.83
ATOM   1191  CA   THR   169    -36.177    9.973   45.077  1.00  13.13
ATOM   1192  C    THR   169    -35.165   11.121   45.248  1.00  11.43
ATOM   1193  O    THR   169    -34.007   10.807   45.611  1.00  11.62
ATOM   1194  N    THR   170    -35.621   12.315   44.946  1.00   8.52
ATOM   1195  CG2  THR   170    -33.232   12.956   43.075  1.00   6.44
ATOM   1196  OG1  THR   170    -35.355   14.161   43.068  1.00  19.35
ATOM   1197  CB   THR   170    -34.090   13.942   43.798  1.00  12.63
ATOM   1198  CA   THR   170    -34.667   13.406   45.165  1.00   8.99
ATOM   1199  C    THR   170    -35.363   14.555   45.880  1.00  11.07
ATOM   1200  O    THR   170    -36.582   14.758   45.736  1.00  12.91
ATOM   1201  N    PHE   171    -34.531   15.291   46.609  1.00   9.07
ATOM   1202  CD2  PHE   171    -36.450   15.430   50.154  1.00  12.37
ATOM   1203  CE2  PHE   171    -37.017   14.281   50.750  1.00  12.72
ATOM   1204  CZ   PHE   171    -36.332   13.053   50.718  1.00  14.13
ATOM   1205  CE1  PHE   171    -35.064   12.901   50.136  1.00  11.85
```

```
ATOM   1206  CD1 PHE  171     -34.501  14.041  49.547  1.00 12.01
ATOM   1207  CG  PHE  171     -35.187  15.262  49.538  1.00 14.42
ATOM   1208  CB  PHE  171     -34.500  16.430  48.855  1.00  8.65
ATOM   1209  CA  PHE  171     -34.946  16.484  47.353  1.00 10.31
ATOM   1210  C   PHE  171     -34.276  17.746  46.736  1.00  9.69
ATOM   1211  O   PHE  171     -33.096  17.749  46.336  1.00 10.28
ATOM   1212  N   TYR  172     -35.022  18.818  46.721  1.00  6.76
ATOM   1213  OH  TYR  172     -40.405  22.042  43.789  1.00 10.33
ATOM   1214  CD2 TYR  172     -37.368  19.978  44.053  1.00  7.13
ATOM   1215  CE2 TYR  172     -38.680  20.393  43.754  1.00  9.56
ATOM   1216  CZ  TYR  172     -39.128  21.645  44.088  1.00 11.06
ATOM   1217  CE1 TYR  172     -38.255  22.544  44.740  1.00  7.89
ATOM   1218  CD1 TYR  172     -36.943  22.125  44.984  1.00  5.66
ATOM   1219  CG  TYR  172     -36.496  20.849  44.693  1.00  5.21
ATOM   1220  CB  TYR  172     -35.049  20.462  44.892  1.00  6.84
ATOM   1221  CA  TYR  172     -34.465  20.077  46.256  1.00  7.19
ATOM   1222  C   TYR  172     -34.711  21.217  47.245  1.00  6.71
ATOM   1223  O   TYR  172     -35.673  21.172  48.064  1.00  8.96
ATOM   1224  N   GLN  173     -33.781  22.185  47.157  1.00  5.53
ATOM   1225  NE2 GLN  173     -33.746  26.714  50.033  1.00  6.96
ATOM   1226  OE1 GLN  173     -32.289  25.169  50.891  1.00 10.23
ATOM   1227  CD  GLN  173     -32.795  25.753  49.933  1.00  9.42
ATOM   1228  CG  GLN  173     -32.411  25.493  48.482  1.00  3.75
ATOM   1229  CB  GLN  173     -32.463  24.037  48.054  1.00  8.35
ATOM   1230  CA  GLN  173     -33.883  23.428  47.962  1.00  5.17
ATOM   1231  C   GLN  173     -34.741  24.402  47.187  1.00  6.61
ATOM   1232  O   GLN  173     -34.469  24.693  45.967  1.00  7.86
ATOM   1233  N   GLU  174     -35.814  24.921  47.782  1.00  6.75
ATOM   1234  OE2 GLU  174     -40.122  25.837  46.396  1.00  8.25
ATOM   1235  OE1 GLU  174     -40.521  23.919  47.243  1.00 10.88
ATOM   1236  CD  GLU  174     -39.899  24.969  47.265  1.00 10.25
ATOM   1237  CG  GLU  174     -38.863  25.164  48.362  1.00  8.85
ATOM   1238  CB  GLU  174     -37.861  26.313  48.083  1.00  9.36
ATOM   1239  CA  GLU  174     -36.686  25.892  47.108  1.00  7.86
ATOM   1240  C   GLU  174     -35.933  27.178  46.774  1.00  8.69
ATOM   1241  O   GLU  174     -35.082  27.712  47.515  1.00  9.98
ATOM   1242  N   VAL  175     -36.198  27.769  45.591  1.00  8.61
ATOM   1243  CG2 VAL  175     -34.568  29.950  43.032  1.00 11.90
ATOM   1244  CG1 VAL  175     -36.989  29.512  42.968  1.00 13.78
ATOM   1245  CB  VAL  175     -35.652  29.062  43.589  1.00 13.52
ATOM   1246  CA  VAL  175     -35.605  29.022  45.144  1.00  8.03
ATOM   1247  C   VAL  175     -36.196  30.221  45.869  1.00  8.45
ATOM   1248  O   VAL  175     -35.453  31.199  46.161  1.00  8.96
ATOM   1249  N   THR  176     -37.454  30.220  46.297  1.00  9.06
ATOM   1250  CG2 THR  176     -40.371  32.282  47.869  1.00 18.26
ATOM   1251  OG1 THR  176     -40.343  30.692  46.091  1.00 18.82
ATOM   1252  CB  THR  176     -39.648  31.030  47.350  1.00 15.35
ATOM   1253  CA  THR  176     -38.133  31.355  46.965  1.00 10.08
ATOM   1254  C   THR  176     -37.370  32.053  48.082  1.00 12.75
ATOM   1255  O   THR  176     -37.203  33.295  48.105  1.00 12.78
ATOM   1256  N   PRO  177     -36.827  31.275  49.019  1.00 13.60
ATOM   1257  CA  PRO  177     -36.059  31.831  50.137  1.00 14.56
ATOM   1258  C   PRO  177     -34.832  32.550  49.634  1.00 14.53
ATOM   1259  O   PRO  177     -34.405  33.537  50.205  1.00 14.33
```

```
ATOM   1260  CB  PRO  177     -35.684  30.599  50.967  1.00 15.59
ATOM   1261  CG  PRO  177     -36.607  29.488  50.587  1.00 15.55
ATOM   1262  CD  PRO  177     -37.028  29.818  49.155  1.00 14.17
ATOM   1263  N   MET  178     -34.177  32.085  48.557  1.00 11.26
ATOM   1264  CE  MET  178     -31.755  28.533  46.007  1.00 19.72
ATOM   1265  SD  MET  178     -30.708  29.927  46.237  1.00 22.73
ATOM   1266  CG  MET  178     -31.639  30.737  47.651  1.00 17.28
ATOM   1267  CB  MET  178     -32.343  31.919  46.980  1.00  9.92
ATOM   1268  CA  MET  178     -32.991  32.789  48.077  1.00 11.19
ATOM   1269  C   MET  178     -33.372  34.163  47.572  1.00 14.99
ATOM   1270  O   MET  178     -32.631  35.161  47.724  1.00 16.24
ATOM   1271  N   VAL  179     -34.492  34.273  46.870  1.00 12.66
ATOM   1272  CG2 VAL  179     -35.871  34.516  44.214  1.00 11.56
ATOM   1273  CG1 VAL  179     -36.995  36.540  45.154  1.00 16.31
ATOM   1274  CB  VAL  179     -36.242  35.254  45.495  1.00 14.06
ATOM   1275  CA  VAL  179     -34.973  35.549  46.347  1.00 14.10
ATOM   1276  C   VAL  179     -35.411  36.462  47.516  1.00 17.87
ATOM   1277  O   VAL  179     -35.152  37.674  47.535  1.00 18.01
ATOM   1278  N   ASN  180     -36.139  35.872  48.451  1.00 17.87
ATOM   1279  ND2 ASN  180     -39.996  35.004  49.792  1.00 34.66
ATOM   1280  OD1 ASN  180     -39.173  36.590  48.442  1.00 26.20
ATOM   1281  CG  ASN  180     -39.030  35.860  49.435  1.00 27.22
ATOM   1282  CB  ASN  180     -37.798  35.850  50.334  1.00 22.46
ATOM   1283  CA  ASN  180     -36.683  36.628  49.576  1.00 21.81
ATOM   1284  C   ASN  180     -35.663  37.122  50.588  1.00 22.21
ATOM   1285  O   ASN  180     -35.786  38.276  51.007  1.00 25.30
ATOM   1286  N   SER  181     -34.775  36.258  50.952  1.00 20.13
ATOM   1287  OG  SER  181     -34.362  34.891  53.477  1.00 46.23
ATOM   1288  CB  SER  181     -33.268  35.230  52.620  1.00 29.26
ATOM   1289  CA  SER  181     -33.740  36.530  51.921  1.00 20.62
ATOM   1290  C   SER  181     -32.474  37.109  51.355  1.00 20.10
ATOM   1291  O   SER  181     -31.914  37.915  52.104  1.00 20.08
ATOM   1292  N   TRP  182     -32.042  36.665  50.186  1.00 17.06
ATOM   1293  CD2 TRP  182     -28.744  33.771  49.582  1.00 20.91
ATOM   1294  CE3 TRP  182     -28.470  33.240  48.331  1.00 15.11
ATOM   1295  CZ3 TRP  182     -27.853  31.999  48.269  1.00 15.36
ATOM   1296  CH2 TRP  182     -27.529  31.313  49.436  1.00 15.65
ATOM   1297  CZ2 TRP  182     -27.769  31.806  50.713  1.00 19.64
ATOM   1298  CE2 TRP  182     -28.381  33.057  50.742  1.00 24.59
ATOM   1299  NE1 TRP  182     -28.738  33.820  51.828  1.00 27.77
ATOM   1300  CD1 TRP  182     -29.323  34.986  51.373  1.00 29.42
ATOM   1301  CG  TRP  182     -29.377  35.009  50.004  1.00 22.91
ATOM   1302  CB  TRP  182     -29.884  36.098  49.127  1.00 20.07
ATOM   1303  CA  TRP  182     -30.771  37.210  49.681  1.00 14.46
ATOM   1304  C   TRP  182     -30.992  38.306  48.680  1.00 14.45
ATOM   1305  O   TRP  182     -30.007  38.974  48.321  1.00 16.23
ATOM   1306  N   GLY  183     -32.203  38.445  48.182  1.00 13.61
ATOM   1307  CA  GLY  183     -32.431  39.519  47.179  1.00 13.59
ATOM   1308  C   GLY  183     -31.864  39.105  45.800  1.00 12.98
ATOM   1309  O   GLY  183     -31.478  40.015  45.005  1.00 11.51
ATOM   1310  N   VAL  184     -31.805  37.788  45.559  1.00 12.12
ATOM   1311  CG2 VAL  184     -31.741  34.892  44.375  1.00 20.41
ATOM   1312  CG1 VAL  184     -29.458  35.739  44.931  1.00 20.83
ATOM   1313  CB  VAL  184     -30.729  35.966  44.088  1.00 14.52
```

```
ATOM   1314  CA   VAL  184   -31.288  37.397  44.216  1.00  13.35
ATOM   1315  C    VAL  184   -32.431  37.647  43.201  1.00  13.39
ATOM   1316  O    VAL  184   -33.619  37.490  43.538  1.00  13.79
ATOM   1317  N    ARG  185   -32.041  37.991  41.974  1.00  11.85
ATOM   1318  NH2  ARG  185   -31.382  44.754  43.270  1.00  30.49
ATOM   1319  NH1  ARG  185   -30.633  44.370  41.110  1.00  29.76
ATOM   1320  CZ   ARG  185   -31.320  43.982  42.177  1.00  30.81
ATOM   1321  NE   ARG  185   -31.986  42.816  42.217  1.00  27.27
ATOM   1322  CD   ARG  185   -31.978  41.937  41.036  1.00  23.48
ATOM   1323  CG   ARG  185   -32.959  40.840  41.410  1.00  19.17
ATOM   1324  CB   ARG  185   -32.789  39.732  40.349  1.00  14.23
ATOM   1325  CA   ARG  185   -32.980  38.274  40.869  1.00  11.15
ATOM   1326  C    ARG  185   -32.746  37.319  39.703  1.00   8.87
ATOM   1327  O    ARG  185   -31.721  37.472  39.065  1.00   8.01
ATOM   1328  N    LEU  186   -33.644  36.370  39.444  1.00   9.17
ATOM   1329  CA   LEU  186   -33.463  35.447  38.328  1.00   9.78
ATOM   1330  C    LEU  186   -33.503  36.225  36.995  1.00  10.75
ATOM   1331  O    LEU  186   -34.316  37.132  36.787  1.00  10.04
ATOM   1332  CB   LEU  186   -34.648  34.435  38.305  1.00   8.11
ATOM   1333  CG   LEU  186   -34.760  33.549  39.546  1.00  16.49
ATOM   1334  CD1  LEU  186   -35.699  32.375  39.276  1.00  14.66
ATOM   1335  CD2  LEU  186   -33.400  32.928  39.887  1.00  16.56
ATOM   1336  N    ARG  187   -32.652  35.750  36.102  1.00   7.79
ATOM   1337  NH2  ARG  187   -30.740  39.908  29.630  1.00  46.94
ATOM   1338  NH1  ARG  187   -29.232  39.169  31.188  1.00  49.29
ATOM   1339  CZ   ARG  187   -30.477  39.174  30.718  1.00  44.29
ATOM   1340  NE   ARG  187   -31.443  38.474  31.338  1.00  36.97
ATOM   1341  CD   ARG  187   -31.199  37.750  32.536  1.00  28.81
ATOM   1342  CG   ARG  187   -31.219  36.300  32.604  1.00  27.43
ATOM   1343  CB   ARG  187   -31.340  35.889  34.068  1.00  12.14
ATOM   1344  CA   ARG  187   -32.653  36.298  34.718  1.00   9.41
ATOM   1345  C    ARG  187   -33.901  35.672  34.023  1.00  10.55
ATOM   1346  O    ARG  187   -34.139  34.427  33.990  1.00  10.23
ATOM   1347  N    THR  188   -34.769  36.530  33.478  1.00   9.32
ATOM   1348  CA   THR  188   -35.996  36.175  32.723  1.00  10.52
ATOM   1349  C    THR  188   -35.889  36.694  31.263  1.00  11.51
ATOM   1350  O    THR  188   -34.786  37.058  30.810  1.00  10.45
ATOM   1351  CB   THR  188   -37.361  36.593  33.422  1.00   7.88
ATOM   1352  OG1  THR  188   -37.427  38.057  33.443  1.00   7.10
ATOM   1353  CG2  THR  188   -37.581  36.118  34.850  1.00   8.10
ATOM   1354  OXT  THR  188   -36.851  36.451  30.513  1.00  13.52
```

Fig. 2

PROTEASE VARIANTS

CROSS-REFERENCE TO RELATED APPLICATIONS

This application is a continuation of U.S. application Ser. No. 10/574,554 filed on Apr. 3, 2006, now U.S. Pat. No. 7,892,808, which is a 35 U.S.C. 371 national application of PCT/DK2004/000688 filed Oct. 8, 2004, which claims priority or the benefit under 35 U.S.C. 119 of Danish application nos. PA 2003 01494 and PA 2004 00333 filed Oct. 10, 2003 and Mar. 1, 2004, respectively, and U.S. provisional application nos. 60/510,450 and 60/549,347 filed Oct. 10, 2003 and Mar. 2, 2004, respectively, the contents of which are fully incorporated herein by reference.

FIELD OF THE INVENTION

The present invention relates to a novel protease 3D structure, as well as variants of a parent protease, in particular variants of amended properties, such as improved thermostability and/or amended temperature activity profile. The invention also relates to DNA sequences encoding such variants, their production in a recombinant host cell, as well as methods of using the variants, in particular within the field of animal feed and detergents. The invention furthermore relates to methods of generating and preparing protease variants of amended properties. Preferred parent proteases are *Nocardiopsis* proteases, such as proteases comprising the mature peptide parts of SEQ ID NOs: 2, 4, 6, 8, 10, and 21.

BACKGROUND OF THE INVENTION

Protease sequences derived from strains of *Nocardiopsis* are disclosed in WO 88/03947, WO 01/58276, and DK 1996 00013 ("Protease 10," SEQ ID NOs: 1-2).

JP 2003284571-A discloses, as SEQ ID NOs: 2 and 1, the amino acid sequence and the corresponding DNA sequence, respectively, of a protease derived from *Nocardiopsis* sp. TOA-1 (FERM P-18676). The sequences have been entered in the GENESEQ database as GENESEQP no. ADF43564, and GENESEQN no. ADF43563, respectively.

JP 2-255081-A discloses a protease derived from *Nocardiopsis* sp. strain OPC-210 (FERM P-10508), however without sequence information. The strain is no longer available, as the deposit was withdrawn.

DD 20043218 discloses a proteolytic preparation derived from *Nocardiopsis dassonvillei* strain ZIMET 43647, however without sequence information. The strain appears to be no longer available.

Additional *Nocardiopsis* protease sequences are disclosed in PCT/DK04/000433 ("Protease 08," SEQ ID NOs: 9-10); PCT/DK04/000434 ("Protease 11," SEQ ID NOs: 5-6 herein); PCT/DK04/000432 ("Protease 18," SEQ ID NOs: 3-4); and PCT/DK04/000435 ("Protease 35," SEQ ID NOs: 7-8).

It is an object of the present invention to provide alternative proteases, in particular for use in animal feed and/or detergents, in particular novel and improved protease variants, preferably of amended properties, such as improved thermostability and/or a higher or lower optimum temperature.

SUMMARY OF THE INVENTION

The present invention relates to a variant of a parent protease, comprising a substitution in at least one position of at least one region selected from the group of regions consisting of: 6-18; 22-28; 32-39; 42-58; 62-63; 66-76; 78-100; 103-106; 111-114; 118-131; 134-136; 139-141; 144-151; 155-156; 160-176; 179-181; and 184-188; wherein
  (a) the variant has protease activity; and
  (b) each position corresponds to a position of amino acids 1 to 188 of SEQ ID NO: 2; and
  (c) the variant has a percentage of identity to amino acids 1 to 188 of SEQ ID NO: 2 of at least 60%.

The present invention also relates to isolated nucleic acid sequences encoding the protease variant and to nucleic acid constructs, vectors, and host cells comprising the nucleic acid sequences as well as methods for producing and using the protease variants.

BRIEF DESCRIPTION OF THE FIGURES

FIG. 1 is a multiple alignment of Protease 10, Protease 18, Protease 11, Protease 35 and Protease 08 (the mature peptide parts of SEQ ID NOs: 2, 4, 6, 8 and 10, respectively), also including a protease variant of the invention, viz. Protease 22 (amino acids 1-188 of SEQ ID NO: 21); and FIG. 2 provides the coordinates of the novel 3D structure of Protease 10 (amino acids 1 to 188 of SEQ ID NO: 2) derived from *Nocardiopsis* sp. NRRL 18262.

DETAILED DESCRIPTION OF THE INVENTION

Three-Dimensional Structure of Protease 10

The structure of Protease 10 was solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure at 2.2 Å resolution using the isomorphous replacement method are given in FIG. 2 in standard PDB format (Protein Data Bank, Brookhaven National Laboratory, Brookhaven, Conn.). The PDB file of FIG. 2 relates to the mature peptide part of Protease 10 corresponding to residues 1-188 of SEQ ID NO: 2.

Molecular Dynamics (MD)

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Using the programs CHARMM (Accelrys) and NAMD (University of Illinois at Urbana-Champaign) the Protease 10 structure described above was subjected to MD at 300 and 400K. Starting from the coordinates of FIG. 2 hydrogen and missing heavy atoms were built using CHARMM procedures HBUILD and IC BUILD respectively. Then the structure was minimized using CHARMM Conjugate Gradients (CONJ) minimization procedure for a total of 200 steps. The protein was then put on a 70×70×70 Angstrom box and solvated with TIP3 water molecules. A total of 11124 water molecules were added and then minimized, keeping the protein coordinates fixed, using CHARMM Adopted Basis Newton Raphson (ABNR) minimization procedure for 20000 steps. The system was then heated to the desired temperature at a rate of 1K every 100 steps using the NAMD software. After an equilibration of 50 picoseconds, an NVE ensemble MD was run for 1 nanosecond, both steps done with the software NAMD. A cut-off of 12 Angstrom was used for the non-bonded interactions. Periodic boundary conditions were used after the solvation step and for all the subsequent ones. The isotropic root mean square (RMS) fluctuations were calculated with the CHARMM procedure COOR DYNA.

The following suggested regions for mutagenesis result from MD simulations: From residue 160 to 170, from residue 78 to 90, from residue 43 to 50, from residue 66 to 75, and from residue 22 to 28.

Strategy for Preparing Variants

Regions of amino acid residues, as well as individual amino acid substitutions, were suggested for mutagenesis based on the 3D-structure of FIG. 2 and the alignment of the five known proteases (upper five rows of FIG. 1), mainly with a view to improving thermostability.

The following regions were suggested, cf. claim 1: 6-18; 22-28; 32-39; 42-58; 62-63; 66-76; 78-100; 103-106; 111-114; 118-131; 134-136; 139-141; 144-151; 155-156; 160-176; 179-181; and 184-188.

At least one of the following positions of the above regions are preferably subjected to mutagenesis, cf. claim 3; 6; 7; 8; 9; 10; 12; 13; 16; 17; 18; 22; 23; 24; 25; 26; 27; 28; 32; 33; 37; 38; 39; 42; 43; 44; 45; 46; 47; 48; 49; 50; 51; 52; 53; 54; 55; 56; 58; 62; 63; 66; 67; 68; 69; 70; 71; 72; 73; 74; 75; 76; 78; 79; 80; 81; 82; 83; 84; 85; 86; 87; 88; 89; 90; 91; 92; 93; 94; 95; 96; 97; 98; 99; 100; 103; 105; 106; 111; 113; 114; 118; 120; 122; 124; 125; 127; 129; 130; 131; 134; 135; 136; 139; 140; 141; 144; 145; 146; 147; 148; 149; 150; 151; 155; 156; 160; 161; 162; 163; 164; 165; 166; 167; 168; 169; 170; 171; 172; 173; 174; 175; 176; 179; 180; 181; 184; 185; 186; 187; and/or 188.

Contemplated specific variants are listed in the claims, viz. variants of Protease 10, Protease 18, Protease 11, Protease 35 as well as Protease 08 in claims 4 and 15; variants of Protease 10 in claim 16; variants of Protease 18 in claim 17; variants of Protease 11 in claim 18; variants of Protease 35 in claim 19; and variants of Protease 08 in claim 20.

The various concepts underlying the invention are also reflected in the claims as follows:

Stabilization by disulfide-bridges in claims 5 and 6; proline-stabilization in claims 7-8; substitution of exposed neutral residues with negatively charged residues in claims 9-10; substitution of exposed neutral residues with positively charged residues in claims 11-12; substitution of small residues with bulkier residues inside the protein in claim 13; and regions proposed for mutagenesis following MD simulations in claim 14.

The term "at least one" means "one or more," viz., e.g. in the context of regions: One, two, three, four, five, six, seven, eight, nine, ten, eleven, twelve, thirteen, fourteen, fifteen, sixteen, or seventeen; or, in the context of positions or substitutions: One, two, three, four, five, and so on, up to e.g. ninety.

In a particular embodiment, the number of regions proposed for and/or subjected to mutagenesis is at least one, two, three, four, five, six, seven, eight, nine, ten, eleven, twelve, thirteen, fourteen, fifteen, sixteen, or at least seventeen.

In another particular embodiment, the number of regions proposed for and/or subjected to mutagenesis is no more than one, two, three, four, five, six, seven, eight, nine, ten, eleven, twelve, thirteen, fourteen, fifteen, sixteen, or no more than seventeen.

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at chem..qmw.ac.uk/iubmb/enzvme/index.html.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In particular embodiments, the parent proteases and/or the protease variants of the invention and for use according to the invention are selected from the group consisting of:

(a) Proteases belonging to the EC 3.4.-.- enzyme group;

(b) Serine proteases belonging to the S group of the above Handbook;

(c1) Serine proteases of peptidase family S2A; and (c2) Serine proteases of peptidase family S1E as described in Biochem.J. 290:205-218 (1993) and in MEROPS protease database, release 6.20, Mar. 24, 2003, (merops.ac.uk). The database is described in Rawlings, N.D., O'Brien, E. A. & Barrett, A.J. (2002) MEROPS: the protease database. Nucleic Acids Res. 30, 343-346.

For determining whether a given protease is a Serine protease, and a family S2A protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Examples of protease substrates are casein, such as Azurine-Crosslinked Casein (AZCL-casein). Examples of suitable protease assays are described in the experimental part.

Parent Protease

The parent protease is a protease from which the protease variant is, or can be, derived. For the present purposes, any protease can be used as the parent protease, as long as the resulting protease variant is homologous to Protease 10, i.e. the protease derived from *Nocardiopsis* sp. NRRL 18262 and comprising amino acids 1-188 of SEQ ID NO: 2.

In a particular embodiment the parent protease is also homologous to Protease 10.

In the present context, homologous means having an identity of at least 60% to SEQ ID NO: 2, viz. amino acids 1-188 of the mature peptide part of Protease 10. Homology is determined as generally described below in the section entitled Amino Acid Homology.

The parent protease may be a wild-type or naturally occurring polypeptide, or an allelic variant thereof, or a fragment thereof that has protease acticity, in particular a mature part thereof. It may also be a variant thereof and/or a genetically engineered or synthetic polypeptide.

In a particular embodiment the wild-type parent protease is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species, such as *Nocardiopsis alba, Nocardiopsis antarctica, Nocardiopsis composta, Nocardiopsis dassonvillei, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis prasina, Nocardiopsis* sp., *Nocardiopsis synnemataformans, Nocardiopsis trehalosi, Nocardiopsis tropica, Nocardiopsis umidischolae*, or *Nocardiopsis xinjiangensis*.

Examples of such strains are: *Nocardiopsis alba* DSM 15647 (wild-type producer of Protease 08), *Nocardiopsis dassonvillei* NRRL 18133 (wild-type producer of Protease M58-1 described in WO 88/03947), *Nocardiopsis dassonvillei* subsp. *dassonvillei* DSM 43235 (wild-type producer of Protease 18), *Nocardiopsis prasina* DSM 15648 (wild-type producer of Protease 11), *Nocardiopsis prasina* DSM 15649 (wild-type producer of Protease 35), *Nocardiopsis* sp. NRRL 18262 (wild-type producer of Protease 10), *Nocardiopsis* sp. FERM P-18676 (described in JP 2003284571-A).

Strains of these species are accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL), e.g. Nocardiopsis dassonvillei subsp. *dassonvillei* DSM 43235 is publicly available from DSMZ (Deutsche Sammlung von Mikroorganismen und Zellkulturen GmbH, Braunschweig, Germany).

Furthermore, such polypeptides may be identified and obtained from other sources including microorganisms or DNA isolated from nature (e.g., soil, composts, water, etc.) using suitable probes. Techniques for isolating microorganisms or DNA from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The parent protease may be a mature part of any of the amino acid sequences referred to above. A mature part means a mature amino acid sequence and refers to that part of an amino acid sequence which remains after a potential signal peptide part and/or pro-peptide part has been cleaved off. The mature parts of each of the proteases Protease 08, 10, 11, 18, 22 and 35 are specified in the sequence listing.

The parent protease may also be a fragment of a specified amino acid sequence, viz. a polypeptide having one or more amino acids deleted from the amino and/or carboxyl terminus of this amino acid sequence. In one embodiment, a fragment contains at least 80, or at least 90, or at least 100, or at least 110, or at least 120, or at least 130, or at least 140, or at least 150, or at least 160, or at least 170, or at least 180, or at least 185 amino acid residues.

The parent protease may also be an allelic variant, allelic referring to the existence of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In another embodiment, the parent protease may be a genetically engineered protease, e.g. a variant of the wild-type or natural parent proteases referred to above comprising a substitution, deletion, and/or insertion of one or more amino acids. In other words: The parent protease may itself be a protease variant, such as Protease 22. The amino acid sequence of such parent protease may differ from the amino acid sequence specified by an insertion or deletion of one or more amino acid residues and/or the substitution of one or more amino acid residues by different amino acid residues. The amino acid changes may be of a minor, or of a major, nature. Amino acid changes of a major nature are e.g. those resulting in a variant protease of the present invention with amended properties. In another particular embodiment, the amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Still further examples of genetically engineered parent proteases are synthetic proteases, designed by man, and expectedly not occurring in nature. EP 897985 discloses a process of preparing a consensus protein. Shuffled proteases are other examples of synthetic or genetically engineered parent proteases, which can be prepared as is generally known in the art, eg by Site-directed Mutagenesis, by PCR (using a PCR fragment containing the desired mutation as one of the primers in the PCR reactions), or by Random Mutagenesis. Included in the concept of a synthetic protease is also any hybrid or chimeric protease, i.e. a protease which comprises a combination of partial amino acid sequences derived from at least two proteases. Gene shuffling is generally described in e.g. WO 95/22625 and WO 96/00343. Re-combination of protease genes can be made independently of the specific sequence of the parents by synthetic shuffling as described in Ness, J. E. et al, in Nature Biotechnology, Vol. 20 (12), pp. 1251-1255, 2002. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence. Two, three, four, five or all six of the proteases designated Protease 10, 18, 11, 35, 08 and 22 (SEQ ID NOs: 2, 4, 6, 8, 10, and 21; in particular the mature parts thereof) are particular examples of such parent proteases which can be subjected to shuffling as described above, to provide additional proteases of the invention.

In further particular embodiments, the parent protease comprises, or consists of, respectively, the amino acid sequence specified, or an allelic variant thereof; or a fragment thereof that has protease activity.

In still further particular embodiments, the protease variant of the invention is not identical to: (i) amino acids 1-188 of SEQ ID NO: 2, amino acids 1-188 of SEQ ID NO: 4, amino acids 1-188 of SEQ ID NO: 6, amino acids 1-188 of SEQ ID NO: 8, and amino acids 1-188 of SEQ ID NO: 10; (ii) amino acids 1-188 of SEQ ID NO: 2; (iii) amino acids 1-188 of SEQ ID NO: 2 with the substitution T87A; (iv) amino acids 1-188 of SEQ ID NO: 4; (v) amino acids 1-188 of SEQ ID NO: 6; (vi) amino acids 1-188 of SEQ ID NO: 8; (vii) amino acids 1-188 of SEQ ID NO: 10; (viii) the protease derived from Nocardiopsis dassonvillei NRRL 18133; (ix) the protease having amino acids 1 to 188 of SEQ ID NO: 2 as disclosed in JP 2003284571-A; (x) the protease having the sequence entered in GENESEQP with no. ADF43564; (xi) the protease disclosed in DK patent application no. PA 2004 00969 as SEQ ID NO: 2, in particular the mature part thereof; (xii) the protease disclosed in DK patent application no. PA 2004 00969 as SEQ ID NO: 4, in particular the mature part thereof; (xiii) the protease disclosed in DK patent application no. PA 2004 00969 as SEQ ID NO: 6, in particular the mature part thereof; (xiv) the protease disclosed in DK patent application no. 2004 00969 as SEQ ID NO: 8, in particular the mature part thereof; (xv) the protease disclosed in DK patent application no. PA 2004 00969 as SEQ ID NO: 10, in particular the mature part thereof; (xvi) the protease disclosed in DK patent application no. PA 2004 00969 as SEQ ID NO: 12, in particular the mature part thereof; and/or (xvii) any prior art protease of a percentage of identity to SEQ ID NO: 2 of at least 60%.

Microorganism Taxonomy

Questions relating to taxonomy may be solved by consulting a taxonomy data base, such as the NCBI Taxonomy Browser which is available at the following internet site: http://www.ncbi.nlm.nih.gov/Taxonomy/taxonomyhome-.html/, and/or by consulting Taxonomy handbooks. For the present purposes, the taxonomy is preferably according to the chapter: The road map to the Manual by G. M. Garrity & J. G. Holt in Bergey's Manual of Systematic Bacteriology, 2001, second edition, volume 1, David R. Bone, Richard W. Castenholz.

Amino Acid Homology

The present invention refers to proteases, viz. parent proteases, and/or protease variants, having a certain degree of identity to amino acids 1 to 188 of SEQ ID NO: 2, such parent and/or variant proteases being hereinafter designated "homologous proteases".

For purposes of the present invention the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides "Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

In particular embodiments, the homologous protease has an amino acid sequence which has a degree of identity to amino acids 1 to 188 of SEQ ID NO: 2 of at least 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or of at least about 99%.

In alternative embodiments, the homologous protease has an amino acid sequence which has a degree of identity to SEQ ID NO: 2 of at least 50%, 51%, 52%, 53%, 54%, 55%, 56%, 57%, 58%, or at least 59%.

In another particular embodiment, the parent protease, and/or the protease variant, comprises a mature amino acid sequence which differs by no more than seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by no more than two, or only by one amino acid(s) from the specified amino acid sequence, e.g. amino acids 1 to 188 of SEQ ID NO: 2.

In a still further particular embodiment, the parent protease, and/or the protease variant, comprises a mature amino acid sequence which differs by at least seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by at least two, or by one amino acid(s) from the specified amino acid sequence, e.g. amino acids 1 to 188 of SEQ ID NO: 2.

Nucleic Acid Hybridization

In the alternative, homologous parent proteases, as well as variant proteases, may be defined as being encoded by a nucleic acid sequence which hybridizes under very low stringency conditions, preferably low stringency conditions, more preferably medium stringency conditions, more preferably medium-high stringency conditions, even more preferably high stringency conditions, and most preferably very high stringency conditions with nucleotides 900-1466, or 900-1463, of SEQ ID NO: 1, or a subsequence or a complementary strand thereof (J. Sambrook, E. F. Fritsch, and T. Maniatus, 1989, Molecular Cloning, A Laboratory Manual, 2d edition, Cold Spring Harbor, N.Y.). A subsequence may be at least 100 nucleotides, or at least 200, 300, 400, or at least 500 nucleotides. Moreover, the subsequence may encode a polypeptide fragment that has the relevant enzyme activity.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Position Numbering

In the present context, the basis for numbering positions is amino acids 1 to 188 of SEQ ID NO: 2, Protease 10, starting with A1 and ending with T188, see FIG. 1. A parent protease, as well as a variant protease, may comprise extensions as compared to SEQ ID NO: 2, i.e. in the N-terminal, and/or the C-terminal ends thereof. The amino acids of such extensions, if any, are to be numbered as is usual in the art, i.e. for a C-terminal extension: 189, 190, 191 and so forth, and for an N-terminal extension −1, −2, −3 and so forth.

Alterations, Such as Substitutions, Deletions, Insertions

In the present context, the following are examples of various ways in which a protease variant can be designed or derived from a parent amino acid sequence: An amino acid can be substituted with another amino acid; an amino acid can be deleted; an amino acid can be inserted; as well as any combination of any number of such alterations. For the present purposes, the term substitution is intended to include any number of any type of such alterations. This is a reasonable definition, because, for example, a deletion can be regarded as a substitution of an amino acid, AA, in a given position, nn, with nothing, O, Such substitution can be designated: AAnn( ). Likewise, an insertion of only one amino acid, BB, downstream an amino acid, AA, in a given position, nn, can be designated: ( )naBB. And if two amino acids, BB and CC, are inserted downstream of amino acid AA in position nn, this substitution (combination of two substitutions) can be designated: ( )naBB+( )nbCC, the thus created gaps between amino acids nn and nn+1 in the parent sequence being assigned lower case or subscript letters a, b, c etc. to the former position number, here nn. A similar numbering procedure is followed when aligning a new sequence to the multiple alignment of FIG. 1, in case of a gap being created by the alignment between amino acids nn and nn+1: Each position of the gap is assigned a number: nna, nnb etc. A comma (,) between substituents, as e.g. in the substitution T129E,D,Y,Q means "either or", i.e. that T129 is substituted with E, or D, or Y, or Q. A plus-sign (+) between substitutions, e.g. 129D+135P means "and", i.e. that these two single substitutions are combined in one and the same protease variant.

In the present context, the term "a" substitution" means at least one substitution. At least one means one or more, e.g. one, or two, or three, or four, or five, or six, or seven, or eight, or nine, or ten, or twelve, or fourteen, or fifteen, or sixteen, or eighteen, or twenty, or twentytwo or twentyfour, or twentyfive, or twenty eight, or thirty, and so on, to include in principle, any number of substitutions. The variants of the invention, however, still have to be, e.g., at least 60% identical to SEQ ID NO: 2, this percentage being determined by the above-mentioned program. The substitutions can be applied to any position encompassed by any region mentioned in claim 1, and variants comprising combinations of any number and type of such substitutions are also included. The term substitution as used herein also include deletions, as well as extensions, or insertions, that may add to the length of the sequence corresponding to amino acids 1 to 188 of SEQ ID NO: 2.

Furthermore, the term "a substitution" embraces a substitution into any one of the other nineteen natural amino acids, or into other amino acids, such as non-natural amino acids. For example, a substitution of amino acid T in position 22 includes each of the following substitutions: 22A, 22C, 22D, 22E, 22F, 22G, 22H, 22I, 22K, 22L, 22M, 22N, 22P, 22Q, 22R, 22S, 22V, 22W, and 22Y. This is, by the way, equivalent to the designation 22X, wherein X designates any amino acid. These substitutions can also be designated T22A, T22C, T22X, etc. The same applies by analogy to each and every position mentioned herein, to specifically include herein any one of such substitutions.

Identifying Corresponding Position Numbers

For each amino acid residue in each parent, or variant, protease of the invention, and/or for use according to the invention, it is possible to directly and unambiguously assign an amino acid residue in the sequence of amino acids 1 to 188 of SEQ ID NO: 2 to which it corresponds. Corresponding residues are assigned the same number, by reference to the Protease 10 sequence.

As it appears from the numbering of FIG. 1, in conjunction with the numbering of the sequence listing, for each amino acid residue of each of the proteases Protease 10, Protease 18, Protease 11, Protease 35, Protease 08, and Protease 22, the corresponding amino acid residue in SEQ ID NO: 2 has the same number. This number is easily derivable from FIG. 1. At least in case of these six proteases, the number is the same as the number assigned to this amino acid residue in the sequence listing for the mature part of the respective protease.

For a given position in another protease—be it a parent or a variant protease—a corresponding position of SEQ ID NO: 2 can always be found, as follows:

The amino acid sequence of another parent protease, or, in turn, of a variant protease amino acid sequence, is designated SEQ-X. A position corresponding to position N of SEQ ID NO: 2 is found as follows: The parent or variant protease amino acid sequence SEQ-X is aligned with SEQ ID NO: 2 as specified above in the section entitled Amino Acid Homology. From the alignment, the position in sequence SEQ-X corresponding to position N of SEQ ID NO: 2 can be clearly and unambiguously derived, using the principles described below.

SEQ-X is the mature part of the protease in question. In the alternative, it may also include a signal peptide part, and/or a propeptide part, or it may be a fragment of the mature protease which has protease activity, e.g. a fragment of the same length as SEQ ID NO: 2, and/or it may be the fragment which extends from A1 to T188 when aligned with SEQ ID NO: 2 as described herein.

Region and Position

In the present context, the term region means at least one position of a parent protease amino acid sequence, the term position designating an amino acid residue of such amino acid sequence. In one embodiment, region means one or more successive positions of the parent protease amino acid sequence, e.g. one, two, three, four, five, six, seven, eight, etc., up to any number of consecutive positions of the sequence. Accordingly, a region may consist of one position only, or it may consist of any number of consecutive positions, such as, e.g., positions 62 and 63; or positions 111, 112, 113 and 114. For the present purposes, these two regions are designated 62-63, and 111-114, respectively. The boundaries of these regions or ranges are included in the region.

A region encompasses specifically each and every position it embraces. For example, region 111-114 specifically encompasses each of the positions 111, 112, 113, and 114. The same applies by analogy for the other regions mentioned herein.

Thermostability

For the present purposes, the term thermostable as applied in the context of a certain polypeptide, refers to the melting temperature, Tm, of such polypeptide, as determined using Differential Scanning calorimetry (DSC) in 10 mM sodium phosphate, 50 mM sodium chloride, pH 7.0, using a constant scan rate of 1.5° C./min.

The following Tm's were determined under the above conditions: 76.5° C. (Protease 10), 83.0° C. (Protease 18), 78.3° C. (Protease 08), 76.6° C. (Protease 35), 73.7° C. (Protease 11), and 83.5° C. (Protease 22).

For a thermostable polypeptide, the Tm is at least 83.1° C. In particular embodiments, the Tm is at least 84, 85, 86, 87, 88, 89, 90, 91, 92, 93, 94, 95, 96, 97, 98, 99 or at least 100° C.

In the alternative, the term thermostable refers to a melting temperature of at least 73.8, or at least 76.7° C., or at least 78.4° C., preferably at least 74, 75, 76, 77, 78, 79, 80, 81, 82, or at least 83° C., still as determined using DSC at a pH of 7.0.

For the determination of Tm, a sample of the polypeptide with a purity of at least 90% (or 91, 92, 93, 94, 95, 96, 97, or 98%) as determined by SDS-PAGE may be used. Still further, the enzyme sample may have a concentration of between 0.5 and 2.5 mg/ml protein (or between 0.6 and 2.4, or between 0.7 and 2.2, or between 0.8 and 2.0 mg/ml protein), as determined from absorbance at 280 nm and based on an extinction coefficient calculated from the amino acid sequence of the enzyme in question.

The DSC takes place at the desired pH (e.g. pH 5.5, 7.0, 3.0, or 2.5) and with a constant heating rate, e.g. of 1, 1.5, 2, 3, 4, 5, 6, 7, 8, 9 or 10° C./min.

In a particular embodiment, the protease variant of the invention is thermostable, preferably more thermostable than the parent protease. In this context, preferred parent proteases are Protease 18, or Protease 10.

In another particular embodiment, a culture supernatant of the protease variant of the invention, appropriately diluted, exhibits a residual activity after incubation for four hours at 65° C. in a 0.2 M $Na_2HPO_4$ buffer, titrated with 0.1 M citric acid to i) pH 6.0, or ii) pH 4.0, of at least 20%, relative to an un-incubated (frozen) control, the activity being measured using the Protazyme AK assay at pH 8.5 and 37° C., as described in Example 2. In further particular embodiments, the residual activity is at least 25, 30, 35, 40, 45, 50, 55, 60, 65, 70, 75, or at least 77%.

Temperature Activity Profile

In a particular embodiment, the protease variant of the invention exhibits an amended temperature activity profile as compared to, e.g., Protease 10 (or Protease 18, Protease 11, Protease 35, or Protease 08). For example, the protease variant of the invention may exhibit a relative activity at pH 9 and 80° C. of at least 0.40, preferably at least 0.45, 0.50, 0.55, 0.60, 0.65, 0.70, 0.75, 0.80, 0.85, 0.90, or at least 0.95, the term "relative" referring to the maximum activity measured for the protease in question. For Protease 22, the activity is relative to the activity at 80° C. which is set to 1.000 (100%), and for Protease 10, the activity at 70° C. is set to 1.000 (100%), see Example 3. As another example, the protease variant of the invention exhibits a relative activity at pH 9 and 90° C. of at least 0.10, preferably at least 0.15, 0.20, 0.25, 0.30, or of at least 0.35. In a particular embodiment, the protease activity is measured using the Protazyme AK assay of Example 1.

Low-Allergenic Variants

In a specific embodiment, the protease variants of the present invention are (also) low-allergenic variants, designed to invoke a reduced immunological response when exposed to animals, including man. The term immunological response is to be understood as any reaction by the immune system of an animal exposed to the protease variant. One type of immunological response is an allergic response leading to increased levels of IgE in the exposed animal. Low-allergenic variants may be prepared using techniques known in the art. For example the protease variant may be conjugated with polymer moieties shielding portions or epitopes of the protease variant involved in an immunological response. Conjugation with polymers may involve in vitro chemical coupling of polymer to the protease variant, e.g. as described in WO 96/17929, WO 98/30682, WO 98/35026, and/or WO 99/00489. Conjugation may in addition or alternatively thereto involve in vivo coupling of polymers to the protease variant. Such conjugation may be achieved by genetic engineering of the nucleotide sequence encoding the protease variant, inserting consensus sequences encoding additional glycosylation sites in the protease variant and expressing the protease variant in a host capable of glycosylating the protease variant, see e.g. WO 00/26354. Another way of providing low-allergenic variants is genetic engineering of the nucleotide sequence encoding the protease variant so as to cause the protease variants to self-oligomerize, effecting that protease variant monomers may shield the epitopes of other protease variant monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease variant by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a protease variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into the parent protease coding sequence or a subsequence thereof, wherein the mutant nucleic acid sequence encodes a variant protease. The introduction of a mutation into the nucleic acid sequence to exchange one nucleotide for another nucleotide may be accomplished by site-directed mutagenesis using any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the protease enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent protease in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985 (see the section "Parent Protease" for more details).

In particular embodiments, the nucleic acid sequence of the invention is not identical to: (i) Nucleotides 900-1466, or 900-1463, of SEQ ID NO: 1, nucleotides 499-1062 of SEQ ID NO: 3, nucleotides 496-1059 of SEQ ID NO: 5, nucleotides 496-1059 of SEQ ID NO: 7, and nucleotides 502-1065 of SEQ ID NO: 9; (ii) nucleotides 900-1466 of SEQ ID NO: 1; (iii) nucleotides 900-1463 of SEQ ID NO: 1; (iv) nucleotides 900-1463 of SEQ ID NO: 1 as disclosed in DK 1996 00013; (v) nucleotides 499-1062 of SEQ ID NO: 3; (vi) nucleotides 496-1059 of SEQ ID NO: 5; (vii) nucleotides 496-1059 of SEQ ID NO: 7; (viii) nucleotides 502-1065 of SEQ ID NO: 9; (xi) the nucleic acid sequence encoding the mature peptide part of the protease derived from Nocardiopsis dassonvillei NRRL 18133; (x) the nucleic acid sequence having SEQ ID NO: 1 as disclosed in JP 2003284571-A; (xi) the nucleic acid sequence GENESEQN no. ADF43563; (xii) the nucleic acid sequence disclosed in DK patent application no. PA 2004 00969 as SEQ ID NO: 1, in particular the mature peptide encoding part thereof; (xiii) the nucleic acid sequencep disclosed in DK patent application no. PA 2004 00969 as SEQ ID NO: 3, in particular the mature peptide encoding part thereof; (xiv) the nucleic acid sequence disclosed in DK patent application no. PA 2004 00969 as SEQ ID NO: 5, in particular the mature peptide encoding part thereof; (xv) the nucleic acid sequence disclosed in DK patent application no. PA 2004 00969 as SEQ ID NO: 7, in particular the mature peptide encoding part thereof; (xvi) the nucleic acid sequence disclosed in DK patent application no. PA 2004 00969 as SEQ ID NO: 9, in particular the mature peptide encoding part thereof; (xvii) the nucleic acid sequence disclosed in DK patent application no. PA 2004 00969 as SEQ ID NO: 11, in particular the mature peptide encoding part thereof; and/or (xviii) nucleic acid sequences encoding any prior art proteases of at least 60% identity to amino acids 1 to 188 of SEQ ID NO: 2.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

Expression Vector

A nucleic acid sequence encoding a protease variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a protease variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The protease variant may also be co-expressed together with at least one other enzyme of animal feed interest, such as an alpha-amylase, a phytase, a galactanase, a xylanase, an endoglucanase, an endo-1,3(4)-beta-glucanase, an alpha-galactosidase, and/or a protease. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease variant may also be expressed as a fusion protein, i.e. that the gene encoding the protease variant has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote cell, such as an animal, a mammalian, an insect, a plant, or a fungal cell. Preferred animal cells are non-human animal cells.

In a preferred embodiment, the host cell is a fungal cell, or a yeast cell, such as a *Candida, Hansenula, Kluyveromyces, Pichia, Saccharomyces, Schizosaccharomyces*, or *Yarrowia* cell. The fungal host cell may be a filamentous fungal cell, such as a cell of a species of, but not limited to, *Acremonium, Aspergillus, Fusarium, Humicola, Mucor, Myceliophthora, Neurospora, Penicillium, Thielavia, Tolypocladium*, or *Trichoderma*. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus* clausii, *Bacillus coagulans, Bacillus lautus, Bacillus lentus, Bacillus licheniformis, Bacillus megaterium, Bacillus stearothermophilus, Bacillus subtilis*, and *Bacillus thuringiensis*, or a *Streptomyces* cell, such as *Streptomyces lividans* or *Streptomyces murinus*, or a *Nocardiopsis* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

Methods of Production

The present invention also relates to methods for producing a protease variant of the present invention comprising (a) cultivating a host cell under conditions conducive for production of the protease variant; and (b) recovering the protease variant.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the protease is secreted into the nutrient medium, it can be recovered directly from the medium. If it is not secreted, it can be recovered from cell lysates.

The resulting protease may be recovered by methods known in the art. For example, it can be recovered from the nutrient medium by conventional procedures including, but not limited to, centrifugation, filtration, extraction, spray-drying, evaporation, or precipitation.

The proteases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

In a particular embodiment, the polypeptide is targeted to the endosperm storage vacuoles in seeds. This can be obtained by synthesizing it as a precursor with a suitable signal peptide, see Horvath et al. in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*.

Low-phytate plants as described e.g. in U.S. Pat. No. 5,689,054 and U.S. Pat. No. 6,111,168 are examples of engineered plants.

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants. Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the following promoters may be used: The 35S—CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689. Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the *chlorella* virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are generally preferred for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a protease variant of the present invention under conditions conducive for production of the protease variant; and (b) recovering the protease variant.

Animals as Expression Hosts

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a protease variant of the present invention so as to express and produce the protease variant. The protease variant may be recovered from the animal, e.g. from the milk of female animals, or it may be expressed to the benefit of the animal itself, e.g. to assist the animal's digestion. Examples of animals are mentioned below in the section headed Animal Feed and Animal Feed Additives.

To produce a transgenic animal with a view to recovering the protease variant from the milk of the animal, a gene encoding the protease variant may be inserted into the fertilized eggs of an animal in question, e.g. by use of a transgene expression vector which comprises a suitable milk protein promoter, and the gene encoding the protease variant. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The protease variant may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease variant, the transgene may be operably linked to a first regulatory sequence for salivary gland specific expression of the protease variant, as disclosed in WO 2000/064247.

Animal Feed and Animal Feed Additives

For the present purposes, the term animal includes all animals, including human beings. In a particular embodiment, the protease variants and compositions of the invention can be used as a feed additive for non-human animals. Examples of animals are non-ruminants, and ruminants, such as sheep, goats, horses, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal. The feed can be fed to the animal before, after, or simultaneously with the diet. The latter is preferred.

The composition of the invention, when intended for addition to animal feed, may be designated an animal feed additive. Such additive always comprises the protease variant in question, preferably in the form of stabilized liquid or dry compositions. The additive may comprise other components or ingredients of animal feed. The so-called pre-mixes for animal feed are particular examples of such animal feed additives. Pre-mixes may contain the enzyme(s) in question, and in addition at least one vitamin and/or at least one mineral.

Accordingly, in a particular embodiment, in addition to the component polypeptides, the composition of the invention may comprise or contain at least one fat-soluble vitamin, and/or at least one water-soluble vitamin, and/or at least one trace mineral. Also at least one macro mineral may be included.

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, e.g. carotenoids such as beta-carotene, astaxanthin, and lutein; aroma compounds; stabilizers; polyunsaturated fatty acids; reactive oxygen generating species; antimicrobial peptides; and/or at least one additional enzyme.

Additional enzyme components of the invention include at least one polypeptide having amylase, preferably alpha-amylase, activity, and/or at least one polypeptide having xylanase activity; and/or at least one polypeptide having endoglucanase activity; and/or at least one polypeptide having endo-1,3(4)-beta-glucanase activity; and/or at least one polypeptide having phytase activity; and/or at least one polypeptide having galactanase activity; and/or at least one polypeptide having alpha-galactosidase activity; and/or at least one other polypeptide having protease activity (EC 3.4.-.-); and/or at least one polypeptide having phospholipase A1 (EC 3.1.1.32), phospholipase A2 (EC 3.1.1.4), lysophospholipase (EC 3.1.1.5), phospholipase C (EC 3.1.4.3), and/or phospholipase D (EC 3.1.4.4) activity.

Alpha-amylase activity can be measured as is known in the art, e.g. using a starch-based substrate.

Xylanase activity can be measured using any assay, in which a substrate is employed, that includes 1,4-beta-D-xylosidic endo-linkages in xylans. Different types of substrates are available for the determination of xylanase activity e.g. Xylazyme cross-linked arabinoxylan tablets (from MegaZyme), or insoluble powder dispersions and solutions of azo-dyed arabinoxylan.

Endoglucanase activity can be determined using any endoglucanase assay known in the art. For example, various cellulose- or beta-glucan-containing substrates can be applied. An endoglucanase assay may use AZCL-Barley beta-Glucan, or preferably (1) AZCL-HE-Cellulose, or (2) Azo-CM-cellulose as a substrate. In both cases, the degradation of the substrate is followed spectrophotometrically at $OD_{595}$ (see the Megazyme method for AZCL-polysaccharides for the assay of endo-hydrolases at http://www.megazyme.com/booklets/AZCLPOL.pdf.

Endo-1,3(4)-beta-glucanase activity can be determined using any endo-1,3(4)-beta-glucanase assay known in the art. A preferred substrate for endo-1,3(4)-beta-glucanase activity measurements is a cross-linked azo-coloured beta-glucan Barley substrate, wherein the measurements are based on spectrophotometric determination principles.

Phytase activity can be measured using any suitable assay, e.g. the FYT assay described in Example 4 of WO 98/28408.

Galactanase can be assayed e.g. with AZCL galactan from Megazyme, and alpha-galactosidase can be assayed e.g. with pNP-alpha-galactoside.

For assaying these enzyme activitites the assay-pH and the assay-temperature are to be adapted to the enzyme in question (preferably a pH close to the optimum pH, and a temperature close to the optimum temperature). A preferred assay pH is in the range of 2-10, preferably 3-9, more preferably pH 3 or 4 or 5 or 6 or 7 or 8, for example pH 3 or pH 7. A preferred assay temperature is in the range of 20-90° C., preferably 30-90° C., more preferably 40-80° C., even more preferably 40-70° C., preferably 40 or 45 or 50° C. The enzyme activity is defined by reference to appropriate blinds, e.g. a buffer blind.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus* giganteus, and Aspergillus niger peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat and water soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg. WO 01/58275 corresponds to U.S. Ser. No. 09/779,334 which is hereby incorporated by reference.

An animal feed composition according to the invention has a crude protein content of 50-800 g/kg, and furthermore comprises at least one protease variant as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or, in a particular embodiment, it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley;

and/or 0-30% oats; and/or 0-40% soybean meal; and/or 0-25%, preferably O-10%, fish meal; 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease variant should of course be applied in an effective amount, i.e. in an amount adequate for improving solubilisation and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

Detergent Compositions

The protease variant of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease variant of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258068 and EP 305216 or from *H. insolens* as described in WO 96/13580, a *Pseudomonas* lipase, e.g. from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Method for Generating Protease Variants

The invention also relates to a method for generating a protease variant of an improved property, the method comprising the following steps:

(a) selecting a parent protease of at least 60% identity to amino acids 1 to 188 of SEQ ID NO: 2;

(b) establishing a 3D structure of the parent protease by homology modelling using the FIG. 2 structure as a model; and/or aligning the parent protease according to the alignment of FIG. 1;

(c) proposing at least one amino acid substitution, e.g. by:
  (i) subjecting the 3D structure of (b) to MD simulations at increased temperatures, and identifying regions in the amino acid sequence of the parent protease of high mobility (isotropic fluctuations);
  (ii) introducing disulfid bridges by way of cysteine substitutions (C—C);
  (iii) introducing proline substitutions (P);
  (iv) replacing exposed neutral amino acid residues with negatively charged amino acid residues (E,D);
  (v) replacing exposed neutral amino aicd residues with positively charged amino acid residues (R,K);
  (vi) replacing small amino acid residues inside the protein with bulkier amino acid residues (W);
  (vii) comparing by homology alignment and/or homology modelling according to step (c)(i) at least two related parent proteases and transferring amino acid residue differences inbetween these protease backbones, preferably from a backbone having the improved property to a backbone not having this improved property;

(d) preparing a DNA sequence encoding the parent protease but for inclusion of a DNA codon of the at least one amino acid substitution proposed in steps (c)(ii)-(c)(vii), or subjecting the parent DNA sequence to random mutagenesis, targetting at least one of the regions identified in step (c)(i);

(e) expressing the DNA sequence obtained in step (d) in a host cell, and (h) selecting a host cell expressing a protease variant with an improved property.

The invention furthermore relates to a method for producing a protease variant obtainable or obtained by the method of generating protease variants described above, comprising (a) cultivating the host cell to produce a supernatant comprising the variant; and (b) recovering the variant.

The invention also relates to isolated nucleic acid sequences comprising a nucleic acid sequence which encodes the protease variant obtainable according to this method, as well as methods for producing it by (a) cultivating the host cell to produce a supernatant comprising the variant; and (b) recovering the variant; a transgenic plant, or plant part, capable of expressing it; transgenic, non-human animals, or products, or elements thereof, being capable of expressing it;

animal feeds, as well as animal feed additives, comprising it; methods for improving the nutritional value of an animal feed by use thereof; methods for the treatment of proteins, such as vegetable proteins, by use thereof; as well as the use thereof (i) in animal feed; (ii) in the preparation of animal feed; (iii) for improving the nutritional value of animal feed; and/or (iv) for the treatment of proteins; and/or in detergents.

Alternative Embodiments

In an alternative embodiment, the term "alteration" is used instead of "substitution" as the general term for amendments in the protease molecule. This alternative embodiment includes each of the claims formulated as examplified below for claim 1, and also specifically includes everything what is stated herein, e.g. definitions (other than the definition of substitution), i.e. the various aspects, particular embodiments etc.

A variant of a parent protease, comprising an alteration in at least one position of at least one region selected from the group of regions consisting of:
6-18; 22-28; 32-39; 42-58; 62-63; 66-76; 78-100; 103-106; 111-114; 118-131; 134-136; 139-141; 144-151; 155-156; 160-176; 179-181; and 184-188; wherein
(a) the alteration(s) are independently
   (i) an insertion of an amino acid immediately downstream of the position,
   (ii) a deletion of the amino acid which occupies the position, and/or
   (iii) a substitution of the amino acid which occupies the position;
(b) the variant has protease activity; and
(c) each position corresponds to a position of SEQ ID NO: 2, preferably amino acids 1 to 188 thereof; and
(d) the variant has a percentage of identity to SEQ ID NO: 2, preferably to amino acids 1 to 188 thereof, of at least 60%.

The term "polypeptide variant", "protein variant", "enzyme variant", "protease variant" or simply "variant" refers to a polypeptide of the invention comprising one or more alteration(s), such as substitution(s), insertion(s), deletion(s), and/or truncation(s) of one or more specific amino acid residue(s) in one or more specific position(s) in the polypeptide.

The term "parent polypeptide", "parent protein", "parent enzyme", "standard enzyme", "parent protease" or simply "parent" refers to the polypeptide on which the variant was based. This term also refers to the polypeptide with which a variant is compared and aligned.

The term "randomized library", "variant library", or simply "library" refers to a library of variant polypeptides. Diversity in the variant library can be generated via mutagenesis of the genes encoding the variants at the DNA triplet level, such that individual codons are variegated e.g. by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes A/S). They also include the use of DNA shuffling techniques to create a library of full length genes, wherein several gene segments are combined, and wherein each segment may be diversified e.g. by spiked mutagenesis (Stemmer, Nature 370, pp. 389-391, 1994 and U.S. Pat. Nos. 5,811,238; 5,605,793; and U.S. Pat. No. 5,830,721). One can use a gene encoding a protein "backbone" (wildtype parent polypeptide) as a template polynucleotide, and combine this with one or more single or double-stranded oligonucleotides as described in WO 98/41623 and in WO 98/41622 (Novozymes A/S). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone protein in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library, that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g. decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 212) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

In describing the various variants produced or contemplated according to the invention, a number of nomenclatures and conventions are used which are described in detail below. A frame of reference is first defined by aligning the variant polypeptide with a parent enzyme. A preferred parent enzyme is Protease 10 (amino acids 1 to 188 of SEQ ID NO: 2). Thereby a number of alterations will be defined in relation to the amino acid sequence of amino acids 1 to 188 of SEQ ID NO: 2.

A substitution in a variant is indicated as:
Original amino acid—position—substituted amino acid;

The three or one letter codes are used, including the codes Xaa and X to indicate any amino acid residue. Accordingly, the notation "T82S" or "Thr82Ser" means, that the variant comprises a substitution of threonine with serine in the variant amino acid position corresponding to the amino acid in position 82 in the parent enzyme, when the two are aligned as indicated above.

Where the original amino acid residue may be any amino acid residue, a short hand notation may at times be used indicating only the position, and the substituted amino acid, for example:
Position—substituted amino acid; or "82S", Such a notation is particular relevant in connection with modification(s) in a series of homologous polypeptides.

Similarly when the identity of the substituting amino acid residue(s) is immaterial:

Original amino acid—position; or "T82"

When both the original amino acid(s) and substituted amino acid(s) may be any amino acid, then only the position is indicated, e.g.: "82".

When the original amino acid(s) and/or substituted amino acid(s) may comprise more than one, but not all amino acid(s), then the amino acids are listed separated by commas:

Original amino acids—position no.—substituted amino acids; or "T10E,D,Y".

A number of examples of this nomenclature are listed below:

The substitution of threonine for histidine in position 91 is designated as: "His91Thr" or "H91T"; or the substitution of any amino acid residue acid for histidine in position 91 is designated as: "His91Xaa" or "H91X" or "His91" or "H91".

For a modification where the original amino acid(s) and/or substituted amino acid(s) may comprise more than one, but not all amino acid(s), the substitution of glutamic acid, aspartic acid, or tyrosine for threonine in position 10:

"Thr10Glu,Asp,Tyr" or "T10E,D,Y"; which indicates the specific variants: "T10E", "T10D", and "T10Y".

A deletion of glycine in position 26 will be indicated by: "Gly26*" or "G26*"

Correspondingly, the deletion of more than one amino acid residue, such as the deletion of glycine and glutamine in positions 26 and 27 will be designated "Gly26*+Gln27*" or "G26*+Q27*"

The insertion of an additional amino acid residue such as e.g. a lysine after G26 is indicated by: "Gly26GlyLys" or "G26GK"; or, when more than one amino acid residue is inserted, such as e.g. a Lys, and Ala after G26 this will be indicated as: "Gly26GlyLysAla" or "G26GKA".

In such cases the inserted amino acid residue(s) are numbered by the addition of lower case letters to the position number of the amino acid residue preceding the inserted amino acid residue(s). In the above example the sequences would thus be:

| Parent: | | Variant: | |
|---|---|---|---|
| 26 | 26 | 26a | 26b |
| G | G | K | A |

In cases where an amino acid residue identical to the existing amino acid residue is inserted, it is clear that degeneracy in the nomenclature arises. If for example a glycine is inserted after the glycine in the above example this would be indicated by "G26GG".

Given that an alanine were present in position 25, the same actual change could just as well be indicated as "A25AG":

| | Parent: | | Variant: | | |
|---|---|---|---|---|---|
| Numbering I: | 25 | 26 | 25 | 26 | 26a |
| Sequence: | A | G | A | G | G |
| Numbering II: | | | 25 | 25a | 26 |

Such instances will be apparent to the skilled person, and the indication "G26GG" and corresponding indications for this type of insertions is thus meant to comprise such equivalent degenerate indications.

By analogy, if amino acid sequence segments are repeated in the parent polypeptide and/or in the variant, it will be apparent to the skilled person that equivalent degenerate indications are comprised, also when other alterations than insertions are listed such as deletions and/or substitutions. For instance, the deletion of two consecutive amino acids "AG" in the sequence "AGAG" from position 194-197, may be written as "A194*+G1956*" or "A196*+G197*":

| | Parent: | | | | Variant: | |
|---|---|---|---|---|---|---|
| Numbering I: | 194 | 195 | 196 | 197 | 194 | 195 |
| Sequence: | A | G | A | G | A | G |
| Numbering II: | | | | | 196 | 197 |

Variants comprising multiple modifications are separated by pluses, e.g.: "Arg170Tyr+Gly195Glu" or "R170Y+G195E", representing modifications in positions 170 and 195 substituting tyrosine and glutamic acid for arginine and glycine, respectively. Thus, "Tyr167Gly,Ala,Ser,Thr+Arg170Gly,Ala,Ser,Thr" designates the following variants: "Tyr167Gly+Arg170Gly", "Tyr167Gly+Arg170Ala", "Tyr167Gly+Arg170Ser", "Tyr167Gly+Arg170Thr", "Tyr167Ala+Arg170Gly", "Tyr167Ala+Arg170Ala", "Tyr167Ala+Arg170Ser", "Tyr167Ala+Arg 170Thr", "Tyr167Ser+Arg170Gly", "Tyr167Ser+Arg170Ala", "Tyr167Ser+Arg170Ser", "Tyr167Ser+Arg170Thr", "Tyr167Thr+Arg170Gly", "Tyr167Thr+Arg170Ala", "Tyr167Thr+Arg170Ser", and "Tyr167Thr+Arg170Thr".

This nomenclature is particular relevant relating to modifications aimed at substituting, inserting or deleting amino acid residues having specific common properties, such modifications are referred to as conservative amino acid modification(s).

Various Embodiments

These are additional various embodiments of the invention:

The variant of any one of claims 1-16 and 18-20 which comprises at least one of the following substitutions: T10Y, A24S, V51T, E53Q, T82S, A86Q, T87S, 196A, G118N, S122R, N130S, L186I.

The variant of any one of claims 1-16 and 18-19 which comprises at least one of the following substitutions: R38T; Q42G,P; R49T,Q; Q54N,R; A89S,T; H91S,T; N92S; S99A, Q; A120T; E125Q; T129Y,Q; M131L; T135N; Y147F; N151S; R165S; T166V,F; F171Y; V179I, L; preferably at least one of the following substitutions: R38T; N92S; A120T; E125Q; M131L; T135N; Y147F; N151S; R165S; and/or F171Y.

The variant of any one of claims 1-19 which comprises at least one of the following substitutions: A25S, T44S, A62S, P95A, V100I, I114V, T176N,N180S, V184L, R185T.

The variant of any one of claims 1-20 which has amended properties, such as an improved thermostability and/or a higher or lower optimum temperature, such as a Tm of at least 83.1° C. as measured by DSC in 10 mM sodium phosphate, 50 mM sodium chloride, pH 7.0.

The variant of any one of claims 1-20 which derives from a strain of the genus *Nocardiopsis*, such as *Nocardiopsis alba, Nocardiopsis antarctica, Nocardiopsis prasina, Nocardiopsis composta, Nocardiopsis dassonvillei, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis sp., Nocardiopsis synnemataformans, Nocardiopsis trehalosi, Nocardiopsis tropica, Nocardiopsis umidischolae,* or *Nocardiopsis xinjiangensis*, preferably *Nocardiopsis alba* DSM 15647, *Nocardiopsis dassonvillei* NRRL 18133,

*Nocardiopsis dassonvillei* subsp. *dassonvillei* DSM 43235, *Nocardiopsis prasina* DSM 15648, *Nocardiopsis prasina* DSM 15649, *Nocardiopsis* sp. NRRL 18262, most preferably *Nocardiopsis* sp. FERM P-18676.

A composition, such as an animal feed additive, comprising at least one protease variant of any one of claims 1-20, and
(a) at least one fat soluble vitamin;
(b) at least one water soluble vitamin; and/or
(c) at least one trace mineral,
optionally further comprising at least one enzyme selected from the following group of enzymes: amylases, galactanases, alpha-galactosidases, xylanases, endoglucanases, endo-1,3(4)-beta-glucanases, phytases, phospholipases, and other proteases; if desired also comprising at least one amylase, and/or phospholipase.

The present invention is further described by the following examples which should not be construed as limiting the scope of the invention.

EXAMPLES

Example 1

Protease Assays pNA assay
  pNA substrate: Suc-AAPF-pNA (Bachem L-1400).
  Temperature: Room temperature (25° C.)
  Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.

20 microliters protease (diluted in 0.01% Triton X-100) is mixed with 100 microliters assay buffer. The assay is started by adding 100 microliters pNA substrate (50 mg dissolved in 1.0 ml DMSO and further diluted 45× with 0.01% Triton X-100). The increase in $OD_{405}$ is monitored as a measure of the protease activity.

Protazyme AK Assay
  Substrate: Protazyme AK tablet (cross-linked and dyed casein; from Megazyme)
  Temperature: controlled (assay temperature).
  Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 microliters of this suspension and 500 microliters assay buffer are mixed in an Eppendorf tube and placed on ice. 20 microliters protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 microliters supernatant is transferred to a microtiter plate. $OD_{650}$ is read as a measure of protease activity. A buffer blind is included in the assay (instead of enzyme).

Example 2

Preparation and Testing of Protease Variants

Four protease variants comprising the amino acid sequence of amino acids 1 to 188 of SEQ ID NO: 2 (Protease 10) with the single substitutions N47D, T127R, N92K, and Q54R, respectively, were prepared as described below for variant N47D.

Site directed mutagenesis was carried out using the Megaprimer method as described by Sarkar and Sommer, 1990 (BioTechniques 8: 404-407).

The N47D variant was constructed by use of the following primers, of which primer R10WT-CL29 (SEQ ID NO: 11) is gene specific, and primer RSWT126 (SEQ ID NO: 12) mutagenic:

R10WT-CL29: 5' CCGATTATGGAGCGGATTGAA-CATGCG 3' (SEQ ID NO: 11)

RSWT126: 5' GTGACCATCGGCGACG-GCAGGGGCGTCTTCG 3' (SEQ ID NO: 12), to amplify by PCR an approximately 469 bp DNA fragment from the construct described below.

The Protease 10 DNA construct used for the above amplification was an expression cassette (SEQ ID NO: 13) for incorporation into the genome of *Bacillus subtilis*. The construct contains a fusion of DNA encoding the signal sequence and the gene encoding the pro- and the mature protein of Protease 10 (SEQ ID NO: 14), a promoter construction, and also the cat gene conferring resistance towards chloramphenicol. To facilitate the integration into the genome by homologous recombination, flanking regions of around 3 kb of a *Bacillus subtilis* endogenous genes were incorporated upstream and downstream of the Protease 10 encoding sequence.

The resulting 469 bp fragment was purified from an agarose gel (Sigma Aldrich cat. no. A6877) and used as a Megaprimer together with primer R10WT-CL39N (SEQ ID NO: 15) in a second PCR carried out on the same template.

```
R10WT-CL39N:
                                        (SEQ ID NO: 15)
5'GGAGCTCTGAAAAAAAGGAGAGGATAAAGAATGAA 3'.
```

The full construction of approximately 10 kb is made in vitro by long range PCR, using the oligonucleotides R10WT-CL28N (SEQ ID NO: 16), R10WT-CL28C (SEQ ID NO: 17), and the Expand Long Template PCR System from Roche Applied Science (cat no. 11759060), according to the suppliers manual.

```
R10WT-CL28N:
                                        (SEQ ID NO: 16)
5'GCGTTCCGATAATCGCGGTGACAATGCCG 3'

R10WT-CL28C:
                                        (SEQ ID NO: 17)
5'TTCATGAGTCTGCGCCCTGAGATCCTCTG 3'
```

The resulting approximately 1.2 kb fragment was purified and combined in a new PCR reaction using Expand Long Template PCR System with the flanking fragments of the construction made by two PCR reactions using R10WT-2C-rev (SEQ ID NO: 18) and R10WT-CL28C (SEQ ID NO: 17); and RSWT001 (SEQ ID NO: 19) and R10WT-CL28N (SEQ ID NO: 16) as primer sets. The resulting 10 kb fragment can be amplified using the R10WT-CL28N (SEQ ID NO: 16) and R10WT-CL28C (SEQ ID NO: 17) primers, to increase the number of transformants.

R10WT-2C-rev:
(SEQ ID NO: 18)
5'TAATCGCATGTTCAATCCGCTCCATAATCG 3'

RSWT001:
(SEQ ID NO: 19)
5'CCCAACGGTTTCTTCATTCTTTATCCTCTCCTTTTTTTCAGAGC 3'

Competent cells of an amylase- and protease-low strain of Bacillus subtilis (such as strain SHA273 described in WO92/11357 and WO95/10603) were transformed with the respective resulting PCR fragments, and chlorampenicol resistant transformants were selected and checked by DNA sequencing to verify the presence of the correct mutation on the genome.

Cells of Bacillus subtilis harbouring constructs encoding Protease 10 and each of the four variants thereof were used to incubate shakeflasks containing a rich media (PS-1: 100 g/L Sucrose (Danisco cat. no. 109-0429), 40 g/L crust soy, 10 g/L Na$_2$HPO$_4$.12H$_2$O (Merck cat. no. 6579), 0.1 ml/L Pluronic PE 6100 (BASF 102-3098)), and cultivation took place for five days at 30° C. under vigorous shaking.

After cultivation, the supernatants were diluted four times in a 0.2 M Na$_2$HPO$_4$ buffer, titrated with a 0.1 M citric acid to either pH 4.0 or pH 6.0, and split in two. One half was incubated for four hours at 65° C. at the respective pH, after which it was frozen. The other half was frozen immediately and served as the control.

Prior to measuring the residual protease activity, the samples were diluted ten times in 50 mM CHES-HEPES buffer, pH 8.5. The activity was determined using a modified version of the Protazyme AK assay of Example 1, solubilising one tablet of the substrate in 4 ml CHES-HEPES buffer, pH 8.5, mixing under continuous agitation one ml of this substrate solution with 20 ul of diluted protease sample, which was then incubated at 37° C. The substrate should have the correct temperature prior to adding protease. After 15 minutes the reaction was stopped by adding 100 ul 1 M NaOH and the insoluble substrate was precipitated by centrifugation at 15000 rpm for 3 minutes after which the absorbance at 650 nm was measured. The values should be below OD 3.0, alternatively the protease sample should be diluted more than ten times prior to the activity measurement.

The relative residual activity (%) is calculated by dividing the activity after incubation at 65° C. with the activity of the corresponding control. The results of Table 1 below show that all four variants are of an improved thermostability as compared to Protease 10.

TABLE 1

Residual activity after incubation for four hours at 65° C.

| Protease | % Residual Actitivty pH 6 | % Residual Activity pH 4 |
|---|---|---|
| Protease 10 + N47D | 44 | 68 |
| Protease 10 + T127R | — | 77 |
| Protease 10 + N92K | — | 55 |
| Protease 10 + Q54R | 52 | 67 |
| Protease 10 | 19 | 41 |

Example 3

Protease Variant 22

A protease variant designated "Protease 22" and comprising a number of substitutions in thirteen of the seventeen regions specified in claim 1 was designed. This variant comprises the following substitutions as compared to the mature part of Protease 10 (amino acids 1-188 of SEQ ID NO: 2): T10Y, A25S, R38T, Q42P, T44S, R49K, Q54R, V56I, A62S, T82S, S99A, G118Ns, S120T, S122R, E125Q, T129Y, N130S, M131L, R165S, T166A, F171Y, T176N, V179L, N180S, V184L, and R185T.

The mature part of Protease 22 is amino acids 1-196 of SEQ ID NO: 21. The DNA sequence corresponding to SEQ ID NO: 21 is SEQ ID NO: 20.

The DNA sequence of SEQ ID NO: 20 was constructed and introduced into a Bacillus host for expression. The expressed protease was purified and characterized as an alpha-lytic protease (peptidase family 51 E and/or S2A).

The temperature-activity relationship of Protease 22 was measured at pH 9, using the Protazyme AK assay of Example 1, Protease 10 being included for comparative purposes. The results are shown in Table 2 below.

TABLE 2

Temperature profile at pH9 of Protease 22 and Protease 10

| | Relative activity at pH 9 | |
|---|---|---|
| Temperature (° C.) | Protease 22 | Protease 10 |
| 15 | 0.016 | 0.015 |
| 25 | 0.010 | 0.024 |
| 37 | 0.028 | 0.068 |
| 50 | 0.069 | 0.199 |
| 60 | 0.138 | 0.510 |
| 70 | 0.474 | 1.000 |
| 80 | 1.000 | 0.394 |
| 90 | 0.375 | — |

From these results it appears that Protease 22 has a higher temperature optimum at pH 9 than the Protease 10, viz. around 80° C. as compared to around 70° C.

Differential Scanning calorimetry (DSC) was used to determine temperature stability at pH 7.0 of Protease 22 and Protease 10. The purified proteases were dialysed over night at 4° C. against 10 mM sodium phosphate, 50 mM sodium chloride, pH 7.0 and run on a VP-DSC instrument (Micro Cal) with a constant scan rate of 1.5° C./min from 20 to 100° C. Data-handling was performed using the MicroCal Origin software.

The resulting denaturation or melting temperatures, Tm's, were: For Protease 22: 83.5° C.; for Protease 10: 76.5° C.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A variant of a parent protease, comprising a substitution in at least one position selected from the group consisting of positions 42, 43, 45, 46, 47, 48, 50, 51, 52, 53, 54, 55, 57, and 58, wherein
   (a) the variant has a sequence identity to the sequence of amino acids 1 to 188 of SEQ ID NO: 2 of at least 90% but less than 100%;
   (b) the variant has protease activity; and
   (c) each position corresponds to a position of amino acids 1 to 188 of SEQ ID NO: 2.

2. The variant of claim 1, which has a sequence identity to the sequence of amino acids 1 to 188 of SEQ ID NO: 2 of at least 92%.

3. The variant of claim 1, which has a sequence identity to the sequence of amino acids 1 to 188 of SEQ ID NO: 2 of at least 94%.

4. The variant of claim 1, which has a sequence identity to the sequence of amino acids 1 to 188 of SEQ ID NO: 2 of at least 95%.

5. The variant of claim 1, which has a sequence identity to the sequence of amino acids 1 to 188 of SEQ ID NO: 2 of at least 96%.

6. The variant of claim 1, which has a sequence identity to the sequence of amino acids 1 to 188 of SEQ ID NO: 2 of at least 97%.

7. The variant of claim 1, which has a sequence identity to the sequence of amino acids 1 to 188 of SEQ ID NO: 2 of at least 98%.

8. The variant of claim 1, which comprises a substitution at position 42.

9. The variant of claim 8, which comprises 42E,D,G,P.

10. The variant of claim 9, which comprises 42G,P.

11. The variant of claim 1, which comprises a substitution at position 43.

12. The variant of claim 11, which comprises 43A,C,D,E,F,G,H,I,K,L,M,N,P,Q,R,S,T,W,Y.

13. The variant of claim 1, which comprises a substitution at position 45.

14. The variant of claim 12, which comprises 45A,C,D,E,F,G,H,K,L,M,N,P,Q,R,S,T,V,W,Y.

15. The variant of claim 1, which comprises a substitution at position 46.

16. The variant of claim 15, which comprises 46A,C,D,E,F,H,I,K,L,M,N,P,Q,R,S,T,V,W,Y.

17. The variant of claim 16, which comprises 46E,D.

18. The variant of claim 1, which comprises a substitution at position 47.

19. The variant of claim 18, which comprises 47A,C,D,E,F,G,H,I,K,L,M,P,Q,R,S,T,V,W,Y.

20. The variant of claim 19, which comprises 47E,D.

21. The variant of claim 1, which comprises a substitution at position 48.

22. The variant of claim 21, which comprises 48A,C,D,E,F,H,I,K,L,M,N,P,Q,R,S,T,V,W,Y.

23. The variant of claim 1, which comprises a substitution at position 50.

24. The variant of claim 23, which comprises 50A,C,D,E,F,H,I,K,L,M,N,P,Q,R,S,T,V,W,Y.

25. The variant of claim 1, which comprises a substitution at position 51.

26. The variant of claim 25, which comprises 51T.

27. The variant of claim 1, which comprises a substitution at position 52.

28. The variant of claim 27, which comprises 52C.

29. The variant of claim 1, which comprises a substitution at position 53.

30. The variant of claim 1, which comprises a substitution at position 54.

31. The variant of claim 30, which comprises 54N,R,Q.

32. The variant of claim 1, which comprises a substitution at position 55.

33. The variant of claim 32, which comprises 55C,Q.

34. The variant of claim 33, which comprises 55C+63C.

35. The variant of claim 1, which comprises a substitution at position 57.

36. The variant of claim 1, which comprises a substitution at position 58.

37. The variant of claim 36, which comprises 58E,D.

38. A detergent composition comprising a variant of claim 1 and a surfactant.

39. An animal feed additive comprising at least one variant of claim 1, and
   (a) at least one fat soluble vitamin;
   (b) at least one water soluble vitamin; and/or
   (c) at least one trace mineral.

40. An animal feed composition having a crude protein content of 50 to 800 g/kg and comprising a variant of claim 1.

41. A method for improving the nutritional value of an animal feed, comprising at least one protein, comprising adding a variant of claim 1 to the animal feed in an amount adequate for improving the nutritional value of the animal feed.

42. A method for the proteolytic treatment of proteins, comprising
   (a) adding a variant of claim 1 to a composition comprising proteins; and
   (b) incubating the composition and variant for a time sufficient for treating proteins in the composition.

43. A variant of a parent protease, comprising a substitution selected from the group consisting of:
   44A,C,D,E,F,G,H,I,K,L,M,N,P,Q,R,V,W,Y;
   49A,C,D,E,F,G,H,I,K,L,M,N,P,S,T,V,W,Y; and
   56R,K;
   wherein
   (a) the variant has a sequence identity to the sequence of amino acids 1 to 188 of SEQ ID NO: 2 of at least 90% but less than 100%;
   (b) the variant has protease activity; and
   (c) each position corresponds to a position of amino acids 1 to 188 of SEQ ID NO: 2.

44. The variant of claim 43, which has a sequence identity to the sequence of amino acids 1 to 188 of SEQ ID NO: 2 of at least 95%.

45. A detergent composition comprising a variant of claim 43 and a surfactant.

46. An animal feed additive comprising at least one variant of claim 43, and
(a) at least one fat soluble vitamin;
(b) at least one water soluble vitamin; and/or
(c) at least one trace mineral.

47. An animal feed composition having a crude protein content of 50 to 800 g/kg and comprising a variant of claim 43.

48. A method for improving the nutritional value of an animal feed, comprising at least one protein, comprising adding a variant of claim 43 to the animal feed in an amount adequate for improving the nutritional value of the animal feed.

49. A method for the treatment of proteins, comprising
(a) adding a variant of claim 43 to a composition comprising proteins; and
(b) incubating the composition and variant for a time sufficient for treating proteins in the composition.

* * * * *

SEQUENCE LISTING

<160> NUMBER OF SEQ ID NOS: 21

<210> SEQ ID NO 1
<211> LENGTH: 1596
<212> TYPE: DNA
<213> ORGANISM: Nocardiopsis sp. NRRL 18262 ("Protease 10")
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 1

```
acgtttggta cgggtaccgg tgtccgcatg tggccagaat gcccccttgc gacagggaac      60
ggattcggtc ggtagcgcat cgactccgac aaccgcgagg tggccgttcg cgtcgccacg     120
ttctgcgacc gtcatgcgac ccatcatcgg gtgaccccac cgagctctga atggtccacc     180
gttctgacgg tctttcccte accaaaaacgt gcacctatgg ttaggacgtt gtttaccgaa    240
tgtctcggtg aacgacaggg gccggacggt attcggcccc gatccccgt tgatccccc      300 aggagagtag ggacccc atg cga ccc tcc ccc gtt gtc tcc gcc atc  ggt      350
                   Met Arg Pro Ser Pro Val Val Ser Ala Ile Gly
                              -190                -185 acg gga gcg ctg gcc ttc ggt ctg gcg ctg tcc ggt acc ccg ggt           395
Thr Gly Ala Leu Ala Phe Gly Leu Ala Leu Ser Gly Thr Pro Gly
           -180             -175              -170 gcc ctc gcg gcc acc gga gcg ctc ccc cag tca ccc acc ccg gag           440
Ala Leu Ala Ala Thr Gly Ala Leu Pro Gln Ser Pro Thr Pro Glu
       -165             -160             -155 gcc gac gcg gtc tcc atg cag gag gcg ctc cag cgc gac ctc gac           485
Ala Asp Ala Val Ser Met Gln Glu Ala Leu Gln Arg Asp Leu Asp
       -150             -145             -140 ctg acc tcc gcc gag gcc gag gag ctg ctg gcc gcc cag gac acc           530
Leu Thr Ser Ala Glu Ala Glu Glu Leu Leu Ala Ala Gln Asp Thr
       -135             -130             -125 gcc ttc gag gtc gac gag gcc gcg gcc gag gcc gcc ggg gac gcc           575
Ala Phe Glu Val Asp Glu Ala Ala Ala Glu Ala Ala Gly Asp Ala
       -120             -115             -110 tac ggc ggc tcc gtc ttc gac acc gag agc ctg gaa ctg acc gtc ctg       623
Tyr Gly Gly Ser Val Phe Asp Thr Glu Ser Leu Glu Leu Thr Val Leu
       -105              -100             -95 gtc acc gat gcc gcc gcg gtc gag gcc gtg gag gcc acc ggc gcc ggg       671
Val Thr Asp Ala Ala Ala Val Glu Ala Val Glu Ala Thr Gly Ala Gly
       -90              -85              -80 acc gag ctg gtc tcc tac ggc atc gac ggt ctc gac gag atc gtc cag       719
Thr Glu Leu Val Ser Tyr Gly Ile Asp Gly Leu Asp Glu Ile Val Gln
       -75              -70              -65 gag ctc aac gcc gcc gac gcc gtt ccc ggt gtg gtc ggc tgg tac ccg       767
Glu Leu Asn Ala Ala Asp Ala Val Pro Gly Val Val Gly Trp Tyr Pro
-60              -55              -50              -45 gac gtg gcg ggt gac acc gtc gtc ctg gag gtc ctg gag ggt tcc gga      815
Asp Val Ala Gly Asp Thr Val Val Leu Glu Val Leu Glu Gly Ser Gly
           -40              -35              -30 gcc gac gtc agc ggc ctg ctc gcg gac gcc ggc gtg gac gcc tcg gcc      863
Ala Asp Val Ser Gly Leu Leu Ala Asp Ala Gly Val Asp Ala Ser Ala
       -25              -20              -15 gtc gag gtg acc acg agc gac cag ccc gag ctc tac gcc gac atc atc      911
```

```
Val Glu Val Thr Thr Ser Asp Gln Pro Glu Leu Tyr Ala Asp Ile Ile
    -10              -5                -1   1 ggt ggt ctg gcc tac acc atg ggc ggc cgt tgt tcg gtc ggc ttc gcg      959
Gly Gly Leu Ala Tyr Thr Met Gly Gly Arg Cys Ser Val Gly Phe Ala
5               10              15              20 gcc acc aac gcc gcc ggt cag ccc ggg ttc gtc acc gcc ggt cac tgc     1007
Ala Thr Asn Ala Ala Gly Gln Pro Gly Phe Val Thr Ala Gly His Cys
        25              30              35 ggc cgc gtg ggc acc cag gtg acc atc ggc aac ggc agg ggc gtc ttc     1055
Gly Arg Val Gly Thr Gln Val Thr Ile Gly Asn Gly Arg Gly Val Phe
            40              45              50 gag cag tcc gtc ttc ccc ggc aac gac gcg gcc ttc gtc cgc ggt acg     1103
Glu Gln Ser Val Phe Pro Gly Asn Asp Ala Ala Phe Val Arg Gly Thr
        55              60              65 tcc aac ttc acg ctg acc aac ctg gtc agc cgc tac aac acc ggc ggg     1151
Ser Asn Phe Thr Leu Thr Asn Leu Val Ser Arg Tyr Asn Thr Gly Gly
    70              75              80 tac gcc acg gtc gcc ggt cac aac cag gcc ccc atc ggc tcc tcc gtc     1199
Tyr Ala Thr Val Ala Gly His Asn Gln Ala Pro Ile Gly Ser Ser Val
85              90              95              100 tgc cgc tcc ggc tcc acc acc ggt tgg cac tgc ggc acc atc cag gcc     1247
Cys Arg Ser Gly Ser Thr Thr Gly Trp His Cys Gly Thr Ile Gln Ala
            105             110             115 cgc ggc cag tcg gtg agc tac ccc gag ggc acc gtc acc aac atg acc     1295
Arg Gly Gln Ser Val Ser Tyr Pro Glu Gly Thr Val Thr Asn Met Thr
        120             125             130 cgg acc acc gtg tgc gcc gag ccc ggc gac tcc ggc ggc tcc tac atc     1343
Arg Thr Thr Val Cys Ala Glu Pro Gly Asp Ser Gly Gly Ser Tyr Ile
    135             140             145 tcc ggc acc cag gcc cag ggc gtg acc tcc ggc ggc tcc ggc aac tgc     1391
Ser Gly Thr Gln Ala Gln Gly Val Thr Ser Gly Gly Ser Gly Asn Cys
150             155             160 cgc acc ggc ggg acc acc ttc tac cag gag gtc acc ccc atg gtg aac     1439
Arg Thr Gly Gly Thr Thr Phe Tyr Gln Glu Val Thr Pro Met Val Asn
165             170             175             180 tcc tgg ggc gtc cgt ctc cgg acc tgatccccgc ggttccaggc ggaccgacgg    1493
Ser Trp Gly Val Arg Leu Arg Thr
                185 tcgtgacctg agtaccaggc gtccccgccg cttccagcgg cgtccgcacc ggggtgggac   1553 cgggcgtggc cacggcccca cccgtgaccg gaccgcccgg cta                     1596

<210> SEQ ID NO 2
<211> LENGTH: 382
<212> TYPE: PRT
<213> ORGANISM: Nocardiopsis sp. NRRL 18262 ("Protease 10")

<400> SEQUENCE: 2

Met Arg Pro Ser Pro  Val Val Ser Ala Ile  Gly Thr Gly Ala Leu
                -190               -185               -180

Ala Phe Gly Leu Ala  Leu Ser Gly Thr Pro  Gly Ala Leu Ala Ala
                -175               -170               -165

Thr Gly Ala Leu Pro  Gln Ser Pro Thr Pro  Glu Ala Asp Ala Val
                -160               -155               -150

Ser Met Gln Glu Ala  Leu Gln Arg Asp Leu  Asp Leu Thr Ser Ala
                -145               -140               -135

Glu Ala Glu Glu Leu  Leu Ala Ala Gln Asp  Thr Ala Phe Glu Val
                -130               -125               -120

Asp Glu Ala Ala Ala  Glu Ala Ala Gly Asp  Ala Tyr Gly Gly Ser
                -115               -110               -105
```

Val Phe Asp Thr Glu  Ser Leu Glu Leu Thr Val Leu Val Thr Asp Ala
                -100              -95                 -90

Ala Ala Val Glu Ala Val Glu Ala Thr Gly Ala Gly Thr Glu Leu Val
            -85              -80                 -75

Ser Tyr Gly Ile Asp Gly Leu Asp Glu Ile Val Gln Glu Leu Asn Ala
        -70              -65                 -60

Ala Asp Ala Val Pro Gly Val Gly Trp Tyr Pro Asp Val Ala Gly
    -55              -50                 -45

Asp Thr Val Val Leu Glu Val Leu Glu Gly Ser Gly Ala Asp Val Ser
-40              -35                 -30                 -25

Gly Leu Leu Ala Asp Ala Gly Val Asp Ala Ser Ala Val Glu Val Thr
            -20              -15                 -10

Thr Ser Asp Gln Pro Glu Leu Tyr Ala Asp Ile Ile Gly Gly Leu Ala
        -5               -1  1                 5

Tyr Thr Met Gly Gly Arg Cys Ser Val Gly Phe Ala Ala Thr Asn Ala
        10              15                  20

Ala Gly Gln Pro Gly Phe Val Thr Ala Gly His Cys Gly Arg Val Gly
25              30                  35                  40

Thr Gln Val Thr Ile Gly Asn Gly Arg Gly Val Phe Glu Gln Ser Val
            45                  50                  55

Phe Pro Gly Asn Asp Ala Ala Phe Val Arg Gly Thr Ser Asn Phe Thr
            60                  65                  70

Leu Thr Asn Leu Val Ser Arg Tyr Asn Thr Gly Gly Tyr Ala Thr Val
            75                  80                  85

Ala Gly His Asn Gln Ala Pro Ile Gly Ser Ser Val Cys Arg Ser Gly
            90                  95                  100

Ser Thr Thr Gly Trp His Cys Gly Thr Ile Gln Ala Arg Gly Gln Ser
105                 110                 115                 120

Val Ser Tyr Pro Glu Gly Thr Val Thr Asn Met Thr Arg Thr Thr Val
            125                 130                 135

Cys Ala Glu Pro Gly Asp Ser Gly Gly Ser Tyr Ile Ser Gly Thr Gln
            140                 145                 150

Ala Gln Gly Val Thr Ser Gly Gly Ser Gly Asn Cys Arg Thr Gly Gly
        155                 160                 165

Thr Thr Phe Tyr Gln Glu Val Thr Pro Met Val Asn Ser Trp Gly Val
        170                 175                 180

Arg Leu Arg Thr
185

<210> SEQ ID NO 3
<211> LENGTH: 1065
<212> TYPE: DNA
<213> ORGANISM: Nocardiopsis dassonvillei subspecies dassonvillei DSM
      43235 ("Protease 18")
<220> FEATURE:
<221> NAME/KEY: CDS
<222> LOCATION: (1)..(1062)
<220> FEATURE:
<221> NAME/KEY: mat_peptide
<222> LOCATION: (499)..(1062)

<400> SEQUENCE: 3 gct ccg gcc ccc gtc ccc cag  acc ccc gtc gcc gac  gac agc gcc         45
Ala Pro Ala Pro Val Pro Gln  Thr Pro Val Ala Asp  Asp Ser Ala
    -165                -160                 -155 gcc agc  atg acc gag gcg ctc  aag cgc gac ctc gac  ctc acc tcg         90
Ala Ser  Met Thr Glu Ala Leu  Lys Arg Asp Leu Asp  Leu Thr Ser
    -150                -145                 -140

```
gcc gag gcc gag gag ctt ctc tcg gcg cag gaa gcc gcc atc gag      135
Ala Glu Ala Glu Glu Leu Leu Ser Ala Gln Glu Ala Ala Ile Glu
    -135             -130              -125 acc gac gcc gag gcc acc gag gcc gcg ggc gag gcc tac ggc ggc      180
Thr Asp Ala Glu Ala Thr Glu Ala Ala Gly Glu Ala Tyr Gly Gly
    -120             -115              -110 tca ctg ttc gac acc gag acc ctc gaa ctc acc gtg ctg gtc acc gac  228
Ser Leu Phe Asp Thr Glu Thr Leu Glu Leu Thr Val Leu Val Thr Asp
    -105             -100              -95 gcc tcc gcc gtc gag gcg gtc gag gcc acc gga gcc cag gcc acc gtc  276
Ala Ser Ala Val Glu Ala Val Glu Ala Thr Gly Ala Gln Ala Thr Val
-90             -85              -80              -75 gtc tcc cac ggc acc gag ggc ctg acc gag gtc gtg gag gac ctc aac  324
Val Ser His Gly Thr Glu Gly Leu Thr Glu Val Val Glu Asp Leu Asn
            -70              -65              -60 ggc gcc gag gtt ccc gag agc gtc ctc ggc tgg tac ccg gac gtg gag  372
Gly Ala Glu Val Pro Glu Ser Val Leu Gly Trp Tyr Pro Asp Val Glu
            -55              -50              -45 agc gac acc gtc gtg gtc gag gtg ctg gag ggc tcc gac gcc gac gtc  420
Ser Asp Thr Val Val Val Glu Val Leu Glu Gly Ser Asp Ala Asp Val
            -40              -35              -30 gcc gcc ctg ctc gcc gac gcc ggt gtg gac tcc tcg gtc cgg gtg       468
Ala Ala Leu Leu Ala Asp Ala Gly Val Asp Ser Ser Val Arg Val
    -25             -20              -15 gag gag gcc gag gag gcc ccg cag gtc tac gcc gac atc atc ggc ggc  516
Glu Glu Ala Glu Glu Ala Pro Gln Val Tyr Ala Asp Ile Ile Gly Gly
-10             -5              -1  1               5 ctg gcc tac tac atg ggc ggc cgc tgc tcc gtc ggc ttc gcc gcg acc  564
Leu Ala Tyr Tyr Met Gly Gly Arg Cys Ser Val Gly Phe Ala Ala Thr
            10               15               20 aac agc gcc ggt cag ccc ggt ttc gtc acc gcc ggc cac tgc ggc acc  612
Asn Ser Ala Gly Gln Pro Gly Phe Val Thr Ala Gly His Cys Gly Thr
            25               30               35 gtc ggc acc ggc gtg acc atc ggc aac ggc acc ggc acc ttc cag aac  660
Val Gly Thr Gly Val Thr Ile Gly Asn Gly Thr Gly Thr Phe Gln Asn
    40               45               50 tcg gtc ttc ccc ggc aac gac gcc gcc ttc gtc cgc ggc acc tcc aac  708
Ser Val Phe Pro Gly Asn Asp Ala Ala Phe Val Arg Gly Thr Ser Asn
55               60               65               70 ttc acc ctg acc aac ctg gtc tcg cgc tac aac tcc ggc ggc tac cag  756
Phe Thr Leu Thr Asn Leu Val Ser Arg Tyr Asn Ser Gly Gly Tyr Gln
            75               80               85 tcg gtg acc ggt acc agc cag gcc ccg gcc ggc tcg gcc gtg tgc cgc  804
Ser Val Thr Gly Thr Ser Gln Ala Pro Ala Gly Ser Ala Val Cys Arg
            90               95               100 tcc ggc tcc acc acc ggc tgg cac tgc ggc acc atc cag gcc cgc aac  852
Ser Gly Ser Thr Thr Gly Trp His Cys Gly Thr Ile Gln Ala Arg Asn
            105              110              115 cag acc gtg cgc tac ccg cag ggc acc gtc tac tcg ctc acc cgc acc  900
Gln Thr Val Arg Tyr Pro Gln Gly Thr Val Tyr Ser Leu Thr Arg Thr
    120              125              130 aac gtg tgc gcc gag ccc ggc gac tcc ggc ggt tcg ttc atc tcc ggc  948
Asn Val Cys Ala Glu Pro Gly Asp Ser Gly Gly Ser Phe Ile Ser Gly
135              140              145              150 tcg cag gcc cag ggc gtc acc tcc ggc ggc tcc ggc aac tgc tcc gtc  996
Ser Gln Ala Gln Gly Val Thr Ser Gly Gly Ser Gly Asn Cys Ser Val
            155              160              165 ggc ggc acg acc tac tac cag gag gtc acc ccg atg atc aac tcc tgg  1044
Gly Gly Thr Thr Tyr Tyr Gln Glu Val Thr Pro Met Ile Asn Ser Trp
            170              175              180
```

```
ggt gtc agg atc cgg acc taa                                1065
Gly Val Arg Ile Arg Thr
        185
```

<210> SEQ ID NO 4
<211> LENGTH: 354
<212> TYPE: PRT
<213> ORGANISM: Nocardiopsis dassonvillei subspecies dassonvillei DSM
      43235 ("Protease 18")

<400> SEQUENCE: 4

```
Ala Pro  Ala Pro Val Pro Gln  Thr Pro Val Ala Asp  Asp Ser Ala
    -165             -160              -155

Ala Ser  Met Thr Glu Ala Leu  Lys Arg Asp Leu Asp  Leu Thr Ser
    -150             -145              -140

Ala Glu  Ala Glu Glu Leu Leu  Ser Ala Gln Glu Ala  Ala Ile Glu
    -135             -130              -125

Thr Asp  Ala Glu Ala Thr Glu  Ala Ala Gly Glu Ala  Tyr Gly Gly
    -120             -115              -110

Ser Leu  Phe Asp Thr Glu Thr  Leu Glu Leu Thr Val  Leu Val Thr Asp
    -105             -100              -95

Ala Ser Ala Val Glu Ala Val Glu Ala Thr Gly Ala Gln Ala Thr Val
-90              -85              -80              -75

Val Ser His Gly Thr Glu Gly Leu Thr Glu Val Val Glu Asp Leu Asn
             -70              -65              -60

Gly Ala Glu Val Pro Glu Ser Val Leu Gly Trp Tyr Pro Asp Val Glu
             -55              -50              -45

Ser Asp Thr Val Val Glu Val Leu Glu Gly Ser Asp Ala Asp Val
        -40              -35              -30

Ala Ala Leu Leu Ala Asp Ala Gly Val Asp Ser Ser Val Arg Val
    -25              -20              -15

Glu Glu Ala Glu Glu Ala Pro Gln Val Tyr Ala Asp Ile Ile Gly Gly
-10              -5               -1  1              5

Leu Ala Tyr Tyr Met Gly Gly Arg Cys Ser Val Gly Phe Ala Ala Thr
             10               15               20

Asn Ser Ala Gly Gln Pro Gly Phe Val Thr Ala Gly His Cys Gly Thr
        25               30               35

Val Gly Thr Gly Val Thr Ile Gly Asn Gly Thr Gly Thr Phe Gln Asn
        40               45               50

Ser Val Phe Pro Gly Asn Asp Ala Ala Phe Val Arg Gly Thr Ser Asn
55               60               65               70

Phe Thr Leu Thr Asn Leu Val Ser Arg Tyr Asn Ser Gly Gly Tyr Gln
             75               80               85

Ser Val Thr Gly Thr Ser Gln Ala Pro Ala Gly Ser Ala Val Cys Arg
             90               95              100

Ser Gly Ser Thr Thr Gly Trp His Cys Gly Thr Ile Gln Ala Arg Asn
        105              110              115

Gln Thr Val Arg Tyr Pro Gln Gly Thr Val Tyr Ser Leu Thr Arg Thr
    120              125              130

Asn Val Cys Ala Glu Pro Gly Asp Ser Gly Gly Ser Phe Ile Ser Gly
135              140              145              150

Ser Gln Ala Gln Gly Val Thr Ser Gly Gly Ser Gly Asn Cys Ser Val
             155              160              165

Gly Gly Thr Thr Tyr Tyr Gln Glu Val Thr Pro Met Ile Asn Ser Trp
             170              175              180
```

-continued

Gly Val Arg Ile Arg Thr
          185

<210> SEQ ID NO 5
<211> LENGTH: 1062
<212> TYPE: DNA
<213> ORGANISM: Nocardiopsis prasina DSM 15648 ("Protease 11")
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 5

| gcc | acc | gga | ccg | ctc | ccc | cag | tca | ccc | acc | ccg | gag | gcc | gac | gcc | 45 |
|---|---|---|---|---|---|---|---|---|---|---|---|---|---|---|---|
| Ala | Thr | Gly | Pro | Leu | Pro | Gln | Ser | Pro | Thr | Pro | Glu | Ala | Asp | Ala | |
| -165 | | | | -160 | | | | | -155 | | | | | | |

| gtc | tcc | atg | cag | gag | gcg | ctc | cag | cgc | gac | ctc | ggc | ctg | acc | ccg | 90 |
|---|---|---|---|---|---|---|---|---|---|---|---|---|---|---|---|
| Val | Ser | Met | Gln | Glu | Ala | Leu | Gln | Arg | Asp | Leu | Gly | Leu | Thr | Pro | |
| -150 | | | | -145 | | | | | -140 | | | | | | |

| ctt | gag | gcc | gat | gaa | ctg | ctg | gcc | gcc | cag | gac | acc | gcc | ttc | gag | 135 |
|---|---|---|---|---|---|---|---|---|---|---|---|---|---|---|---|
| Leu | Glu | Ala | Asp | Glu | Leu | Leu | Ala | Ala | Gln | Asp | Thr | Ala | Phe | Glu | |
| -135 | | | | -130 | | | | | -125 | | | | | | |

| gtc | gac | gag | gcc | gcg | gcc | gcg | gcc | gcc | ggg | gac | gcc | tac | ggc | ggc | 180 |
|---|---|---|---|---|---|---|---|---|---|---|---|---|---|---|---|
| Val | Asp | Glu | Ala | Ala | Ala | Ala | Ala | Gly | Asp | Ala | Tyr | Gly | Gly | | |
| -120 | | | | -115 | | | | | -110 | | | | | | |

| tcc | gtc | ttc | gac | acc | gag | acc | ctg | gaa | ctg | acc | gtc | ctg | gtc | acc | gac | 228 |
|---|---|---|---|---|---|---|---|---|---|---|---|---|---|---|---|---|
| Ser | Val | Phe | Asp | Thr | Glu | Thr | Leu | Glu | Leu | Thr | Val | Leu | Val | Thr | Asp | |
| -105 | | | | -100 | | | | | -95 | | | | | -90 | | |

| gcc | gcc | tcg | gtc | gag | gct | gtg | gag | gcc | acc | ggc | gcg | ggt | acc | gaa | ctc | 276 |
|---|---|---|---|---|---|---|---|---|---|---|---|---|---|---|---|---|
| Ala | Ala | Ser | Val | Glu | Ala | Val | Glu | Ala | Thr | Gly | Ala | Gly | Thr | Glu | Leu | |
| | | | | -85 | | | | | -80 | | | | | -75 | | |

| gtc | tcc | tac | ggc | atc | gag | ggc | ctc | gac | gag | atc | atc | cag | gat | ctc | aac | 324 |
|---|---|---|---|---|---|---|---|---|---|---|---|---|---|---|---|---|
| Val | Ser | Tyr | Gly | Ile | Glu | Gly | Leu | Asp | Glu | Ile | Ile | Gln | Asp | Leu | Asn | |
| | | | -70 | | | | | -65 | | | | | -60 | | | |

| gcc | gcc | gac | gcc | gtc | ccc | ggc | gtg | gtc | ggc | tgg | tac | ccg | gac | gtg | gcg | 372 |
|---|---|---|---|---|---|---|---|---|---|---|---|---|---|---|---|---|
| Ala | Ala | Asp | Ala | Val | Pro | Gly | Val | Val | Gly | Trp | Tyr | Pro | Asp | Val | Ala | |
| | | | -55 | | | | | -50 | | | | | -45 | | | |

| ggt | gac | acc | gtc | gtc | ctg | gag | gtc | ctg | gag | ggt | tcc | gga | gcc | gac | gtg | 420 |
|---|---|---|---|---|---|---|---|---|---|---|---|---|---|---|---|---|
| Gly | Asp | Thr | Val | Val | Leu | Glu | Val | Leu | Glu | Gly | Ser | Gly | Ala | Asp | Val | |
| | | | -40 | | | | | -35 | | | | | -30 | | | |

| agc | ggc | ctg | ctc | gcc | gac | gcc | ggc | gtg | gac | gcc | tcg | gcc | gtc | gag | gtg | 468 |
|---|---|---|---|---|---|---|---|---|---|---|---|---|---|---|---|---|
| Ser | Gly | Leu | Leu | Ala | Asp | Ala | Gly | Val | Asp | Ala | Ser | Ala | Val | Glu | Val | |
| -25 | | | | -20 | | | | | -15 | | | | | -10 | | |

| acc | agc | agt | gcg | cag | ccc | gag | ctc | tac | gcc | gac | atc | atc | ggc | ggt | ctg | 516 |
|---|---|---|---|---|---|---|---|---|---|---|---|---|---|---|---|---|
| Thr | Ser | Ser | Ala | Gln | Pro | Glu | Leu | Tyr | Ala | Asp | Ile | Ile | Gly | Gly | Leu | |
| | | | -5 | | | | | -1 | 1 | | | | 5 | | | |

| gcc | tac | acc | atg | ggc | ggc | cgc | tgt | tcg | gtc | gga | ttc | gcg | gcc | acc | aac | 564 |
|---|---|---|---|---|---|---|---|---|---|---|---|---|---|---|---|---|
| Ala | Tyr | Thr | Met | Gly | Gly | Arg | Cys | Ser | Val | Gly | Phe | Ala | Ala | Thr | Asn | |
| | | | 10 | | | | | 15 | | | | | 20 | | | |

| gcc | gcc | ggt | cag | ccc | gga | ttc | gtc | acc | gcc | ggt | cac | tgt | ggc | cgc | gtg | 612 |
|---|---|---|---|---|---|---|---|---|---|---|---|---|---|---|---|---|
| Ala | Ala | Gly | Gln | Pro | Gly | Phe | Val | Thr | Ala | Gly | His | Cys | Gly | Arg | Val | |
| | | 25 | | | | | 30 | | | | | 35 | | | | |

| ggc | acc | cag | gtg | agc | atc | ggc | aac | ggc | cag | ggc | gtc | ttc | gag | cag | tcc | 660 |
|---|---|---|---|---|---|---|---|---|---|---|---|---|---|---|---|---|
| Gly | Thr | Gln | Val | Ser | Ile | Gly | Asn | Gly | Gln | Gly | Val | Phe | Glu | Gln | Ser | |
| 40 | | | | | 45 | | | | | 50 | | | | | 55 | |

| atc | ttc | ccg | ggc | aac | gac | gcc | gcc | ttc | gtc | cgc | ggc | acg | tcc | aac | ttc | 708 |
|---|---|---|---|---|---|---|---|---|---|---|---|---|---|---|---|---|
| Ile | Phe | Pro | Gly | Asn | Asp | Ala | Ala | Phe | Val | Arg | Gly | Thr | Ser | Asn | Phe | |
| | | | | 60 | | | | | 65 | | | | | 70 | | |

| acg | ctg | acc | aac | ctg | gtc | agc | cgc | tac | aac | acc | ggc | ggt | tac | gcc | acc | 756 |
|---|---|---|---|---|---|---|---|---|---|---|---|---|---|---|---|---|
| Thr | Leu | Thr | Asn | Leu | Val | Ser | Arg | Tyr | Asn | Thr | Gly | Gly | Tyr | Ala | Thr | |
| | | | 75 | | | | | 80 | | | | | 85 | | | |

-continued

```
gtc gcc ggc cac aac cag gcg ccc atc ggc tcc tcc gtc tgc cgc tcc      804
Val Ala Gly His Asn Gln Ala Pro Ile Gly Ser Ser Val Cys Arg Ser
             90                  95                 100 ggc tcc acc acc ggc tgg cac tgc ggc acc atc cag gcc cgc ggc cag      852
Gly Ser Thr Thr Gly Trp His Cys Gly Thr Ile Gln Ala Arg Gly Gln
    105                 110                 115 tcg gtg agc tac ccc gag ggc acc gtc acc aac atg acc cgg acc acc      900
Ser Val Ser Tyr Pro Glu Gly Thr Val Thr Asn Met Thr Arg Thr Thr
120                 125                 130                 135 gtg tgc gcc gag ccc ggc gac tcc ggc tcc tac atc tcc ggc aac          948
Val Cys Ala Glu Pro Gly Asp Ser Gly Ser Tyr Ile Ser Gly Asn
                140                 145                 150 cag gcc cag ggc gtc acc tcc ggc ggc tcc ggc aac tgc cgc acc ggc      996
Gln Ala Gln Gly Val Thr Ser Gly Gly Ser Gly Asn Cys Arg Thr Gly
            155                 160                 165 ggg acc acc ttc tac cag gag gtc acc ccc atg gtg aac tcc tgg ggc     1044
Gly Thr Thr Phe Tyr Gln Glu Val Thr Pro Met Val Asn Ser Trp Gly
        170                 175                 180 gtc cgt ctc cgg acc taa                                             1062
Val Arg Leu Arg Thr
    185
```

<210> SEQ ID NO 6
<211> LENGTH: 353
<212> TYPE: PRT
<213> ORGANISM: Nocardiopsis prasina DSM 15648 ("Protease 11")

<400> SEQUENCE: 6

```
Ala  Thr  Gly  Pro  Leu  Pro   Gln  Ser  Pro  Thr  Pro   Glu  Ala  Asp  Ala
-165                 -160                 -155

Val  Ser  Met  Gln  Glu  Ala   Leu  Gln  Arg  Asp  Leu   Gly  Leu  Thr  Pro
-150                 -145                 -140

Leu  Glu  Ala  Asp  Glu  Leu   Leu  Ala  Ala  Gln  Asp   Thr  Ala  Phe  Glu
-135                 -130                 -125

Val  Asp  Glu  Ala  Ala  Ala   Ala  Ala  Ala  Gly  Asp   Ala  Tyr  Gly  Gly
-120                 -115                 -110

Ser  Val  Phe  Asp  Thr  Glu   Thr  Leu  Glu  Leu  Thr   Val  Leu  Val  Thr  Asp
-105                 -100                  -95                  -90

Ala  Ala  Ser  Val  Glu  Ala   Val  Glu  Ala  Thr  Gly   Ala  Gly  Thr  Glu  Leu
                 -85                  -80                  -75

Val  Ser  Tyr  Gly  Ile  Glu   Gly  Leu  Asp  Glu  Ile   Ile  Gln  Asp  Leu  Asn
             -70                  -65                  -60

Ala  Ala  Asp  Ala  Val  Pro   Gly  Val  Gly  Trp  Tyr   Pro  Asp  Val  Ala
        -55                  -50                  -45

Gly  Asp  Thr  Val  Val  Leu   Glu  Val  Leu  Glu  Gly   Ser  Gly  Ala  Asp  Val
    -40                  -35                  -30

Ser  Gly  Leu  Leu  Ala  Asp   Ala  Gly  Val  Asp  Ala   Ser  Ala  Val  Glu  Val
-25                  -20                  -15                  -10

Thr  Ser  Ser  Ala  Gln  Pro   Glu  Leu  Tyr  Ala  Asp   Ile  Ile  Gly  Gly  Leu
             -5                   -1    1                   5

Ala  Tyr  Thr  Met  Gly  Gly   Arg  Cys  Ser  Val  Gly   Phe  Ala  Ala  Thr  Asn
             10                   15                  20

Ala  Ala  Gly  Gln  Pro  Gly   Phe  Val  Thr  Ala  Gly   His  Cys  Gly  Arg  Val
        25                   30                  35

Gly  Thr  Gln  Val  Ser  Ile   Gly  Asn  Gly  Gln  Val   Phe  Glu  Gln  Ser
40                   45                  50                  55

Ile  Phe  Pro  Gly  Asn  Asp   Ala  Ala  Phe  Val  Arg   Gly  Thr  Ser  Asn  Phe
```

-continued

```
                    60                  65                  70
Thr Leu Thr Asn Leu Val Ser Arg Tyr Asn Gly Gly Tyr Ala Thr
            75                  80                  85

Val Ala Gly His Asn Gln Ala Pro Ile Gly Ser Ser Val Cys Arg Ser
            90                  95                 100

Gly Ser Thr Thr Gly Trp His Cys Gly Thr Ile Gln Ala Arg Gly Gln
       105                 110                 115

Ser Val Ser Tyr Pro Glu Gly Thr Val Thr Asn Met Thr Arg Thr Thr
120                 125                 130                 135

Val Cys Ala Glu Pro Gly Asp Ser Gly Gly Ser Tyr Ile Ser Gly Asn
            140                 145                 150

Gln Ala Gln Gly Val Thr Ser Gly Gly Ser Gly Asn Cys Arg Thr Gly
            155                 160                 165

Gly Thr Thr Phe Tyr Gln Glu Val Thr Pro Met Val Asn Ser Trp Gly
            170                 175                 180

Val Arg Leu Arg Thr
            185
```

<210> SEQ ID NO 7
<211> LENGTH: 1062
<212> TYPE: DNA
<213> ORGANISM: Nocardiopsis prasina DSM 15649 ("Protease 35")
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 7

```
gcc  acc  gga  cca  ctc  ccc  cag  tca  ccc  acc  ccg  gag  gcc  gac  gcc            45
Ala  Thr  Gly  Pro  Leu  Pro  Gln  Ser  Pro  Thr  Pro  Glu  Ala  Asp  Ala
-165           -160                 -155 gtc  tcc  atg  cag  gag  gcg  ctc  cag  cgc  gac  ctc  ggc  ctg  acc  ccg            90
Val  Ser  Met  Gln  Glu  Ala  Leu  Gln  Arg  Asp  Leu  Gly  Leu  Thr  Pro
-150           -145                 -140 ctt  gag  gcc  gat  gaa  ctg  ctg  gcc  gcc  cag  gac  acc  gcc  ttc  gag           135
Leu  Glu  Ala  Asp  Glu  Leu  Leu  Ala  Ala  Gln  Asp  Thr  Ala  Phe  Glu
-135           -130                 -125 gtc  gac  gag  gcc  gcg  gcc  gag  gcc  gcc  ggt  gac  gcc  tac  ggc  ggc           180
Val  Asp  Glu  Ala  Ala  Ala  Glu  Ala  Ala  Gly  Asp  Ala  Tyr  Gly  Gly
-120           -115                 -110 tcc  gtc  ttc  gac  acc  gag  acc  ctg  gaa  ctg  acc  gtc  ctg  gtc  acc  gac      228
Ser  Val  Phe  Asp  Thr  Glu  Thr  Leu  Glu  Leu  Thr  Val  Leu  Val  Thr  Asp
-105           -100                 -95                  -90 tcc  gcc  gcg  gtc  gag  gcg  gtg  gag  gcc  acc  ggc  gcc  ggg  acc  gaa  ctg      276
Ser  Ala  Ala  Val  Glu  Ala  Val  Glu  Ala  Thr  Gly  Ala  Gly  Thr  Glu  Leu
               -85                  -80                  -75 gtc  tcc  tac  ggc  atc  acg  ggc  ctc  gac  gag  atc  gtc  gag  gag  ctc  aac      324
Val  Ser  Tyr  Gly  Ile  Thr  Gly  Leu  Asp  Glu  Ile  Val  Glu  Glu  Leu  Asn
               -70                  -65                  -60 gcc  gcc  gac  gcc  gtt  ccc  ggc  gtg  gtc  ggc  tgg  tac  ccg  gac  gtc  gcg      372
Ala  Ala  Asp  Ala  Val  Pro  Gly  Val  Val  Gly  Trp  Tyr  Pro  Asp  Val  Ala
               -55                  -50                  -45 ggt  gac  acc  gtc  gtg  ctg  gag  gtc  ctg  gag  ggt  tcc  ggc  gcc  gac  gtg      420
Gly  Asp  Thr  Val  Val  Leu  Glu  Val  Leu  Glu  Gly  Ser  Gly  Ala  Asp  Val
          -40                  -35                  -30 ggc  ggc  ctg  ctc  gcc  gac  gcc  ggc  gtg  gac  gcc  tcg  gcg  gtc  gag  gtg      468
Gly  Gly  Leu  Leu  Ala  Asp  Ala  Gly  Val  Asp  Ala  Ser  Ala  Val  Glu  Val
          -25                  -20                  -15                  -10
```

```
acc acc acc gag cag ccc gag ctg tac gcc gac atc atc ggc ggt ctg      516
Thr Thr Thr Glu Gln Pro Glu Leu Tyr Ala Asp Ile Ile Gly Gly Leu
            -5              -1  1               5 gcc tac acc atg ggc ggc cgc tgt tcg gtc ggc ttc gcg gcc acc aac      564
Ala Tyr Thr Met Gly Gly Arg Cys Ser Val Gly Phe Ala Ala Thr Asn
         10              15              20 gcc gcc ggt cag ccc ggg ttc gtc acc gcc ggt cac tgt ggc cgc gtg      612
Ala Ala Gly Gln Pro Gly Phe Val Thr Ala Gly His Cys Gly Arg Val
     25              30              35 ggc acc cag gtg acc atc ggc aac ggc cgg ggc gtc ttc gag cag tcc      660
Gly Thr Gln Val Thr Ile Gly Asn Gly Arg Gly Val Phe Glu Gln Ser
40              45              50              55 atc ttc ccg ggc aac gac gcc gcc ttc gtc cgc gga acg tcc aac ttc      708
Ile Phe Pro Gly Asn Asp Ala Ala Phe Val Arg Gly Thr Ser Asn Phe
                60              65              70 acg ctg acc aac ctg gtc agc cgc tac aac acc ggc ggc tac gcc acc      756
Thr Leu Thr Asn Leu Val Ser Arg Tyr Asn Thr Gly Gly Tyr Ala Thr
            75              80              85 gtc gcc ggt cac aac cag gcg ccc atc ggc tcc tcc gtc tgc cgc tcc      804
Val Ala Gly His Asn Gln Ala Pro Ile Gly Ser Ser Val Cys Arg Ser
         90              95             100 ggc tcc acc acc ggt tgg cac tgc ggc acc atc cag gcc cgc ggc cag      852
Gly Ser Thr Thr Gly Trp His Cys Gly Thr Ile Gln Ala Arg Gly Gln
    105             110             115 tcg gtg agc tac ccc gag ggc acc gtc acc aac atg acg cgg acc acc      900
Ser Val Ser Tyr Pro Glu Gly Thr Val Thr Asn Met Thr Arg Thr Thr
120             125             130             135 gtg tgc gcc gag ccc ggc gac tcc ggc ggc tcc tac atc tcc ggc aac      948
Val Cys Ala Glu Pro Gly Asp Ser Gly Gly Ser Tyr Ile Ser Gly Asn
                140             145             150 cag gcc cag ggc gtc acc tcc ggc ggc tcc ggc aac tgc cgc acc ggc      996
Gln Ala Gln Gly Val Thr Ser Gly Gly Ser Gly Asn Cys Arg Thr Gly
            155             160             165 ggg acc acc ttc tac cag gag gtc acc ccc atg gtg aac tcc tgg ggc     1044
Gly Thr Thr Phe Tyr Gln Glu Val Thr Pro Met Val Asn Ser Trp Gly
         170             175             180 gtc cgt ctc cgg acc taa                                             1062
Val Arg Leu Arg Thr
    185

<210> SEQ ID NO 8
<211> LENGTH: 353
<212> TYPE: PRT
<213> ORGANISM: Nocardiopsis prasina DSM 15649 ("Protease 35")

<400> SEQUENCE: 8

Ala  Thr Gly Pro Leu Pro  Gln Ser Pro Thr  Pro Glu Ala Asp Ala
-165                 -160                 -155

Val  Ser Met Gln Glu Ala  Leu Gln Arg Asp  Leu Gly Leu Thr Pro
-150                 -145                 -140

Leu  Glu Ala Asp Glu Leu  Leu Ala Ala Gln Asp  Thr Ala Phe Glu
-135                 -130                 -125

Val  Asp Glu Ala Ala Ala  Glu Ala Ala Gly Asp  Ala Tyr Gly Gly
-120                 -115                 -110

Ser  Val Phe Asp Thr Glu  Thr Leu Glu Leu Thr  Val Leu Val Thr Asp
-105                 -100                 -95                  -90

Ser Ala Ala Val Glu Ala Val Glu Ala Thr Gly Ala Gly Thr Glu Leu
             -85              -80              -75

Val Ser Tyr Gly Ile Thr Gly Leu Asp Glu Ile Val Glu Glu Leu Asn
         -70              -65              -60
```

-continued

```
Ala Ala Asp Ala Val Pro Gly Val Gly Trp Tyr Pro Asp Val Ala
    -55                 -50                 -45

Gly Asp Thr Val Val Leu Glu Val Leu Glu Gly Ser Gly Ala Asp Val
    -40                 -35                 -30

Gly Gly Leu Leu Ala Asp Ala Gly Val Asp Ala Ser Ala Val Glu Val
-25                 -20                 -15                 -10

Thr Thr Thr Glu Gln Pro Glu Leu Tyr Ala Asp Ile Ile Gly Gly Leu
            -5                  -1  1                   5

Ala Tyr Thr Met Gly Gly Arg Cys Ser Val Gly Phe Ala Ala Thr Asn
            10                  15                  20

Ala Ala Gly Gln Pro Gly Phe Val Thr Ala Gly His Cys Gly Arg Val
            25                  30                  35

Gly Thr Gln Val Thr Ile Gly Asn Gly Arg Gly Val Phe Glu Gln Ser
40                  45                  50                  55

Ile Phe Pro Gly Asn Asp Ala Ala Phe Val Arg Gly Thr Ser Asn Phe
            60                  65                  70

Thr Leu Thr Asn Leu Val Ser Arg Tyr Asn Thr Gly Gly Tyr Ala Thr
            75                  80                  85

Val Ala Gly His Asn Gln Ala Pro Ile Gly Ser Ser Val Cys Arg Ser
            90                  95                  100

Gly Ser Thr Thr Gly Trp His Cys Gly Thr Ile Gln Ala Arg Gly Gln
    105                 110                 115

Ser Val Ser Tyr Pro Glu Gly Thr Val Thr Asn Met Thr Arg Thr Thr
120                 125                 130                 135

Val Cys Ala Glu Pro Gly Asp Ser Gly Gly Ser Tyr Ile Ser Gly Asn
            140                 145                 150

Gln Ala Gln Gly Val Thr Ser Gly Gly Ser Gly Asn Cys Arg Thr Gly
            155                 160                 165

Gly Thr Thr Phe Tyr Gln Glu Val Thr Pro Met Val Asn Ser Trp Gly
            170                 175                 180

Val Arg Leu Arg Thr
    185

<210> SEQ ID NO 9
<211> LENGTH: 1068
<212> TYPE: DNA
<213> ORGANISM: Nocardiopsis alba DSM 15647 ("Protease 08")
<220> FEATURE:
<221> NAME/KEY: CDS
<222> LOCATION: (1)..(1065)
<220> FEATURE:
<221> NAME/KEY: mat_peptide
<222> LOCATION: (502)..(1065)

<400> SEQUENCE: 9 gcg acc ggc ccc ctc ccc cag tcc ccc acc ccg gat gaa gcc gag       45
Ala Thr Gly Pro Leu Pro Gln Ser Pro Thr Pro Asp Glu Ala Glu
    -165                -160                -155 gcc acc acc atg gtc gag gcc ctc cag cgc gac ctc ggc ctg tcc       90
Ala Thr Thr Met Val Glu Ala Leu Gln Arg Asp Leu Gly Leu Ser
    -150                -145                -140 ccc tct cag gcc gac gag ctc ctc gag gcg cag gcc gag tcc ttc      135
Pro Ser Gln Ala Asp Glu Leu Leu Glu Ala Gln Ala Glu Ser Phe
    -135                -130                -125 gag atc gac gag gcc gcc acc gcg gcc gca gcc gac tcc tac ggc      180
Glu Ile Asp Glu Ala Ala Thr Ala Ala Ala Ala Asp Ser Tyr Gly
    -120                -115                -110 ggc tcc atc ttc gac acc gac agc ctc acc ctg acc gtc ctg gtc acc  228
```

```
                   Gly Ser Ile  Phe Asp Thr Asp Ser  Leu Thr Leu Thr Val Leu Val Thr
                       -105              -100                 -95 gac gcc tcc gcc gtc gag gcg gtc gag gcc gcc ggc gcc gag gcc aag           276
Asp Ala Ser Ala Val Glu Ala Val Glu Ala Ala Gly Ala Glu Ala Lys
    -90              -85              -80 gtg gtc tcg cac ggc atg gag ggc ctg gag gag atc gtc gcc gac ctg           324
Val Val Ser His Gly Met Glu Gly Leu Glu Glu Ile Val Ala Asp Leu
-75              -70              -65                   -60 aac gcg gcc gac gct cag ccc ggc gtc gtg ggc tgg tac ccc gac atc           372
Asn Ala Ala Asp Ala Gln Pro Gly Val Val Gly Trp Tyr Pro Asp Ile
                 -55              -50                   -45 cac tcc gac acg gtc gtc ctc gag gtc ctc gag ggc tcc ggt gcc gac           420
His Ser Asp Thr Val Val Leu Glu Val Leu Glu Gly Ser Gly Ala Asp
             -40              -35                  -30 gtg gac tcc ctg ctc gcc gac gcc ggt gtg gac acc gcc gac gtc aag           468
Val Asp Ser Leu Leu Ala Asp Ala Gly Val Asp Thr Ala Asp Val Lys
         -25              -20                  -15 gtg gag agc acc acc gag cag ccc gag ctg tac gcc gac atc atc ggc           516
Val Glu Ser Thr Thr Glu Gln Pro Glu Leu Tyr Ala Asp Ile Ile Gly
    -10               -5              -1   1              5 ggt ctc gcc tac acc atg ggt ggg cgc tgc tcg gtc ggc ttc gcg gcc           564
Gly Leu Ala Tyr Thr Met Gly Gly Arg Cys Ser Val Gly Phe Ala Ala
                 10              15                  20 acc aac gcc tcc ggc cag ccc ggg ttc gtc acc gcc ggc cac tgc ggc           612
Thr Asn Ala Ser Gly Gln Pro Gly Phe Val Thr Ala Gly His Cys Gly
             25              30                  35 acc gtc ggc acc ccg gtc agc atc ggc aac ggc cag ggc gtc ttc gag           660
Thr Val Gly Thr Pro Val Ser Ile Gly Asn Gly Gln Gly Val Phe Glu
         40              45                  50 cgt tcc gtc ttc ccc ggc aac gac tcc gcc ttc gtc cgc ggc acc tcg           708
Arg Ser Val Phe Pro Gly Asn Asp Ser Ala Phe Val Arg Gly Thr Ser
    55              60                  65 aac ttc acc ctg acc aac ctg gtc agc cgc tac aac acc ggt ggt tac           756
Asn Phe Thr Leu Thr Asn Leu Val Ser Arg Tyr Asn Thr Gly Gly Tyr
70              75                  80                  85 gcg acc gtc tcc ggc tcc tcg cag gcg gcg atc ggc tcg cag atc tgc           804
Ala Thr Val Ser Gly Ser Ser Gln Ala Ala Ile Gly Ser Gln Ile Cys
            90              95                  100 cgt tcc ggc tcc acc acc ggc tgg cac tgc ggc acc gtc cag gcc cgc           852
Arg Ser Gly Ser Thr Thr Gly Trp His Cys Gly Thr Val Gln Ala Arg
        105              110                  115 ggc cag acg gtg agc tac ccc cag ggc acc gtg cag aac ctg acc cgc           900
Gly Gln Thr Val Ser Tyr Pro Gln Gly Thr Val Gln Asn Leu Thr Arg
    120              125                  130 acc aac gtc tgc gcc gag ccc ggt gac tcc ggc ggc tcc ttc atc tcc           948
Thr Asn Val Cys Ala Glu Pro Gly Asp Ser Gly Gly Ser Phe Ile Ser
    135              140                  145 ggc agc cag gcc cag ggc gtc acc tcc ggt ggc tcc ggc aac tgc tcc           996
Gly Ser Gln Ala Gln Gly Val Thr Ser Gly Gly Ser Gly Asn Cys Ser
150              155                  160                  165 ttc ggt ggc acc acc tac tac cag gag gtc aac ccg atg ctg agc agc          1044
Phe Gly Gly Thr Thr Tyr Tyr Gln Glu Val Asn Pro Met Leu Ser Ser
             170                  175                  180 tgg ggt ctg acc ctg cgc acc tga                                          1068
Trp Gly Leu Thr Leu Arg Thr
             185

<210> SEQ ID NO 10
<211> LENGTH: 355
<212> TYPE: PRT
<213> ORGANISM: Nocardiopsis alba DSM 15647 ("Protease 08")
```

<400> SEQUENCE: 10

```
Ala Thr Gly Pro Leu Pro Gln Ser Pro Thr Pro Asp Glu Ala Glu
        -165             -160            -155

Ala Thr Thr Met Val Glu Ala Leu Gln Arg Asp Leu Gly Leu Ser
        -150             -145            -140

Pro Ser Gln Ala Asp Glu Leu Leu Glu Ala Gln Ala Glu Ser Phe
        -135             -130            -125

Glu Ile Asp Glu Ala Ala Thr Ala Ala Ala Ala Asp Ser Tyr Gly
        -120             -115            -110

Gly Ser Ile Phe Asp Thr Asp Ser Leu Thr Leu Thr Val Leu Val Thr
        -105             -100             -95

Asp Ala Ser Ala Val Glu Ala Val Glu Ala Ala Gly Ala Glu Ala Lys
     -90             -85              -80

Val Val Ser His Gly Met Glu Gly Leu Glu Glu Ile Val Ala Asp Leu
-75              -70              -65                   -60

Asn Ala Ala Asp Ala Gln Pro Gly Val Val Gly Trp Tyr Pro Asp Ile
         -55              -50              -45

His Ser Asp Thr Val Val Leu Gly Val Leu Glu Gly Ser Gly Ala Asp
         -40              -35              -30

Val Asp Ser Leu Leu Ala Asp Ala Gly Val Asp Thr Ala Asp Val Lys
         -25              -20              -15

Val Glu Ser Thr Thr Glu Gln Pro Glu Leu Tyr Ala Asp Ile Ile Gly
-10               -5               -1   1                     5

Gly Leu Ala Tyr Thr Met Gly Gly Arg Cys Ser Val Gly Phe Ala Ala
                 10               15                    20

Thr Asn Ala Ser Gly Gln Pro Gly Phe Val Thr Ala Gly His Cys Gly
         25                 30                    35

Thr Val Gly Thr Pro Val Ser Ile Gly Asn Gly Gln Gly Val Phe Glu
         40                 45                    50

Arg Ser Val Phe Pro Gly Asn Asp Ser Ala Phe Val Arg Gly Thr Ser
55                   60                    65

Asn Phe Thr Leu Thr Asn Leu Val Ser Arg Tyr Asn Thr Gly Gly Tyr
70                   75                    80                    85

Ala Thr Val Ser Gly Ser Ser Gln Ala Ala Ile Gly Ser Gln Ile Cys
         90                 95                    100

Arg Ser Gly Ser Thr Thr Gly Trp His Cys Gly Thr Val Gln Ala Arg
         105                110                   115

Gly Gln Thr Val Ser Tyr Pro Gln Gly Thr Val Gln Asn Leu Thr Arg
         120                125                   130

Thr Asn Val Cys Ala Glu Pro Gly Asp Ser Gly Gly Ser Phe Ile Ser
         135                140                   145

Gly Ser Gln Ala Gln Gly Val Thr Ser Gly Ser Gly Asn Cys Ser
150                  155                  160                   165

Phe Gly Gly Thr Thr Tyr Tyr Gln Glu Val Asn Pro Met Leu Ser Ser
                 170                175                  180

Trp Gly Leu Thr Leu Arg Thr
                 185
```

<210> SEQ ID NO 11
<211> LENGTH: 27
<212> TYPE: DNA
<213> ORGANISM: Artificial Sequence
<220> FEATURE:
<223> OTHER INFORMATION: Primer -continued

```
<400> SEQUENCE: 11
ccgattatgg agcggattga acatgcg                                           27

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gtgaccatcg gcgacggcag gggcgtcttc g                                      31

<210> SEQ ID NO 13
<211> LENGTH: 10172
<212> TYPE: DNA
<213> ORGANISM: Artificial Sequence
<220> FEATURE:
<223> OTHER INFORMATION: Expression Cassette
<220> FEATURE:
<221> NAME/KEY: source
<222> LOCATION: (1)..(3323)
<223> OTHER INFORMATION: Bacillus subtilis genome sequence including
      yfmH-yfmD-yfmC-yfmB-yfmA genes
<220> FEATURE:
<221> NAME/KEY: misc_recomb
<222> LOCATION: (3561)..(4208)
<223> OTHER INFORMATION: Cat gene providing chloramphenicol resistance
<220> FEATURE:
<221> NAME/KEY: promoter
<222> LOCATION: (4523)..(5633)
<223> OTHER INFORMATION: Triple PamyL-scBAN-CryIIIA promoter including
      mRNA stabilizing sequence
<220> FEATURE:
<221> NAME/KEY: sig_peptide
<222> LOCATION: (5658)..(5738)
<220> FEATURE:
<221> NAME/KEY: CDS
<222> LOCATION: (5658)..(6797)
<220> FEATURE:
<221> NAME/KEY: mat_peptide
<222> LOCATION: (6234)..(6797)
<220> FEATURE:
<221> NAME/KEY: source
<222> LOCATION: (6839)..(7540)
<223> OTHER INFORMATION: Part of Bacillus subtilis pectate lyase gene
<220> FEATURE:
<221> NAME/KEY: source
<222> LOCATION: (7541)..(10172)
<223> OTHER INFORMATION: Bacillus subtilis genome DNA inclding yflS-citM
      genes

<400> SEQUENCE: 13
gagtatcgcc agtaagggggc gttttgttt tctggttgtt ttcttcattt caggtttcgc        60
cctttccttg ccaaatataa gaaaaacggc gttccgataa tcgcggtgac aatgccgacc       120
ggtgattcat aaggaaatgc aatccatctg gccagaacat ctgcgtacac cagcaaaatg       180
gcaccgaaca gtgccgaaaa cggaagcacg tattgataat gttctccgat cagcttgcgg       240
acaatatgcg ggacgagcag cccgacaaag ccaatcggcc cggcgacggc tacggaagcg       300
ccggaaagaa ttaaaataat caaactgatc agaatcctga tgccgttcat attttgtcca       360
agcccttttg ctgtttcgtc tccgagaccg agaacagaaa cagaaccgga aaatacgagg       420
gcaagcccga tgccaatgac agaaaaagga gcgatggtta tgacgtcctg ccagttgctg       480
ccgtcgattg cgcctgtcat ccagtacaga acatcctcac ctgactcatt taaaataatg       540
atggcctgtg tcatagagga gaggaacaag tgcacggcca ttcctgacag cgccagcttg       600
acaggcgtca ttccgccgga tgaggcaatc atatacacaa tcgcgccgcc tgctgccgca       660
```

-continued

```
cccgcaaaag cgaatataac agatgaatag ggcgatgccg gcagaatgac gagagaagca    720
acaacaaaaa gcgatgcacc cgcattcaca ccgaaaattt ggggtgaagc cagaggattt    780
ctggtcatag cctgcatcag cgccctgct acagctaggc tggcgccgac aaaaacgccg     840
attaatgtgc ggggaaggcg aagagtagag atgatgagct gttcctttga accgtcccat    900
acaaaaagat atttcaatga atctatgatg ctgatgtctg aggctcctac tgaaagattc    960
agcccaagcc caaatataaa aataatcagt gcaatgataa acatcatcag tcttgatgat   1020
gagcgccgtt tggctgaatg atacaacagt ctcacttcct tactgcgtct ggttgcaaaa   1080
acgaagaagc aaggattccc ctcgcttctc atttgtccta tttattatac acttttttaa   1140
gcacatcttt ggcgcttgtt tcactagact tgatgcctct gaatcttgtc caagtgtcac   1200
ggtccgcatc atagacttgt ccattttca ccgctttgag attttccag agcgggttcg     1260
ttttccactc atctacaatg gttttgcctt cgttggctga gatgaacaaa atatcaggat   1320
cgatttttgct caattgctca aggctgacct cttgataggc gttatctgac ttcacagcgt   1380
gtgtaaagcc tagcatttta aagatttctc cgtcatagga tgatgatgta tgaagctgga   1440
aggaatccgc tcttgcaacg ccgagaacga tgttgcggtt ttcatctttc ggaagttcgg   1500
cttttagatc gttgatgact tttttgtgct cggcaagctt ttcttttcct tcatcttctt   1560
tatttaatgc tttagcaatg gtcgtaaagc tgtcgatcgt ttcgtcatat gtcgcttcac   1620
ggcttttta ttcaatcgtc ggggcgattt ttttcagctg tttataaatg tttttatggc    1680
gctcagcgtc agcgatgatt aaatcaggct tcaaggaact gatgacctca agattgggtt   1740
cgctgcgtgt gcctacagat gtgtaatcaa tggagctgcc gacaagcttt ttaatcatat   1800
cttttttgtt gtcatctgcg atgcccaccg gcgtaatgcc gagattgtga acggcatcca   1860
agaatgaaag ctcaagcaca accacccgct taggtgtgcc gcttactgtc gttttttcctt  1920
cttcgtcatg gatcactctg gaatcctag actcgctttt gccgcttccg ttgttattct    1980
ggcttgatga acagccggat acaatgaggc aggcgagcaa taaaacactc atgatggcaa   2040
tcaacttgtt agaataggtg cgcatgtcat tcttccttt ttcagattta gtaatgagaa    2100
tcattatcac atgtaacact ataatagcat ggcttatcat gtcaatattt ttttagtaaa   2160
gaaagctgcg ttttactgc tttctcatga aagcatcatc agacacaaat aagtggtatg    2220
cagcgttacc gtgtcttcga gacaaaaacg catgggcgtt ggcttagag gtttcgaaca    2280
tatcagcagt gacataagga aggagagtgc tgagataacc ggacaatttc ttttctattt   2340
catctgttag tgcaaattca atgtcgccga tattcatgat aatcgagaaa acaagtcga    2400
tatcgatatg aaaatgttcc tcggcaaaaa ccgcaagctc gtgaattcct ggtgaacatc    2460
cggcacgctt atggaaaatc tgtttgacta aatcactcac aatccaagca ttgtattgct   2520
gttctggtga aaagtattgc attagacata cctcctgctc gtacggataa aggcagcgtt   2580
tcatggtcgt gtgctccgtg cagcggcttc tccttaattt tgatttttct gaaaataggt   2640
cccgttccta tcactttacc atggacggaa acaaatagc tactaccatt cctcctgttt    2700
ttctcttcaa tgttctggaa tctgtttcag gtacagacga tcgggtatga agaaaatata   2760
gaaaacatga aggaggaata tcgacatgaa accagttgta aaagagtata caaatgacga   2820
acagctcatg aaagatgtag aggaattgca gaaaatgggt gttgcgaaag aggatgtata   2880
cgtcttagct cacgacgatg acagaacgga acgcctggct gacaacacga acgccaacac   2940
gatcggagcc aaagaaacag gtttcaagca cgcggtggga aatatcttca ataaaaaagg   3000
agacgagctc cgcaataaaa ttcacgaaat cggttttttct gaagatgaag ccgctcaatt   3060
```

```
tgaaaaacgc ttagatgaag gaaaagtgct tctctttgtg acagataacg aaaaagtgaa    3120
agcttgggca taaagcaagg aaaaaaccaa aaggccaatg tcggccttt  ggttttttg     3180 cggtctttgc ggtgggattt tgcagaatgc cgcaatagga tagcggaaca ttttcggttc    3240
tgaatgtccc tcaatttgct attatatttt tgtgataaat tggaataaaa tctcacaaaa    3300
tagaaaatgg gggtacatag tggccatcat ggccagctag catgcacatg ggatctggga    3360
ccaataataa tgactagaga agaaagaatg aagattgttc atgaaattaa ggaacgaata    3420
ttggataaag tggggtattt ttaaaatata tatttatgtt acagtaatat tgacttttaa    3480
aaaaggattg attctaagaa gaaagcagac aagtaagcct cctaaattca ctttagataa    3540
aaatttagga ggcatatcaa atgaacttta ataaaattga tttagacaat tggaagagaa    3600
aagagatatt taatcattat ttgaaccaac aaacgacttt tagtataacc acagaaattg    3660
atattagtgt tttataccga aacataaaac aagaaggata taaattttac cctgcattta    3720 tttcttagt  gacaagggtg ataaactcaa atacagcttt tagaactggt tacaatagcg    3780
acggagagtt aggttattgg gataagttag agccacttta tacaattttt gatggtgtat    3840
ctaaaacatt ctctggtatt tggactcctg taaagaatga cttcaaagag ttttatgatt    3900 tataccttc  tgatgtagag aaatataatg gttcggggaa attgtttccc aaaacaccta    3960
tacctgaaaa tgcttttct  ctttctatta ttccatggac ttcatttact gggtttaact    4020
taaatatcaa taataatagt aattaccttc tacccattat tacagcagga aaattcatta    4080
ataaaggtaa ttcaatatat ttaccgctat ctttacaggt acatcattct gtttgtgatg    4140
gttatcatgc aggattgttt atgaactcta ttcaggaatt gtcagatagg cctaatgact    4200
ggcttttata atatgagata atgccgactg tactttttac agtcggtttt ctaacgatac    4260
attaataggt acgaaaaagc aacttttttt gcgcttaaaa ccagtcatac caataactta    4320
agggtaacta gcctcgccgg aaagagcgaa aatgcctcac atttgtgcca cctaaaaagg    4380
agcgatttac atatgagtta tgcagtttgt agaatgcaaa aagtgaaatc agctggacta    4440
aaaggcatgg catgccttcg atagtttatt aatattagtg gagctcagtg agagcgaagc    4500
gaacacttga ttttttaatt ttctatcttt tataggtcat tagagtatac ttatttgtcc    4560
tataaactat ttagcagcat aatagattta ttgaataggt catttaagtt gagcatatta    4620
ggggaggaaa atcttggaga aatatttgaa gaacccgagg atctagatca ggtaccgcaa    4680
cgttcgcaga tgctgctgaa gagattatta aaaagctgaa agcaaaaggc tatcaattgg    4740
taactgtatc tcagcttgaa gaagtgaaga agcagagagg ctattgaata aatgagtaga    4800
aagcgccata tcggcgcttt tcttttggaa gaaaatatag ggaaaatggt acttgttaaa    4860
aattcggaat atttatacaa tatcatatgt atcacattga aaggagggggc ctgctgtcca    4920 gactgtccgc tgtgtaaaaa aaaggaataa agggggggttg acattatttt actgatatgt    4980
ataatataat ttgtataaga aaatggaggg gccctcgaaa cgtaagatga aaccttagat    5040
aaaagtgctt ttttgttgc  aattgaagaa ttattaatgt taagcttaat taaagataat    5100
atctttgaat tgtaacgccc ctcaaaagta agaactacaa aaaagaata  cgttatatag    5160 aaatatgttt gaaccttctt cagattacaa atatattcgg acggactcta cctcaaatgc    5220
ttatctaact atagaatgac atacaagcac aaccttgaaa atttgaaaat ataactacca    5280
atgaacttgt tcatgtgaat tatcgctgta tttaattttc tcaattcaat atataatatg    5340
ccaatacatt gttacaagta gaaattaaga caccccttgat agccttacta tacctaacat    5400
gatgtagtat taaatgaata tgtaaatata tttatgataa gaagcgactt atttataatc    5460
```

```
attacatatt tttctattgg aatgattaag attccaatag aatagtgtat aaattattta    5520
tcttgaaagg agggatgcct aaaaacgaag aacattaaaa acatatattt gcaccgtcta    5580
atggatttat gaaaaatcat tttatcagtt tgaaaattat gtattatgga gctctgaaaa    5640
aaaggagagg ataaaga atg aag aaa ccg ttg ggg aaa att gtc gca agc       5690
                Met Lys Lys Pro Leu Gly Lys Ile Val Ala Ser
                   -190              -185 acc gca cta ctc att tct gtt gct ttt agt tca tcg atc gca tcg          5735
Thr Ala Leu Leu Ile Ser Val Ala Phe Ser Ser Ser Ile Ala Ser
    -180              -175              -170 gct gcc acc gga gcg ctc ccc cag tca ccc acc ccg gag gcc gac          5780
Ala Ala Thr Gly Ala Leu Pro Gln Ser Pro Thr Pro Glu Ala Asp
    -165              -160              -155 gcg gtc tcc atg cag gag gcg ctc cag cgc gac ctc gac ctg acc          5825
Ala Val Ser Met Gln Glu Ala Leu Gln Arg Asp Leu Asp Leu Thr
    -150              -145              -140 tcc gcc gag gcc gag gag ctg ctg gcc gcc cag gac acc gcc ttc          5870
Ser Ala Glu Ala Glu Glu Leu Leu Ala Ala Gln Asp Thr Ala Phe
    -135              -130              -125 gag gtc gac gag gcc gcg gcc gag gcc gcc ggg gac gcc tac ggc          5915
Glu Val Asp Glu Ala Ala Ala Glu Ala Ala Gly Asp Ala Tyr Gly
    -120              -115              -110 ggc tcc gtc ttc gac acc gag agc ctg gaa ctg acc gtc ctg gtc acc      5963
Gly Ser Val Phe Asp Thr Glu Ser Leu Glu Leu Thr Val Leu Val Thr
    -105              -100               -95 gat gcc gcc gcg gtc gag gcc gtg gag gcc acc ggc gcc ggg acc gag      6011
Asp Ala Ala Ala Val Glu Ala Val Glu Ala Thr Gly Ala Gly Thr Glu
 -90              -85               -80              -75 ctg gtc tcc tac ggc atc gac ggt ctc gac gag atc gtc cag gag ctc      6059
Leu Val Ser Tyr Gly Ile Asp Gly Leu Asp Glu Ile Val Gln Glu Leu
             -70               -65               -60 aac gcc gcc gac gcc gtt ccc ggt gtg gtc ggc tgg tac ccg gac gtg      6107
Asn Ala Ala Asp Ala Val Pro Gly Val Val Gly Trp Tyr Pro Asp Val
             -55               -50               -45 gcg ggt gac acc gtc gtc ctg gag gtc ctg gag ggt tcc gga gcc gac      6155
Ala Gly Asp Thr Val Val Leu Glu Val Leu Glu Gly Ser Gly Ala Asp
         -40               -35               -30 gtc agc ggc ctg ctc gcg gac gcc ggc gtg gac gcc tcg gcc gtc gag      6203
Val Ser Gly Leu Leu Ala Asp Ala Gly Val Asp Ala Ser Ala Val Glu
         -25               -20               -15 gtg acc acg agc gac cag ccc gag ctc tac gcc gac atc atc ggt ggt      6251
Val Thr Thr Ser Asp Gln Pro Glu Leu Tyr Ala Asp Ile Ile Gly Gly
 -10               -5               -1   1                5 ctg gcc tac acc atg ggc ggc cgc tgt tcg gtc ggc ttc gcg gcc acc      6299
Leu Ala Tyr Thr Met Gly Gly Arg Cys Ser Val Gly Phe Ala Ala Thr
             10                15                20 aac gcc gcc ggt cag ccc ggg ttc gtc acc gcc ggt cac tgc ggc cgc      6347
Asn Ala Ala Gly Gln Pro Gly Phe Val Thr Ala Gly His Cys Gly Arg
             25                30                35 gtg ggc acc cag gtg acc atc ggc aac ggc agg ggc gtc ttc gag cag      6395
Val Gly Thr Gln Val Thr Ile Gly Asn Gly Arg Gly Val Phe Glu Gln
     40                45                50 tcc gtc ttc ccc ggc aac gac gcg gcc ttc gtc cgc ggt acg tcc aac      6443
Ser Val Phe Pro Gly Asn Asp Ala Ala Phe Val Arg Gly Thr Ser Asn
55                60                65                 70 ttc acg ctg acc aac ctg gtc agc cgc tac aac acc ggc ggg tac gcc      6491
Phe Thr Leu Thr Asn Leu Val Ser Arg Tyr Asn Thr Gly Gly Tyr Ala
                 75                80                 85 acg gtc gcc ggt cac aac cag gcc ccc atc ggc tcc tcc gtc tgc cgc      6539
Thr Val Ala Gly His Asn Gln Ala Pro Ile Gly Ser Ser Val Cys Arg
```

```
                      90                  95                 100
tcc ggc tcc acc acc ggt tgg cac tgc ggc acc atc cag gcc cgc ggc    6587
Ser Gly Ser Thr Thr Gly Trp His Cys Gly Thr Ile Gln Ala Arg Gly
        105                 110                115 cag tcg gtg agc tac ccc gag ggc acc gtc acc aac atg acc cgg acc    6635
Gln Ser Val Ser Tyr Pro Glu Gly Thr Val Thr Asn Met Thr Arg Thr
    120                 125                 130 acc gtg tgc gcc gag ccc ggc gac tcc ggc ggc tcc tac atc tcc ggc    6683
Thr Val Cys Ala Glu Pro Gly Asp Ser Gly Gly Ser Tyr Ile Ser Gly
135                 140                 145                 150 acc cag gcc cag ggc gtg acc tcc ggc ggc tcc ggc aac tgc cgc acc    6731
Thr Gln Ala Gln Gly Val Thr Ser Gly Gly Ser Gly Asn Cys Arg Thr
                155                 160                 165 ggc ggg acc acc ttc tac cag gag gtc acc ccc atg gtg aac tcc tgg    6779
Gly Gly Thr Thr Phe Tyr Gln Glu Val Thr Pro Met Val Asn Ser Trp
                170                 175                 180 ggc gtc cgt ctc cgg acc taatcgcatg ttcaatccgc tccataatcg           6827
Gly Val Arg Leu Arg Thr
                185 gtcgacgcgg cggttcgcgt ccggacagca catcaccgaa atattatgga agaaaatatc    6887 agcaccatga cggccaaacg gatgcttcca acggtgctaa ctatatcacg atgtcctaca    6947 actattatca cgatcatgat aaaagctcca tttttcggatc aagtgacagc aaaacctccg    7007 atgacggcaa attaaaaatt acgctgcatc ataaccgcta taaaaatatt gtccagcgcg    7067 cgccgagagt ccgcttcggg caagtgcacg tatacaacaa ctattatgaa ggaagcacaa    7127 gctcttcaag ttatccttttt agctatgcat ggggaatcgg aaagtcatct aaaatctatg    7187 cccaaaacaa tgtcattgac gtaccggac tgtcagctgc taaaacgatc agcgtattca    7247 gcggggggaac ggctttatat gactccggca cgttgctgaa cggcacacag atcaacgcat    7307 cggctgcaaa cgggctgagc tcttctgtcg gctggacgcc gtctctgcat ggatcgattg    7367 atgcttctgc taatgtgaaa tcaaatgtta taaatcaagc gggtgcgggt aaattaaatt    7427 aagaaagtga aaacacaaa gggtgctaac ctttgtgttt tttaattaat taaaatgttt     7487 attaacttag ttaaggagta gaatggaaaa ggggatcgga aaacaagtat ataggaggag    7547 acctatttat ggcttcagaa aaagacgcag gaaaacagtc agcagtaaag cttgttccat    7607 tgcttattac tgtcgctgtg ggactaatca tctggtttat tcccgctccg tccggacttg    7667 aacctaaagc ttggcatttg tttgcgattt ttgtcgcaac aattatcggc tttatctcca    7727 agcccttgcc aatgggtgca attgcaattt ttgcattggc ggttactgca ctaactggaa    7787 cactatcaat tgaggataca ttaagcggat tcgggaataa gaccatttgg cttatcgtta    7847 tcgcattctt tatttcccgg ggatttatca aaaccggtct cggtgcgaga atttcgtatg    7907 tattcgttca gaaattcgga aaaaaaccc ttggactttc ttattcactg ctattcagtg     7967 atttaatact ttcacctgct attccaagta atacggcgcg tgcaggaggc attatatttc    8027 ctattatcag atcattatcc gaaacattcg gatcaagccc ggcaaatgga acagagagaa    8087 aaatcggtgc attcttatta aaaaccggtt tcaggggaa tctgatcaca tctgctatgt    8147 tcctgacagc gatggcggcg aacccgctga ttgccaagct ggcccatgat gtcgcagggg    8207 tggacttaac atggacaagc tgggcaattg ccgcgattgt accgggactt gtaagcttaa    8267 tcatcacgcc gcttgtgatt tacaaactgt atccgccgga aatcaaagaa acaccggatg    8327 cggcgaaaat cgcaacagaa aaactgaaag aaatgggacc gttcaaaaaa tcggagcttt    8387 ccatggttat cgtgtttctt ttggtgcttg tgctgtggat ttttggcggc agcttcaaca    8447
```

```
tcgacgctac cacaaccgca ttgatcggtt tggccgttct cttattatca caagttctga    8507
cttgggatga tatcaagaaa gaacagggcg cttgggatac gctcacttgg tttgcggcgc    8567
ttgtcatgct cgccaacttc ttgaatgaat taggcatggt gtcttggttc agtaatgcca    8627
tgaaatcatc cgtatcaggg ttctcttgga ttgtggcatt catcatttta attgttgtgt    8687
attattactc tcactatttc tttgcaagtg cgacagccca catcagtgcg atgtattcag    8747 cattttggc tgtcgtcgtg gcagcgggcg caccgccgct tttagcagcg ctgagcctcg     8807
cgttcatcag caacctgttc gggtcaacga ctcactacgg ttctggagcg ctccggtct     8867 tcttcggagc aggctacatc ccgcaaggca aatggtggtc catcggattt atcctgtcga    8927
ttgttcatat catcgtatgg cttgtgatcg gcggattatg gtggaaagta ctaggaatat    8987
ggtagaaaga aaaaggcaga cgcggtctgc ctttttttat tttcactcct tcgtaagaaa    9047
atggattttg aaaaatgaga aaattccctg tgaaaaatgg tatgatctag gtagaaagga    9107
cggctggtgc tgtggtgaaa aagcggttcc attttttccct gcaaacaaaa ataatggggc   9167
tgattgcggc tctgctggtc tttgtcattg gtgtgctgac cattacgtta gccgttcagc    9227
atacacaggg agaacggaga caggcagagc agctggcggt tcaaacggcg agaaccattt    9287
cctatatgcc gccggttaaa gagctcattg agagaaaaga cggacatgcg gctcagacgc    9347
aagaggtcat tgaacaaatg aaagaacaga ctggtgcgtt tgccatttat gttttgaacg    9407
aaaaaggaga cattcgcagc gcctctggaa aaagcggatt aaagaaactg gagcgcagca    9467
gagaaatttt gtttggcggt tcgcatgttt ctgaaacaaa agcggatgga cgaagagtga    9527
tcagagggag cgcgccgatt ataaaagaac agaagggata cagccaagtg atcggcagcg    9587
tgtctgttga ttttctgcaa acggagacag agcaaagcat caaaaagcat ttgagaaatt    9647
tgagtgtgat tgctgtgctt gtactgctgc tcggatttat tggcgccgcc gtgctggcga    9707
aaagcatcag aaaggatacg ctcgggcttg aaccgcatga gatcgcggct ctatatcgtg    9767
agaggaacgc aatgcttttc gcgattcgag aagggattat tgccaccaat cgtgaaggcg    9827
tcgtcaccat gatgaacgta tcggcggccg agatgctgaa gctgcccgag cctgtgatcc    9887
atcttcctat agatgacgtc atgccgggag cagggctgat gtctgtgctt gaaaaaggag    9947
aaatgctgcc gaaccaggaa gtaagcgtca acgatcaagt gtttattatc aatacgaaag   10007
tgatgaatca aggcgggcag gcgtatggga ttgtcgtcag cttcagggag aaaacagagc   10067
tgaagaagct gatcgacaca ttgacagagg ttcgcaaata ttcagaggat ctcagggcgc   10127
agactcatga attttcaaat aagctttatg cgattttagg gctgc                   10172
```

<210> SEQ ID NO 14
<211> LENGTH: 380
<212> TYPE: PRT
<213> ORGANISM: Artificial Sequence
<220> FEATURE:
<223> OTHER INFORMATION: Synthetic Construct

<400> SEQUENCE: 14

```
Met Lys Lys Pro Leu Gly Lys Ile Val Ala Ser Thr Ala Leu Leu
        -190             -185                 -180

Ile Ser Val Ala Phe Ser Ser Ser Ile Ala Ser Ala Thr Gly
        -175             -170                 -165

Ala Leu Pro Gln Ser Pro Thr Pro Glu Ala Asp Ala Val Ser Met
        -160             -155                 -150

Gln Glu Ala Leu Gln Arg Asp Leu Asp Leu Thr Ser Ala Glu Ala
        -145             -140                 -135
```

```
Glu Glu Leu  Leu Ala Ala Gln Asp  Thr Ala Phe Glu Val  Asp Glu
        -130            -125              -120

Ala Ala Ala  Glu Ala Ala Gly Asp  Ala Tyr Gly Gly Ser  Val Phe
        -115            -110              -105

Asp Thr Glu  Ser Leu Glu Leu Thr  Val Leu Val Thr Asp  Ala Ala Ala
        -100            -95               -90

Val Glu Ala  Val Glu Ala Thr Gly  Ala Gly Thr Glu Leu  Val Ser Tyr
        -85             -80               -75

Gly Ile Asp  Gly Leu Asp Glu Ile  Val Gln Glu Leu Asn  Ala Ala Asp
-70                 -65               -60                   -55

Ala Val Pro  Gly Val Val Gly Trp  Tyr Pro Asp Val Ala  Gly Asp Thr
             -50                 -45                   -40

Val Val Leu  Glu Val Leu Glu Gly  Ser Gly Ala Asp Val  Ser Gly Leu
             -35                 -30                   -25

Leu Ala Asp  Ala Gly Val Asp Ala  Ser Ala Val Glu Val  Thr Thr Ser
             -20                 -15                   -10

Asp Gln Pro  Glu Leu Tyr Ala Asp  Ile Ile Gly Leu Ala  Tyr Thr
-5                  -1  1                5                    10

Met Gly Gly  Arg Cys Ser Val Gly  Phe Ala Ala Thr Asn  Ala Ala Gly
             15                  20                    25

Gln Pro Gly  Phe Val Thr Ala Gly  His Cys Gly Arg Val  Gly Thr Gln
             30                  35                    40

Val Thr Ile  Gly Asn Gly Arg Gly  Val Phe Glu Gln Ser  Val Phe Pro
             45                  50                    55

Gly Asn Asp  Ala Ala Phe Val Arg  Gly Thr Ser Asn Phe  Thr Leu Thr
             60                  65                    70

Asn Leu Val  Ser Arg Tyr Asn Thr  Gly Gly Tyr Ala Thr  Val Ala Gly
75                  80                  85                    90

His Asn Gln  Ala Pro Ile Gly Ser  Ser Val Cys Arg Ser  Gly Ser Thr
             95                  100                   105

Thr Gly Trp  His Cys Gly Thr Ile  Gln Ala Arg Gly Gln  Ser Val Ser
             110                 115                   120

Tyr Pro Glu  Gly Thr Val Thr Asn  Met Thr Arg Thr Thr  Val Cys Ala
             125                 130                   135

Glu Pro Gly  Asp Ser Gly Gly Ser  Tyr Ile Ser Gly Thr  Gln Ala Gln
             140                 145                   150

Gly Val Thr  Ser Gly Gly Ser Gly  Asn Cys Arg Thr Gly  Gly Thr Thr
155                 160                 165                   170

Phe Tyr Gln  Glu Val Thr Pro Met  Val Asn Ser Trp Gly  Val Arg Leu
             175                 180                   185

Arg Thr

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
ggagctctga aaaaaggag aggataaaga atgaa                           35

<210> SEQ ID NO 16
<211> LENGTH: 29
<212> TYPE: DNA
<213> ORGANISM: Artificial Sequence
<220> FEATURE:
```

```
<223> OTHER INFORMATION: Primer

<400> SEQUENCE: 16
gcgttccgat aatcgcggtg acaatgccg                                              29

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ttcatgagtc tgcgccctga gatcctctg                                              29

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
taatcgcatg ttcaatccgc tccataatcg                                             30

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
cccaacggtt tcttcattct ttatcctctc cttttttca gagc                              44

<210> SEQ ID NO 20
<211> LENGTH: 1164
<212> TYPE: DNA
<213> ORGANISM: Artificial Sequence
<220> FEATURE:
<223> OTHER INFORMATION: Protease 22
<220> FEATURE:
<221> NAME/KEY: CDS
<222> LOCATION: (1)..(1164)
<220> FEATURE:
<221> NAME/KEY: sig_peptide
<222> LOCATION: (1)..(81)
<220> FEATURE:
<221> NAME/KEY: mat_peptide
<222> LOCATION: (577)..(1164)

<400> SEQUENCE: 20 atg aaa aaa ccg ctg gga aaa att gtc gca agc aca gca ctt ctt         45
Met Lys Lys Pro Leu Gly Lys Ile Val Ala Ser Thr Ala Leu Leu
   -190             -185                 -180 att tca gtg gca ttt agc tca tct att gca tca gca gct aca gga         90
Ile Ser Val Ala Phe Ser Ser Ser Ile Ala Ser Ala Ala Thr Gly
       -175             -170                 -165 gca tta ccg cag tct ccg aca ccg gaa gca gat gca gtc tca atg        135
Ala Leu Pro Gln Ser Pro Thr Pro Glu Ala Asp Ala Val Ser Met
   -160             -155                 -150 caa gaa gca ctg caa aga gat ctt gat ctt aca tca gca gaa gca        180
Gln Glu Ala Leu Gln Arg Asp Leu Asp Leu Thr Ser Ala Glu Ala
   -145             -140                 -135 gaa gaa ctt ctt gct gca caa gat aca gca ttt gaa gtg gat gaa        225
Glu Glu Leu Leu Ala Ala Gln Asp Thr Ala Phe Glu Val Asp Glu
   -130             -125                 -120
```

```
gca gcg gca  gaa gca gca gga gat  gca tat ggc ggc tca  gtt ttt      270
Ala Ala Ala  Glu Ala Ala Gly Asp  Ala Tyr Gly Gly Ser  Val Phe
        -115              -110              -105 gat aca gaa  tca ctt gaa ctt aca  gtt ctt gtt aca gat  gca gca gca  318
Asp Thr Glu  Ser Leu Glu Leu Thr  Val Leu Val Thr Asp  Ala Ala Ala
        -100              -95               -90 gtt gaa gca  gtt gaa gca aca gga  gca gga aca gta ctt  gtt tca tat  366
Val Glu Ala  Val Glu Ala Thr Gly  Ala Gly Thr Val Leu  Val Ser Tyr
        -85               -80               -75 gga att gat  ggc ctt gat gaa att  gtt caa gaa ctg aat  gca gct gat  414
Gly Ile Asp  Gly Leu Asp Glu Ile  Val Gln Glu Leu Asn  Ala Ala Asp
-70              -65               -60               -55 gct gtt ccg  ggc gtt gtt ggc tgg  tat ccg gat gtt gct  gga gat aca  462
Ala Val Pro  Gly Val Val Gly Trp  Tyr Pro Asp Val Ala  Gly Asp Thr
        -50               -45               -40 gtt gtc ctt  gaa gtt ctt gaa gga  tca ggc gca gat gtt  tca ggc ctg  510
Val Val Leu  Glu Val Leu Glu Gly  Ser Gly Ala Asp Val  Ser Gly Leu
        -35               -30               -25 ctg gca gac  gca gga gtc gat gca  tca gca gtt gaa gtt  aca aca tca  558
Leu Ala Asp  Ala Gly Val Asp Ala  Ser Ala Val Glu Val  Thr Thr Ser
        -20               -15               -10 gat caa ccg  gaa ctt tat gca gat  att att ggc ggc ctg  gca tat tat  606
Asp Gln Pro  Glu Leu Tyr Ala Asp  Ile Ile Gly Gly Leu  Ala Tyr Tyr
        -5               -1   1                5                10 atg ggc ggc  aga tgc agc gtt ggc  ttt gca gca aca aat  gca tca ggc  654
Met Gly Gly  Arg Cys Ser Val Gly  Phe Ala Ala Thr Asn  Ala Ser Gly
             15                20                25 caa ccg ggc  ttt gtt aca gca ggc  cat tgc ggc aca gtt  ggc aca cca  702
Gln Pro Gly  Phe Val Thr Ala Gly  His Cys Gly Thr Val  Gly Thr Pro
        30                35                40 gtt tca att  ggc aat ggc aaa ggc  gtt ttt gaa cga agc  att ttt ccg  750
Val Ser Ile  Gly Asn Gly Lys Gly  Val Phe Glu Arg Ser  Ile Phe Pro
        45                50                55 ggc aat gat  tca gca ttt gtt aga  ggc aca tca aat ttt  aca ctt aca  798
Gly Asn Asp  Ser Ala Phe Val Arg  Gly Thr Ser Asn Phe  Thr Leu Thr
    60                65                70 aat ctg gtt  tca aga tat aat tca  ggc ggc tat gca aca  gtt gca ggc  846
Asn Leu Val  Ser Arg Tyr Asn Ser  Gly Gly Tyr Ala Thr  Val Ala Gly
75                80                85                90 cat aat caa  gca ccg att ggc tca  gca gtt tgc aga tca  ggc tca aca  894
His Asn Gln  Ala Pro Ile Gly Ser  Ala Val Cys Arg Ser  Gly Ser Thr
             95                100               105 aca ggc tgg  cat tgc ggc aca att  caa gca aga aat caa  aca gtt agg  942
Thr Gly Trp  His Cys Gly Thr Ile  Gln Ala Arg Asn Gln  Thr Val Arg
        110               115               120 tat ccg caa  ggc aca gtt tat agt  ctg aca aga aca aca  gtt tgt gca  990
Tyr Pro Gln  Gly Thr Val Tyr Ser  Leu Thr Arg Thr Thr  Val Cys Ala
        125               130               135 gaa ccg ggc  gat tca ggc ggc tca  tat att agc ggc act  caa gca caa  1038
Glu Pro Gly  Asp Ser Gly Gly Ser  Tyr Ile Ser Gly Thr  Gln Ala Gln
        140               145               150 ggc gtt aca  tca ggc ggc tca ggc  aat tgc agt gct ggc  ggc aca aca  1086
Gly Val Thr  Ser Gly Gly Ser Gly  Asn Cys Ser Ala Gly  Gly Thr Thr
155               160               165               170 tat tac caa  gaa gtt aat ccg atg  ctt agt tca tgg ggc  ctt aca ctt  1134
Tyr Tyr Gln  Glu Val Asn Pro Met  Leu Ser Ser Trp Gly  Leu Thr Leu
             175               180               185 aga aca caa  tcg cat gtt caa tcc  gct cca                           1164
Arg Thr Gln  Ser His Val Gln Ser  Ala Pro
        190               195
```

<210> SEQ ID NO 21
<211> LENGTH: 388
<212> TYPE: PRT
<213> ORGANISM: Artificial Sequence
<220> FEATURE:
<223> OTHER INFORMATION: Synthetic Construct

<400> SEQUENCE: 21

```
Met Lys Lys Pro Leu Gly Lys Ile Val Ala Ser Thr Ala Leu Leu
        -190             -185             -180

Ile Ser Val Ala Phe Ser Ser Ile Ala Ser Ala Ala Thr Gly
    -175             -170             -165

Ala Leu Pro Gln Ser Pro Thr Pro Glu Ala Asp Ala Val Ser Met
        -160             -155             -150

Gln Glu Ala Leu Gln Arg Asp Leu Asp Leu Thr Ser Ala Glu Ala
        -145             -140             -135

Glu Glu Leu Leu Ala Ala Gln Asp Thr Ala Phe Glu Val Asp Glu
        -130             -125             -120

Ala Ala Ala Glu Ala Ala Gly Asp Ala Tyr Gly Gly Ser Val Phe
        -115             -110             -105

Asp Thr Glu Ser Leu Glu Leu Thr Val Leu Val Thr Asp Ala Ala
        -100              -95              -90

Val Glu Ala Val Glu Ala Thr Gly Ala Gly Thr Val Leu Val Ser Tyr
    -85              -80              -75

Gly Ile Asp Gly Leu Asp Glu Ile Val Gln Glu Leu Asn Ala Ala Asp
-70              -65              -60              -55

Ala Val Pro Gly Val Val Gly Trp Tyr Pro Asp Val Ala Gly Asp Thr
                -50              -45              -40

Val Val Leu Glu Val Leu Glu Gly Ser Gly Ala Asp Val Ser Gly Leu
            -35              -30              -25

Leu Ala Asp Ala Gly Val Asp Ala Ser Ala Val Glu Val Thr Thr Ser
        -20              -15              -10

Asp Gln Pro Glu Leu Tyr Ala Asp Ile Ile Gly Gly Leu Ala Tyr Tyr
    -5              -1   1              5                      10

Met Gly Gly Arg Cys Ser Val Gly Phe Ala Ala Thr Asn Ala Ser Gly
                15              20              25

Gln Pro Gly Phe Val Thr Ala Gly His Cys Gly Thr Val Gly Thr Pro
            30              35              40

Val Ser Ile Gly Asn Gly Lys Gly Val Phe Glu Arg Ser Ile Phe Pro
        45              50              55

Gly Asn Asp Ser Ala Phe Val Arg Gly Thr Ser Asn Phe Thr Leu Thr
    60              65              70

Asn Leu Val Ser Arg Tyr Asn Ser Gly Gly Tyr Ala Thr Val Ala Gly
75              80              85              90

His Asn Gln Ala Pro Ile Gly Ser Ala Val Cys Arg Ser Gly Ser Thr
                95              100             105

Thr Gly Trp His Cys Gly Thr Ile Gln Ala Arg Asn Gln Thr Val Arg
            110             115             120

Tyr Pro Gln Gly Thr Val Tyr Ser Leu Thr Arg Thr Thr Val Cys Ala
        125             130             135

Glu Pro Gly Asp Ser Gly Gly Ser Tyr Ile Ser Gly Thr Gln Ala Gln
    140             145             150

Gly Val Thr Ser Gly Gly Ser Gly Asn Cys Ser Ala Gly Gly Thr Thr
155             160             165             170
```

```
Tyr Tyr Gln Glu Val Asn Pro Met Leu Ser Ser Trp Gly Leu Thr Leu
            175                 180                 185
Arg Thr Gln Ser His Val Gln Ser Ala Pro
            190                 195
```